(12) United States Patent
Ng et al.

(10) Patent No.: US 7,553,947 B2
(45) Date of Patent: Jun. 30, 2009

(54) METHOD FOR GENE IDENTIFICATION SIGNATURE (GIS) ANALYSIS

(75) Inventors: Patrick Ng, Singapore (SG); Chialin Wei, Singapore (SG); Yijun Ruan, Singapore (SG)

(73) Assignee: Agency for Science, Technology and Research, Singapore (SG)

( * ) Notice: Subject to any disclaimer, the term of this patent is extended or adjusted under 35 U.S.C. 154(b) by 0 days.

(21) Appl. No.: 11/610,118

(22) Filed: Dec. 13, 2006

(65) Prior Publication Data
US 2007/0161024 A1 Jul. 12, 2007

Related U.S. Application Data

(60) Division of application No. 11/045,468, filed on Jan. 31, 2005, which is a continuation-in-part of application No. 10/664,234, filed on Sep. 17, 2003.

(51) Int. Cl.
*C12N 15/11* (2006.01)
*C12N 15/63* (2006.01)
*C07H 21/04* (2006.01)

(52) U.S. Cl. .................... 536/23.1; 536/24.2; 435/320.1
(58) Field of Classification Search .............. 435/320.1; 536/24.2, 23.1
See application file for complete search history.

(56) References Cited

U.S. PATENT DOCUMENTS

| | | | |
|---|---|---|---|
| 4,766,072 | A | 8/1988 | Jendrisak |
| 6,054,276 | A | 4/2000 | Macevicz |
| 6,136,537 | A * | 10/2000 | Macevicz ...................... 435/6 |
| 6,143,528 | A | 11/2000 | Hayashizaki |
| 6,303,308 | B1 * | 10/2001 | Halle et al. ................... 435/6 |
| 6,383,743 | B1 | 5/2002 | Kinzler |
| 6,410,243 | B1 * | 6/2002 | Wyrick et al. ................. 435/6 |
| 6,498,013 | B1 | 12/2002 | Velculescu |
| 2002/0025561 | A1 | 2/2002 | Hodgson |
| 2002/0065609 | A1 | 5/2002 | Ashby |
| 2002/0102604 | A1 | 8/2002 | Milne Edwards et al. |
| 2003/0008290 | A1 | 1/2003 | Velculescu et al. |
| 2004/0146866 | A1 | 7/2004 | Fu |
| 2005/0059022 | A1 | 3/2005 | Ruan et al. |
| 2005/0255501 | A1 | 11/2005 | Ng et al. |

FOREIGN PATENT DOCUMENTS

| | | |
|---|---|---|
| EP | 0761822 B1 | 5/2003 |
| WO | WO 01/48247 A2 | 7/2001 |
| WO | WO 02/10438 A3 | 2/2002 |
| WO | WO02066682 A2 * | 8/2002 |
| WO | WO 03/106672 A2 | 12/2003 |
| WO | WO 2004/050918 A1 | 6/2004 |
| WO | WO 2006003721 A1 | 1/2006 |

OTHER PUBLICATIONS

Roulet et al (Nature Biotechniques (2002) vol. 20, pp. 831-835).*

Moncke-Buchner et al (Nucleic Acids Research (2002) vol. 30, No. 16 e83 pp. 1-7).*

Enzymes with nonpalindromic sequences (neb.com/nebecomm/tech_reference/restriction_enzyme/nonpalindromes.asp).*

Single cutters of pZero (tools.neb.com/NEBcutter2/listbycuts.php?name=07fc4160-pzero&numcuts=1).*

Adams, Mark D., et al., "Complementary DNA Sequencing: Expressed Sequence Tags and Human Genome Project," *Science*, New Series, Jun. 21, 1991, pp. 1651-1656, vol. 252, No. 5013.

Brenner, Sydney, et al., "Gene expression analysis by massively parallel signature sequencing (MPSS) on microbed arrays," *Nature Biotechnology*, Jun. 2000, pp. 630-634, vol. 18, No. 6. Nature America Inc.

Brenner, Sydney, et al., "In vitro cloning of complex mixtures of DNA on microbeads: Physical separation of differentially expressed cDNAs," *PNAS*, Feb. 15, 2000, pp. 1665-1670, vol. 97, No. 4.

Iyer, Vishwanath R., et al., "Genomic binding sites of the yeast cell-cycle transcription factors SBF and MBF," *Nature*, Jan. 25, 2001, pp. 533-538, vol. 409, No. 6819. Macmillan Magazines Ltd.

Jongeneel, C. Victor, et al., "Comprehensive sampling of gene expression in human cell lines with massively parallel signature sequencing," *PNAS*, Apr. 15, 2003, pp. 4702-4705, vol. 100, No. 8.

Kaeser, M.D., et al., Chromatin immunoprecipitation analysis fails to support the latency model for regulation of p53 DNA binding activity in vivo, *PNAS*, Jan. 8, 2002, pp. 95-100, vol. 99, No. 1.

Lieb, Jason D., et al., "Promoter-specific binding of Rap1 revealed by genome-wide maps of protein-DNA association," *Nature Genetics*, Aug. 2001, pp. 327-334, vol. 28, No. 4. Nature Publishing Group.

Mathupala, Saroj P., et al., "'In-gel' purified ditags direct synthesis of highly efficient SAGE Libraries," *BMC Genomics*, Aug. 1, 2002, p. 20, vol. 3, No. 1.

Ng, Patrick, et al., "Gene identification signature (GIS) analysis for transcriptome chracaterization and genome annotation," *Nature Methods*, Feb. 2005, pp. 105-111, vol. 2, No. 2.

Oren, M., et al., "Decision making by p53: life, death and cancer," *Cell Death and Differentiation*, 2003, pp. 431-442, vol. 10. Nature Publishing Group.

Ren, Bing et al., "Genome-Wide Location and Function of DNA Binding Proteins," *Science*, Dec. 22, 2000, pp. 2306-2309, vol. 290, No. 5500.

Ruan, Yijun et al., "Interrogating the transcriptome," *Trends in Biotechnology*, Jan. 2004, pp. 23-30, vol. 22, No. 1. Elsevier, Cambridge, GB.

(Continued)

*Primary Examiner*—Sarae Bausch
*Assistant Examiner*—Steven C Pohnert
(74) *Attorney, Agent, or Firm*—Rothwell, Figg, Ernst and Manbeck

(57) ABSTRACT

A method of identifying at least a nucleic acid molecule fragment to which a protein of interest binds, comprising: (i) preparing at least one nucleic acid molecule fragment to which a protein binds; (ii) isolating the 5' terminus and the 3' terminus of the nucleic acid fragment(s) and linking the 5' terminus and 3' terminus to create the at least one ditag; (iii) sequencing the ditag; and (iv) mapping the ditag sequence(s) to the genome.

1 Claim, 20 Drawing Sheets

OTHER PUBLICATIONS

Saha, Saurabh, et al., "Using the transcriptome to annotate the genome," *Nature Biotechnology*, May 2002, pp. 508-512, vol. 19.

Taverner, Nicola, et al., "Identifying transcriptional targets," *Genome Biology*, 2004, pp. 210.1-210.7, vol. 5, No. 3.

Velculescu, Victor E., et al., "Serial Analysis of Gene Expression," *Science*, Oct. 20, 1995, pp. 484-487, vol. 270.

Wei, Chia-Lin, et al., "5' Long serial analysis of gene expression (LongSAGE) and 3' LongSAGE for transcriptome characterization and genome annotation," *PNAS*, 2004, pp. 11701-11706, vol. 101, No. 32.

Yamamoto, Mikio, et al., "Use of serial analysis of gene expression (SAGE) technology," *Journal of Immunological Methods*, Apr. 1, 2001, pp. 45-66, vol. 250, No. 1-2. Elsevier B.V., Amsterdam, NL.

New England Biolabs 2000/2001 Catalog, p. 196.

Alam, et al., "A novel vector for the expression of SCR domains in insect cells," Journal of Immunological Methods, 293: 107-113 (2004).

Tucholski et al., "MmeI, a class-IIS restriction endonuclease: purification and characterization," Gene, 157: 87-92 (1995).

GenBank accession No. X65305.2, Jan. 2000.

Result 24 of search of SEQ ID No. 18 in GenEmbl, 2006.

Margulies, et al., "Genome sequencing in microfabricated high-density picolitre reactors," Nature, 437: 376-380 (Sep. 15, 2005) (with one page Corrigendum dated May 4, 2006).

Li, et al., "Alteration of the Cleavage Distance of Fok I Restriction Endonuclease by Insertion Mutagenesis," PNAS 90: 2764-2768, 1993.

Strausberg, et al., "The Mammalian Gene Collection," Science, 286: 455-457 (1999).

www.Invitrogen.com/content/sfs/vectors/pzero1_rest.text, Feb. 23, 2007, 7 pages.

Belfort et al., "Horning endonucleases: keeping the house in order," Nucleic Acids Research, 25(17): 3379-3388 (1997).

Klug, et al., "All you wanted to know about SELEX," Molecular Biology Reports, 20: 97-107 (1994).

Zhang, Z.H. et al., "Mapping of transcription start sites in *Saccharomyces cerevisiae* using 5' SAGE". Nucleic Acids Res., vol. 33(9): 2838-2851, 2005.

Chum, Winnie W.Y. et al., "Modification of LongSAGE for obtaining and cloning long concatemers", BioTechniques, vol. 39(5): 637-640, 2005.

\* cited by examiner

Figure 10 pGIS1 sequence

```
           XhoI              NotI                          MmeI
           ~~~~              ~~~~                          ~~~~
      EcoRI                           BamHI
      ~~~~~                           ~~~~~
  1   GGGCGAATTC TCGAGCGGCC GCGGATCCGA CGAGAGCGCC TGCGTACGGC TCGCCGCGGT GGCTGGCGCT ACTTCGGAGG AGCCCGACGC GGCGCGGTCG
      CCCGCTTAAG AGCTCGCCGG CGCCTAGGCT GCTCTCGCGG ACGCATGCCG AGCGGCGCCA CCGACCGCGA AGAAGCCTCC TCGGGCTGCG CCGCGCCAGC

MmeI
                                                                                       ~~~~
 101  TTTTTATACA TTCCCGCGCG GAGGCAAACGG AAGGGCGGGG CGCCCTCGTGA TTAGGCCGCG GAGGTCACAG GCTCTCGTTGT CATGAAGGTG AAAATTAAAT
      AAAAATATGT AAGGGCGCGC CTCCGTTGCC TTCCCGCCCC GCGGAGCACT AATCCGGCGC CTCCAGTGTC CGAGACAACA GTACTTCCAC TTTTAATTTA
      MmeI
      ~~~~
 201  GTTGGAATGG TGTGCCACT TGGCTCTGGG TAGCCAATGA TGAGAACTGC GGCATCTGCA GGATGGCGTT TAATGGCTGC TGTCCAGACT GTAAGGTGCC
      CAACCTTACC ACACGGTGA ACCGAGACCC ATCGGTTACT ACTCTTGACG CCGTAGACGT CCTACCGCAA ATTACCGACG ACAGGTCTGA CATTCCACGG

301  TGGTGATGAC TGCCCCCTCG TGTGGGGACA GTGCTTCCACA TGCTCACTGCAT CCTCAAGTGG CTGAATGCGC AGCAGGTGCA GCAGCACTGC
      ACCACTACTG ACGGGGGAGC ACACCCCTGT CACGAGGGTGT ACGAAGGTGT ACGTGACGTA GGAGTTCACC GACTTACGCG TCGTCCACGT CGTCGTGACG

401  CCCATGTGTC GCCAGGAGTG GAAGTTCAAA GAGTGAAGCC CGTGCCGTGC CACTTCCCTC TCCTGTGCTG TGCCAGGCTC AGCCCCTTCC CTCCCTCCCC
      GGGTACACAG CGGTCCTCAC CTTCAAGTTT CTCACTTCGG GCACGGCACG GTGAAGGGAG AGGACACGAC ACGGTCCGAG TCGGGGAAGG GAGGGAGGGG

501  TCCCCCAGAT ACAGCACCCC AAGTCCCCTC CACACAGCAC AGTGGTGCCC AGAGATCTCG GTCTGTGCCG GGGACAAGGA TGCTTTCTGT TTGGCTGGGA
      AGGGGGTCTA TGTCGTGGGG TTCAGGGGAG GTGTGTCGTG TCACCACGGG TCTCTAGAGC CAGACACGGC CCCTGTTCCT ACGAAAGACA AACCGACCCT
                                                                                  MmeI
                                                                                  ~~~~
                                                                                         BamHI
                                                                                         ~~~~~
 601  CAAGGTTGAA AGGAGCTTTG CTGACTGTTT TGTTTTCCCA TCACATTGAC ACTTTATTCA ATAAGTAAAA CTCATTACAG TTCCAAGTCG GATCCTGGGT
      GTTCCAACTT TCCTCGAAAC GACTGACAAA ACAAAAGGGT AGTGTAACTG TGAAATAAGT TATTCATTTT GAGTAATGTC AAGGTTCAGC CTAGGACCCA
      SalI
      ~~~~
 701  CGACCTGCAG GCATGCAAGC TTGAGTATTC CCTAAATAGC TTGGCGTAAT CATGGTCATA GCTGTTTCCT GTGTGAAATT GTTATCCGCT
      GCTGGACGTC CGTACGTTCG AACTCATAAG GGATTTATCG GAACGCCATTA GTACCAGTAT CGACAAAGGA CACACTTTAA CAATAGGCGA
```

Figure 10 (continued)

```
 801  CACAATTCCA CACAACATAC GAGCCGGAAG CATAAAGTGT AAAGCCTGGG GTGCCTAATG AGTGAGCTAA CTCACATTAA TTGCGTTGCG CTCACTGCCC
      GTGTTAAGGT GTGTTGTATG CTCGGCCTTC GTATTTCACA TTTCGGACCC CACGGATTAC TCACTCGATT GAGTGTAATT AACGCAACGC GAGTGACGGG

901  GCTTTCCAGT CGGGAAACCT GTCCTGCCAG CTGCATTAAT CTGGCTTATT GAATCGGCCA ACGCGCGGCA AGAGGCGGTT TGCGTATTGG GCGCTCTTCC GCTTCCTCGC
      CGAAAGGTCA GCCCTTTGGA CAGCACGGTC GACGTAATTA GACCGAATAA CTTAGCCGGT TGCGCGCCGT TCTCCGCCAA ACGCATAACC CGCGAGAAGG CGAAGGAGCG

1001  TCACTGACTC GCTGCGCTCG GTCGTTCGGC TGCGGCGAGC GGTATCAGCT CACTCAAAGG CGGTAATACG GTTATCCACA GAATCAGGGG ATAACGCAGG
      AGTGACTGAG CGACGCGAGC CAGCAAGCCG ACGCCGCTCG CCATAGTCGA GTGAGTTTCC GCCATTATGC CAATAGGTGT CTTAGTCCCC TATTGCGTCC

1101  AAAGAACATG TGAGCAAAAG GCCAGCAAAA GGCCAGGAAC CGTAAAAAGG CCGCGTTGCT GGCGTTTTTC GATAGGCTCC GCCCCCCTGA CGAGCATCAC
      TTTCTTGTAC ACTCGTTTTC CGGTCGTTTT CCGGTCCTTG GCATTTTTCC GGCGCAACGA CCGCAAAAAG CTATCCGAGG CGGGGGGACT GCTCGTAGTG

1201  AAAAATCGAC GCTCAAGTCA GAGGTGGCGA AACCCGACAG GACTATAAAG ATACCAGGCG TTTCCCCCTG GAAGCTCCCT CGTGCGCTCT CCTGTACCGA
      TTTTTAGCTG CGAGTTCAGT CTCCACCGCT TTGGGCTGTC CTGATATTTC TATGGTCCGC AAAGGGGGAC CTTCGAGGGA GCACGCGAGA GGACATGGCT

1301  CCCTGCCGCT TACCGGATAC CTGTCCGCCT TTCTCCCTTC GGGAAGCGTG GCGCTTTCTC ATAGCTCACG CTGTAGGTAT CTCAGTTCGG TGTAGGTCGT
      GGGACGGCGA ATGGCCTATG GACAGGCGGA AAGAGGGAAG CCCTTCGCAC CGCGAAAGAG TATCGAGTGC GACATCCATA GAGTCAAGCC ACATCCAGCA

1401  TCGCTCCAAG CTGGGCTGTG TGCACGAACC CCCCGTTCAG CCCGACCGCT GCGCCTTATC CGGTAACTAT CGTCTTGAGA CCAACCCGGT AAGACACGAC
      AGCGAGGTTC GACCCGACAC ACGTGCTTGG GGGGCAAGTC GGGCTGGCGA CGCGGAATAG GCCATTGATA GCAGAACTCT GGTTGGGCCA TTCTGTGCTG

1501  TTATCGCCAC TGGCAGCAGC CACTGGTAAC AGGATTAGCA GAGCGAGGTA TGTAGGCGGT GCTACAGAGT TCTTGAAGTG GTGGCTAAC TACGGCTACA
      AATAGCGGTG ACCGTCGTCG GTGACCATTG TCCTAATCGT CTCGCTCCAT ACATCCGCCA CGATGTCTCA AGAACTTCAC CACCGATTG ATGCCGATGT

1601  CTAGAAGGAC AGTATTTGGT ATCTGCGCTC TGCTGAAGCC AGTTACCTTC GGAAAAAGAG TTGGTAGCTC TTGATCCGGC AACAAACCA CCGCTGGTAG
      GATCTTCCTG TCATAAACCA TAGACGCGAG ACGACTTCGG TCAATGGAAG CCTTTTTCTC AACCATCGAG AACTAGGCCG TTTGTTTGGT GGCGACCATC

1701  CGGTGGTTTT TTTGTTTGCA AGCAGCAGAT TACGCGCAGA AAAAAAGGAT CTCAAGAAGA TCCTTTGATC TTTTCTACGG GGTCTGACGC TCAGTGGAAC
      GCCACCAAAA AAACAAACGT TCGTCGTCTA ATGCGCGTCT TTTTTTCCTA GAGTTCTTCT AGGAAACTAG AAAGATGCC CCAGACTGCG AGTCACCTTG

1801  GAAAACTCAC GTTAAGGGAT TTTGGTCATG AGATTATCAA AAAGGATCTT CACCTAGATC CTTTTAAATT AAAAATGAAG TTTTAAATCA ATCTAAAGTA
      CTTTTGAGTG CAATTCCCTA AAACCAGTAC TCTAATAGTT TTTCCTAGAA GTGGATCTAG GAAAATTTAA TTTTTACTTC AAAATTTAGT TAGATTTCAT

1901  TATATGAGTA AACTTGGTCT GACAGTTACC AATGCTTAAT CAGTGAGGCA CCTATCTCAG CGATCTGTCT ATTTCGTTCA TCCATAGTTG CCTGACTCCC
      ATATACTCAT TTGAACCAGA CTGTCAATGG TTACGAATTA GTCACTCCGT GGATAGAGTC GCTAGACAGA TAAAGCAAGT AGGTATCAAC GGACTGAGGG

2001  CGTCGTGTAG ATAACTACGA TACGGGAGGG CTTACCATCT GGCCCCAGTG CTGCAATGAT ACCCGCGAGAC CCAACGCTCAC CGGCTCCAGA TTTATCAGCA
      GCACCACATC TATTGATGCT ATGCCCTCCC GAATGGTAGA CCGGGGTCAC GACGTTACTA TGGGCGCTCTG GGTGCGAGTG GCCGAGGTCT AAATAGTCGT

2101  ATAAACCAGC CAGCCGGAAG GGCCGAGCGC AGAAGTGGTC CTGCAACTTT ATCCGCCTCC ATCCAGTCTA TTAATTGTTG CCGGGAAGCT AGAGTAAGTA
```

Figure 10 (continued)

```
      TATTTGGTCG GTCGGCCTTC CCGGCTCGCG TCTTCACCAG GACGTTGAAA TAGGCGGAGG TAGGTCAGAT AATTAACAAC GGCCCTTCGA TCTCATTCAT

2201  GTTCGCCAGT TAATAGTTTG CGCAACGTTG TTGGCATTGC TACAGGCATC GTGGTGTCAC GCTCGTCGTT TGGTATGGCT TCATTCAGCT CCGTTCCCA
      CAAGCGGTCA ATTATCAAAC GCGTTGCAAC AACCGTAACG ATGTCCGTAG CACCACAGTG CGAGCAGCAA ACCATACCGA AGTAAGTCGA GGCCAAGGT

2301  ACGATCAAGG CCAGTTACAT GATCCCCCAT GTTGTGCAAA AAAGCGGTTA GCTCCCTTCGG TCCTCCGATC GTTGTCAGAA GTAAGTTGGC CGCAGTGTTA
      TGCCTAGTTCC GCTCAATGTA CTAGGGGTA CAACACGTTT TTTCGCCAAT CGAGGAGCC AGGAGGCTAG CAACAGTCTT CATTCAACCG GCGTCACAT

2401  TCACTCATGG TTATGCAGC ACTGCATAAT TCTCTTACTG TCATGCCATC CGTAAGATGC TTTTCTGTGA CTGGTGAGTA CTCAACCAAG TCATTCTGAG
      AGTGAGTACC AATACCCTCG TGACGTATTA AGAGAATGAC AGTACGGTAG GCATTCTACG GACCACTCAT AAAAGACACT GACCACTCAT GAGTTGGTTC AGTAAGACTC

2501  AATAGTGTAT GCGGCGACCG AGTTGCTCTT GCCCGGCGTC AATACGGGAT AATACCGCGC CACATAGCAG AACTTTAAAA GTGCTCATCA TTGGAAAACG
      TTATCACATA CGCCGCTGGC TCAACGAGAA CGGGCCGCA TTATGCCCTA TTATGGCGCG GTGTATCGTC TTGAAATTTT CACGAGTAGT AACCTTTGC

2601  TTCTTCGGGG CGAAAACTCT CAAGGATCTT ACCGCTGTTG AGATCCAGTT CGATGTAACC CACTCGTGCA CCCAACTGAT CTTCAGCATC TTTTACTTTC
      AAGAGCCCC GCTTTTGAGA GTTCCTAGAA TGGCGACAAC TCTAGGTCAA GCTACATTGG GTGAGCACGT GGGTTGACTA GAAGTCGTAG AAAATGAAAG

2701  ACCAGCGTTT CTGGGTGAGC AAAAACAGGA AGGCAAAATG CCGCAAAAAA GGGAATAAGG GCGACACGGA AATGTTGAAT ACTCATACTC TTCCTTTTC
      TGGTCGCAAA GACCCACTCG TTTTTGTCCT TCCGTTTTAC GGCGTTTTT CCCTTATTCC CGCTGTGCCT TTACAACTTA TGAGTATGAG AAGGAAAAAG

2801  AATATTATTG AAGCATTTAT CAGGGTTATT GTCTCATGAG CGGATACATA TTTGAATGTA TAAACAAATA GGGGTTCCGC GCACATTTCC
      TTATAATAAC TTCGTAAATA GTCCCAATAA CAGAGTACTC GCCTATGTAT AAACTTACAT ATTTGTTTAT CCCCAAGGCG CGTGTAAAGG

2901  CCGAAAAGTG CCACCTGACG TCTAAGAAAC CATTATTATC ATGACATTAA CCTATAAAAA TAGGCGTATC ACGAGGCCCT TTCGTCTGC GCGTTTCGGT
      GGCTTTTCAC GGTGGACTGC AGATTCTTTG GTAATAATAG TACTGTAATT GGATATTTTT ATCCGCATAG TGCTCCGGGA AAGCAGAGCG CGCAAAGCCA

3001  GATGAGGGTG AAAACCTCTG ACACATGCAG CTCCCGGAGA CGGTCACAGC TTGTCTGTAA GCGGATGCCG GGAGCAGACA AGCCCGTCAG GGGCGTCAG
      CTACTGCCAC TTTTGGAGAC TGTGTACGTC GAGGGCCTCT GCCAGTGTCG AACAGACATT CGCCTACGGC CCTCGTCTGT TCGGGCAGTC CCGGCAGTC

3101  CGGGTGTTGG CGGGTGTCGG GGCTGGCTTA ACTATGCGGC ATCAGAGCAG ATTGTACTGA GAGTGCACCA TATGCGGTGT GAAATACCGC ACAGATGCGT
      GCCCACAACC GCCCACAGCC CCGACCGAAT TGATACGCCG TAGTCTCGTC TAACATGACT CTCACGTGGT ATACGCCACA CTTTATGGCG TGTCTACGCA

3201  AAGGAGAAA TACCGCATCA GGCGCCATTC GCCATTCAGG CTGCGCAACT GTTGGGAAGG GCGATCGGTG CGGGCCTCTT CGCTATTACG CCAGCTGGCG
      TTCCTCTTTT ATGGCGTAGT CGGTAAGCC GACGCGTTGA CAACCCTTCC CGCTAGCCAC GCCCGGAGAA GCGATAATGC GGTCGACCGC

3301  AAAGGGGAT GTGCTGCAAG GCGATTAAGT TGGGTAACGC CAGGGTTTTC CCAGTCACGA CGTTGTAAAA CGACGGCCAG TGAATTGTAA TACGACTCAC
      TTTCCCCCTA CACGACGTTC CGCTAATTCA ACCCATTGCG GTCCCAAAAG GGTCAGTGCT GCAACATTTT GCTGCCGGTC ACTTAACATT ATGCTGAGTG

3401  TATA
      ATAT
```

Figure 17

```
           EcoRI    EcoRV      BseRI           BamHI     XhoI   BamHI            BseRI              PstI
           ~~~~~    ~~~~~      ~~~~~           ~~~~~     ~~~~   ~~~~~            ~~~~~              ~~~~
                        NotI                         MmeI    MmeI                            SalI
                        ~~~~                         ~~~~    ~~~~                            ~~~~
     1     GGGCGAATTC GATATCGCCG CCGGACGAG TATGGATCCG ACTCGAGTCG GATCCTGGCT CCTCGTCGAC CTGCAGGCAT GCAAGCTTGA GTATTCTATA
           CCCGCTTAAG CTATAGCGGC GGCGCTCCTC ATACCTAGGC TGAGCTCAGC CTAGGACCGA GGAGCAGCTG GACGTCCGTA CGTTCGAACT CATAAGATAT
   101     GTGTCACCTA AATAGCTTGG CGTAATCATG GTCATAGCTG TTTCCTGTGT GAAATTGTTA TCCGCTCACA ATTCCACACA ACATACGAGC CGGAAGCATA
           CACAGTGGAT TTATCGAACC GCATTAGTAC CAGTATCGAC AAAGGACACA CTTTAACAAT AGGCGAGTGT TAAGGTGTGT TGTATGCTCG GCCTTCGTAT
   201     AAGTGTAAAG CCTGGGGTGC CTAATGAGTG AGCTAACTCA CATTAATTGC GTTGCGCTCA CTGCCCGCTT TCCAGTCGGG AAACCTGTCG TGCCAGCTGC
           TTCACATTTC GGACCCCACG GATTACTCAC TCGATTGAGT GTAATTAACG CAACGCGAGT GACGGGCGAA AGGTCAGCCC TTTGGACAGC ACGGTCGACG
   301     ATTAATGAAT CGGCCAACGC GCGGGGAGAG GCGGTTTGCG TATTGGGCGC TCTTCCGCTT CCTCGCTCAC TGACTCGCTG CGCTCGGTCG TTCGGCTGCG
           TAATTACTTA GCCGGTTGCG CGCCCCTCTC CGCCAAACGC ATAACCCGCG AGAAGGCGAA GGAGCGAGTG ACTGAGCGAC GCGAGCCAGC AAGCCGACGC
   401     GCGAGCGGTA TCAGCTCACT CAAAGGCGGT AATACGGTTA TCCACAGAAT CAGGGGATAA CGCAGGAAAG AACATGTGAG CAAAAGGCCA GCAAAAGGCC
           CGCTCGCCAT AGTCGAGTGA GTTTCCGCCA TTATGCCAAT AGGTGTCTTA GTCCCCTATT GCGTCCTTTC TTGTACACTC GTTTTCCGGT CGTTTTCCGG
   501     AGGAACCGTA AAAAGGCCGC GTTGCTGGCG TTTTTCGATA GGCTCCGCCC CCCTGACGAG CATCACAAAA ATCGACGCTC AAGTCAGAGG TGGCGAAACC
           TCCTTGGCAT TTTTCCGGCG CAACGACCGC AAAAAGCTAT CCGAGGCGGG GGGACTGCTC GTAGTGTTTT TAGCTGCGAG TTCAGTCTCC ACCGCTTTGG
   601     CGACAGGACT ATAAAGATAC CAGGCGTTTC CCCCCTGGAAG CTCCCCTGTG GCGCTCTCCTG TACCGACCCT GCCGCTTACC GGATACCGTC CCGCCTTTCT
           GCTGTCCTGA TATTTCTATG GTCCGCAAAG GGGGACCTTC GAGGGAGCAC GCGAGAGGAC ATGGCTGGGA CGGCGAATGG CCTATGGCAG GGCGGAAAGA
   701     CCCTTCGGGA AGCGTGGCGC TTTTCTCATAG CTACGCTGTG AGTTATCTCA GTTCGGTGTA GGTCGTTCGC TCCAAGCTGG GCTGTGTGCA CGAACCCCCC
           GGGAAGCCCT TCGCACCGCG AAAGAGTATC GAGTGCGACA TCCATAGAGT CAAGCCACAT CCAGCAAGCG AGGTTCGACC CGACACACGT GCTTGGGGGG
   801     GTTCAGCCCG ACCGCTGCGC CTTATCCGGT AACTATCGTC TTGAGACCAA CCCGGTAAGA CACGACTTAT CGCCACTGGC AGCAGCCACT GGTAACAGGA
           CAAGTCGGGC TGGCGACGCG GAATAGGCCA TTGATAGCAG AACTCTGGTT GGGCCATTCT GTGCTGATGA GCGGTGACCG TCGTCGGTGA CCATTGTCCT
   901     TTAGCAGAGC GAGGTATGTA GGCGGTGCTA CAGAGTTCTT GAAGTGGTGG CCTAACTACG GCTACACTAG AAGGACAGTA TTTGGTATCT GCGCTCTGCT
           AATCGTCTCG CTCCATACAT CCGCCACGAT GTCTCAAGAA CTTCACCACC GGATTGATGC CGATGTGATC TTCCTGTCAT AAACCATAGA CGCGAGACGA
  1001     GAAGCCAGTT ACCTTCGGAA AAAGAGTTGG TAGCTCTTGA TCCGGCAAAC AAACCACCGC TGGTAGCGGT GGTTTTTTTG TTTGCAAGCA GCAGATTACG
           CTTCGGTCAA TGGAAGCCTT TTTCTCAACC ATCGAGAACT AGGCGAGTTTG TTTGGTGGCG ACCATCGCCA ACCATCGCCA CCAAAAAAAC AAACGTTCGT CGTCTAATGC
  1101     CGCAGAAAAA AAGGATCTCA AGAAGATCCT TTGATCTTTT CTACGGGGTC TGACGCTCAG TGGAACGAAA ACTCACGTTA AGGGATTTTG GTCATGAGAT
           GCGTCTTTTT TTCCTAGAGT TCTTCTAGGA AACTAGAAAA GATGCCCCAG ACTGCGAGTC ACCTTGCTTT TGAGTGCAAT TCCCTAAAAC CAGTACTCTA
  1201     TATCAAAAAG GATCTTCACC TAGATCCTTT TAAATTAAAA ATTTAAGTTT AATCAATCT TTATTAGTTAGA TGAGTAAACT AAGTATATA TGGTCTGACA GTTACCAATG
           ATAGTTTTC CTAGAAGTGG ATCTAGGAAA ATTTAATTTT TACTTCAAAA TGAGTAAACT ACTCATTTGA TTTCATATAT ACCAGACTGT CAATGGTTAC
  1301     CTTAATCAGT GAGGCACCTA TCTCAGCGAT CTGTCTATTT CGTTCATCCA TAGTTGCCTG ACTCCCCGTC AAGTATATATA ACTCCCCGTC GTGTAGATAA CTACGATACG GAAGGGCTTA
```

Figure 17 (continued)

```
        GAATAGTCA CTTCCGTGAT AGAGTCGCTA GACAGATAAA GCAAGTAGGT ATCAACGAC TGAGGGCAG CACATCTATT GATGCTATGC CCTCCCGAAT
1401    CCATCTGCC CCAGTGCTGC AATGATACCG CGAGACCCAC GCTCACCGGC TCCAGATTTA TCAGCAATAA ACCAGCCAGC CGGAAGGGCC GAGCGCAGAA
        GGTAGACCGG GGTCACGACG TTACTATGGC GCTCTGGGTG CGAGTGGGCG CGAGTGGCCG AGTCGTTATT AGTCGTTATT TGGTCGGTCG GCCTTCCCGG CTCGCGTCTT
1501    GTGGTCCTGC AACTTTATCC GCCTCCATCC AGTCTATTAA TTGTTGCCGG GAAGCTAGAG TAAGTAGTTC GCCAGTTAAT AGTTTGCGCA ACGTTGTTGG
        CACCAGGACG TTGAAATAGG CGGAGGTAGG TCAGATAATT AACAACGGCC CTTCGATCTC ATTCATCAAG CGGTCAATTA TCAAACGCCT TGCAACAACC
1601    CATTGCTACA GGCATCGTGG TGTCACGCTC GTCGTTTGT ATGGCTTCAT TCAGCTCCGG TTCCCAACGA AGTCGAGGCC AAGGGTGCT AGTTCCGCTC AATCTACTAG GGGTACAAC
        GTAACGATGT CCGTAGCACC ACAGTCGAG CAGCAAACCA TACCGAAGTA AGTCGAGGCC AAGGGTGCT AGTTCCGCTC AATCTACTAG GGGTACAAC
1701    TGCAAAAAAG CGGTTAGCTC CTTCGGTCCT CCGATCGTTG TCAGAAGTAA GTTGGCCGCA GTGTTATCAC TCATGGTTAT GGCAGCACTG CATAATTCTC
        ACGTTTTTC GCCAATCGAG GAAGCCAGGA GGCTAGCAAC AGTCTTCATT CAACCGGCGT CACAATAGTG AGTACCAATA CCGTCGTGAC GTATTAAGAG
1801    TTACTGTCAT GCCATCCGTA AGATGCTTTT CTGTGACTGG TGACTACTCA ACCAAGTCAT TCTGAGAATA GTGTATGCGG CGACCGAGTT GCTCTTCCCC
        AATGACAGTA CGGTAGGCAT TCTACGAAAA GACACTGACC ACTGCATGAGT TGGTTCAGTA AGACTCTTAT CACATACGCC GCTGGCTCAA CGAGAACGGG
1901    GGCGTCAATA CGGGATAATA CCCGCCACA TAGCAGAACT TTAAAAGTGC TCATCATTGG AAAACGTTCT TCGGGGCGAA AACTCTCAAG GATCTTACCG
        CCCGAGTTAT GCCCTATTAT GGCGCGGTGT ATCGGTCTTGA AATTTTCACG AGTAGTAACC TTTTGCAAGA AGCCCCGCTT TTGAGAGTTC CTAGAATGGC
2001    CTGTTGAGAT CCAGTTCGAT GTAACCCACT CGTGCACCCA ACTGATCTTC AGCATCTTTT ACTTTCACCA GCGTTTCTGG GTGAGCAAAA ACAGGAGGC
        GACAACTCTA GGTCAAGCTA CATTGGGTGA GCACTGGGT TGACTAGAAG TCGTAGAAAA TGAAAGTGGT CGCAAAGACC CACTCGTTTT TGTCCTTCCG
2101    AAAATGCCGC AAAAAAGGGA ATAAGGGCGA CACGGAAATG TTGAATACTC ATACTCTTCC TTTTTCAATA TTTTTCAAGC ATTTATCAGG GTTATTGTCT
        TTTTACGGCG TTTTTTCCCT TATTCCCGCT GTGCCTTTAC AACTTATGAG TATGAGAAGG AAAAAGTTAT AATAACTTCG TAAATAGTCC CAATAACAGA
2201    CATGAGCGGA TACATATTTG TACATATTTA GAAAAATAAA CAAATAGGGG TTTCGCCCAC ATTTCCCCGA AAAGTGCCAC CTGACGTCTA AGAAACCATT
        GTACTCGCCT ATGTATAAAT TTACATAAAT CTTTTATTT GTTTATCCCC AAGGCGGGTG TAAAGGGGCT TTTCACGGTG GACTGCAGAT TCTTTGGTAA
2301    ATTATCATGA CATTACCCTA TAAAAATAGG CGTAAGCGG ATGCCGGGAG CAGACAAGCC TCTCGGCCGT CGTCAGGCGG CCTCTGACAC ATGCAGCTCC GGCTTAACTA
        TAATAGTACT GTAATTGAT ATTTTATCC GCATTCCG GCATATCC GTCTGTTGG CGGGAAAGC GCAGTCCCGC CAGTGCCGC AAGCCACTAC GGAGACTGTG TACGTCCAGG
2401    CGGAGACGGT CACAGGTTGT CTGTAAGCGG TACTGAGAGT ATGCCGGAGA ATGCCGTGAT CGGTGTGAAA TACCGCACAG ATGCCGTAAGG GCATCAGGCG CCATTCCCA
        GCCTCTGCCA GTGTCGAACA CTTCGCTAA ATGACTCTCA CGTGGTATAC GCCACACTTT TGCCCGGCT GCCACACTTT ATGGCGTGTC TCTTTTATGG CGTAGTCGC GGTAAGCGGT
2501    TGCGGCATCA GAGCAGATTG TACTCGAGAGT GGAAGGGCGA TGGTGCGGA CCTCTTCGCT ATTACGCCG ATTACGCCG AGGAAAGCGA TAATGCGGTC CCCTACACG AGTTCCGCCT AATTCAACCC
        ACGCCGTAGT CTCGTCTAAC ATGACTCTCA CCTTCCCGCT AGCCACGCCC TAATGCGGTC GGAGAAGCGA AGCCACTTC CCCTACACG AGTTCCGCCT AATTCAACCC
2601    TTCAGGCTGC GCAACTGTTG GGAAGGGCGA CCTTCCCGCT AGCCACGCCC TCGGTGCGGG AGCCACGCCC TAATGCGGTC GGAGAAGCGA GGGCATGTGC TCCAAGGCGA TTAAGTTGGG
        AAGTCCGACG CGTTGACAAC CCTTCCCGCT AGCCACGCCC TCGGTGCGGG AGCCACGCCC TAATGCGGTC GGAGAAGCGA GACCGGTTTC CCCTACACG AGTTCCGCCT AATTCAACCC
2701    TAACGCCAGG GTTTTCCCAG TCACGACGTT GTAAAACGAC GGCCAGTGAA TTGTAATACG ACTCACTATA
        ATTGCGGTCC CAAAGGGTC AGTGCTGCAA CATTTTGCTG CCGGTCACTT AACATTATGC TGAGTGATAT
```

METHOD FOR GENE IDENTIFICATION SIGNATURE (GIS) ANALYSIS

CROSS REFERENCE TO RELATED APPLICATIONS

This application is a divisional of U.S. Ser. No. 11/045,468, filed Jan. 31, 2005, which is a continuation-in-part of U.S. Ser. No. 10/664,234 filed Sep. 17, 2003, the whole content of these prior applications is herein incorporated by reference.

FIELD OF THE INVENTION

The present invention relates generally to the field of gene and transcript expression and specifically to a method for the serial analysis of a large number of transcripts by identification of a Gene Identification Signature (GIS) corresponding to defined regions within a transcript. Further, the present invention relates to a method of identification of protein binding sites, in particular transcription factor binding sites.

BACKGROUND OF THE INVENTION

One of the most important goals of the human genome project is to provide complete lists of genes for the genomes of human and model organisms. Complete genome annotation of genes relies on comprehensive transcriptome analysis by experimental and computational approaches. Ab initio predictions of genes must be validated by experimental data. An ideal solution is to clone all full-length transcripts and completely sequence them. This approach has gained recognition recently (Strausberg, R. L., et al., 1999, Science, 286: 455-457) and progress has been made (Jongeneel C. V., et al., 2003, Proc Natl Acad Sci USA. 100, 4702-4705). However, due to the complexity and immense volume of transcripts expressed in the various developmental stages of an organism's life cycle, complete sequencing analysis of all different transcriptomes still remains unrealistic.

To get around such a dilemma, a cDNA tagging strategy that obtains partial sequences that represent full transcripts has been developed and widely applied in determining genes and characterizing transcriptomes in the past decade.

In the expressed sequence tag (EST) approach, cDNA clones are sequenced from 5' and/or 3' ends (Adams, M., et al., 1991, Science, 252, 1651-1656). Each EST sequence read would generate on average a 500 bp tag per transcript. The number of same or overlapping ESTs would manifest the relative level of gene expression activity. Though ESTs are effective in identifying genes, it is prohibitively expensive to tag every transcript in a transcriptome. In practice, sequencing usually ceases after 10,000 or less ESTs are obtained from a cDNA library where millions of transcripts might be cloned.

To increase the efficiency in sequencing and counting large numbers of transcripts, Serial Analysis of Gene Expression (SAGE) ((Velculescu, V. E., et al., 1995, Science, 270, 484-487; Saha S, et al., 2002, Nature Biotechnology, 20, 508-12; U.S. Pat. Nos. 6,498,013; 6,383,743) and the recent Massively Parallel Signature Sequencing (MPSS) technique (Mao C., et al., 2000, Proc Natl Acad Sci USA, 97, 1665-1670; Brenner S, et al., 2000, Nature Biotechnology, 18, 630-634) were developed based on the fact that a short signature sequence (14-20 bp) of a transcript can be sufficiently specific to represent that gene.

Experimentally, short tags can be extracted from cDNA (one tag per transcript). Such short tags can be efficiently sequenced either by a concatenation tactic (as for SAGE) or by a hybridization-based methodology (as for MPSS). For example, in SAGE, multiple tags are concatenated into long DNA fragments and cloned for sequencing. Each SAGE sequence readout can usually reveal 20-30 SAGE tags. A modest SAGE sequencing effort of less than 10,000 reads will have significant coverage of a transcriptome. Transcript abundance is measured by simply counting the numerical frequency of the SAGE tags.

With the availability of many assembled genome sequences in public databases, the use of a short tag strategy for transcriptome characterization is becoming popular (Jongeneel et al., 2003, Proc. Natl. Acad. Sci. USA 100: 4702-4705). In theory, short DNA tags of about 20 bp can be specifically mapped to a single location within a complex mammalian genome and uniquely represent a transcript in the content of whole transcriptome. However, in reality, there still exist a large number of "ambiguous" SAGE tags (14-21 bp) and MPSS tags (17 bp) that have multiple locations in a genome, and may be shared by many genes. Limited by the availability of type II restriction enzymes that can cut longer than 21 bp, the SAGE method currently cannot generate any longer tags to improve specificity.

Further, SAGE and MPSS methods only produce a single signature per transcript within the gene. In view of the "internal" nature of the tag in a transcript, these methods provide only limited positional and structural information.

Therefore, despite their usefulness in enhancing sequencing efficiency, the utility of methods such as SAGE or MPSS is severely undermined by their lack of specificity and consequent inconclusiveness.

There is a need in the art for more efficient methods which retain the sequencing efficiency of tag-based methods, and at the same time improves upon the use of the tagging strategy for transcriptome characterization and to facilitate the annotation of genomes.

SUMMARY OF THE INVENTION

The present invention solves the problems mentioned above by providing two covalently-linked tags (a ditag) per nucleic acid molecule, thereby increasing the specificity of the tags in representing a nucleic acid molecule (e.g. a gene). The two tags are extracted from the 5' and 3' ends of the same nucleic acid molecule, and therefore ditags are more informative in reflecting the structure of the nucleic acid molecules than single tags. Critically, the invention provides a method to link the 5' and 3' tags of the same nucleic acid molecule into a single ditag unit. Therefore, the pairs of 5' and 3' tags that represent the nucleic acid molecule can be easily recognized by simple sequencing analysis. The invention can be used for the identification of new genes, for the measure of transcript abundance in transcriptomes, for the annotation of genome sequences and at the same time enhancing sequencing efficiency.

In particular, the invention provides an isolated oligonucleotide comprising at least one ditag, wherein the ditag comprises two joined first and second sequence tags, wherein the first tag comprises the 5'-terminus sequence and the second tag comprises the 3'-terminus sequence of a nucleic acid molecule.

The oligonucleotide of the invention, further comprises at least two adapters flanking the ditag, wherein each adapter comprises at least one restriction site. In particular, each adapter comprises at least: a first restriction site proximal to the tag which is an asymmetric recognition site (for example, a homing endonuclease recognition site, or a type II, or a type III recognition site) and at least a second restriction site. The second or further restriction site may be any restriction site known in the art may be used. For example, BamHI. Also, any asymmetric restriction site different from the first restriction site may be used. The recognition site for this enzyme however must be absent from the vector backbone after formation of the ditag.

The nucleic acid molecule may be the full-length sequence of a gene or a fragment thereof. It may also be a fragment of nucleic acid that does not contain a gene. For example, RNA, mRNA, genomic DNA, full-length cDNA or cDNA.

The ditag may vary in nucleotide number. According to one embodiment, it is obtained by splicing the 5' terminus and the 3' terminus of a nucleic acid molecule in presence of at least one restriction enzyme and the size of the sequence tags is determined by the restriction enzyme used. Accordingly, the number of nucleotides of the ditag can vary according to the restriction enzyme used.

When MmeI is used, this enzyme recognizes a sequence inside each of the two adapters that flank the nucleic acid molecule which one intends to reduce, but cuts inside the nucleic acid molecule forming a tag comprising 17-21 nucleotides. Two such tags may be additionally processed by blunting and ligation to form a ditag comprising 34-38 nucleotides. The ditag is hence obtained by splicing together the 5' terminus and the 3' terminus of the same nucleic acid molecule.

The ditag of the invention can be of any size, preferably 12-60 bp.

The oligonucleotide may comprise a concatemer of ditags, for example 1 to 1000 ditags.

The invention also provides a vector comprising the oligonucleotide of the invention. In particular, the vector comprises at least a nucleic acid molecule and at least two adapters flanking the nucleic acid molecule, wherein each adapter comprises at least: a first restriction site which is a asymmetric restriction site (asymmetric restriction site is, for example, a homing endonuclease recognition site, or a type II or type III recognition site) and at least a second restriction site (for example Bam HI), and the backbone of the vector does not comprise the asymmetric restriction site and the second or further restriction site. A preferable, asymmetric restriction site is the type II restriction site MmeI.

The invention also provides a vector having the sequence indicated in SEQ ID NO:18.

The invention further provides a cDNA library, wherein every cDNA clone comprises the at least one oligonucleotide of the invention.

According to another aspect, the invention also provides a method for preparing at least one oligonucleotide comprising at least one ditag comprising:
  producing at least one nucleic acid molecule;
  isolating the 5' terminus and the 3' terminus of the nucleic acid molecule or fragment hereof; and
  linking the 5' terminus and 3' terminus to create the at least one ditag.

In particular, it is provided a method for preparing at least one oligonucletide comprising at least one ditag comprising:
  producing at least one nucleic acid molecule flanked by two adapters;
  isolating the 5' terminus and the 3' terminus of the nucleic acid molecule; and
  linking the 5' terminus and 3' terminus to create the at least one oligonucleotide comprising at least one ditag flanked by the two adapters.

The nucleic acid molecule desired to be reduced in form of a ditag may be a full nucleic acid molecule or a portion inside the nucleic acid molecule.

The nucleic acid molecule may correspond to the full-length of a gene or fragment thereof.

The method may further comprise the step of determining the nucleotide sequence of the at least one ditag to detect gene expression.

According to a further aspect, the method of the invention may further comprise the steps of:
  determining the sequence of the at least one ditag; and
  comparing the ditag nucleotide sequence to a database comprising genomic sequences whereby matching 5' and 3' termini sequences are identified.

According to a particular embodiment, the invention provides a method comprising:
  producing at least one nucleic acid molecule, preferably a full-length cDNA, flanked by two adapters, wherein each adapter comprises at least one restriction site; splicing the 5' terminus and the 3' terminus of the nucleic acid molecule to produce at least one ditag by adding at least one restriction enzyme recognizing the recognition sites.

Preferably, each adapter comprises at least: a first restriction site which is an asymmetric restriction site and a second restriction site.

As restriction enzyme, any useful enzyme can be used. For example, a restriction enzyme recognizing two asymmetric recognition sites.

Asymmetric recognition site can be: i) homing endonuclease asymmetric recognition site sequences or ii) restriction endonuclease asymmetric cleavage sites sequences recognizable by type II or type III restriction enzymes.

According to a particular embodiment, the splicing step is carried out by using MmeI (together with T4 DNA polymerase and T4 DNA ligase), and the ditag of 34-38 nucleotides, flanked by two adapters, is thereby produced.

According to a further aspect, the ditag of any embodiment of the invention can be linked to other ditags to produce concatemers of ditags. For example, 1 to 1000 ditags.

According to another further aspect, it is provided a method for genome mapping, comprising:
  preparing at least one oligonucleotide comprising at least one ditag, the ditag comprising two joined first and second sequence tags, wherein the first tag comprises the 5'-terminus sequence and the second tag comprises the 3'-terminus sequence of a nucleic acid molecule, the nucleic acid molecule corresponding to the full-length of a gene or fragment thereof;
  mapping each of the two tags of the at least one ditag on the genome; and
  defining the structural region of the corresponding gene on the genome map.

According to a still another aspect, the invention provides a method of gene discovery comprising:
  preparing at least one oligonucleotide comprising at least one ditag, the ditag comprising two joined first and second sequence tags, wherein the first tag comprises the 5'-terminus sequence and the second tag comprises the 3'-terminus sequence of a nucleic acid molecule, the nucleic acid molecule corresponding to the full-length of a gene or fragment thereof;
  comparing the obtained at least one ditag with a genome map and/or a gene database;
  if the 5' and 3' termini tags of a ditag are matched to the genome sequence but not in known gene databases, then the detected ditags may represent new genes in the given genomes.

Such ditags can directly guide the process of recovering the full-length nucleic acid molecule corresponding to the newly identified genes.

It is also an aspect of the invention a method for recovering the full-length cDNA of new and/or other interesting genes comprising:

preparing, from a full-length cDNA library, at least one oligonucleotide comprising at least one ditag, the ditag comprising two joined first and second sequence tags, wherein the first tag comprises the 5'-terminus sequence and the second tag comprises the 3'-terminus sequence of a full-length cDNA library;

sequencing the obtained oligonucletide ditag, preferably a large number of the obtained ditags;

determining the ditag of interest (for example, based on biological aspects); and recovering the full-length cDNA corresponding to the ditag of interest from the parental full-length cDNA library.

This method may be carried out according to any standard technology known in the art, for example, by PCR or screening using probes. The PCR primers and the probes sequences are prepared based on the information of the sequence of the ditag.

Further, the invention also provides a method for quantifying the transcriptional activity of a gene comprising:

preparing, from a full-length cDNA library, at least one oligonucleotide comprising at least one ditag, the ditag comprising two joined first and second sequence tags, wherein the first tag comprises the 5'-terminus sequence and the second tag comprises the 3'-terminus sequence of a full-length cDNA;

sequencing the obtained oligonucleotide ditag, preferably a large number of the obtained ditags;

determining the frequency of the sequenced ditag which corresponds to the transcriptional activity of the gene.

According to a further embodiment, the invention provides a method of identifying at least a nucleic acid molecule fragment to which a protein of interest binds, comprising:

(i) preparing at least one nucleic acid molecule fragment to which a protein binds;

(ii) isolating the 5' terminus and the 3' terminus of the nucleic acid fragment(s) and linking the 5' terminus and 3' terminus to create the at least one ditag;

(iii) sequencing the ditag; and (iv) mapping the ditag sequence(s) to the genome.

In particular, the method according to this embodiment may be a method for the identification and/or discovery of protein binding site(s), more in particular, transcription factor binding site(s) (TFBSs).

The nucleic acid fragment to which a protein of interest binds may be any nucleic acid fragment comprising a region to which a protein of interest binds, for example, trans-acting protein(s) binding site. In particular, the nucleic acid molecule fragment of the invention is preferably a genomic DNA fragment enriched for transcription factor binding site(s) (TFBSs).

In this embodiment, before carrying out step (ii), the nucleic acid molecule fragment to which a protein binds is preferably inserted into a vector. The vector may be any vector suitable for the purpose of the present embodiment. In particular, the vector comprises two regions (or motifs) flanking the nucleic acid molecule fragment which is to be inserted into the vector. Each region (motif) comprises at least: a first restriction site which is an asymmetric restriction site and/or at least a second restriction site, and wherein the remainder of the backbone of the vector does not comprise the asymmetric restriction site and/or the second restriction site. The asymmetric recognition sites may be restriction endonuclease asymmetric cleavage site sequences recognizable by type II or type III restriction enzymes or homing endonucleases as described in other embodiments of the present invention. In particular, the type II restriction site is MmeI. According to a particular aspect, the vector of the invention has the sequence of SEQ ID NO:22.

The ditags may be joined to form a concatemer of ditags. The concatemer may comprise 1-1000 ditags.

According to a particular aspect, in the method of this embodiment the nucleic acid molecule fragment of step (i) is isolated from a living cell by: (a) cross-linking DNA binding protein in the living cell to genomic DNA of the living cell, thereby producing DNA binding protein cross-linked to genomic DNA; (b) generating DNA fragments of the genomic DNA cross-linked to DNA binding protein in (a), thereby producing a DNA/protein complex comprising DNA fragments to which the DNA binding protein is bound; (c) removing the DNA fragment to which the protein of interest is bound from the complex produced in (b); and (d) isolating the DNA fragment identified in (c) from the protein of interest. The DNA/protein complex may be isolated by antibody-mediated immunoprecipitation.

In particular, the nucleic acid molecule fragment(s) may be isolated by chromatin immunoprecipitation. Alternatively, the nucleic acid molecule fragment(s) may be isolated by incorporating a photoactivable moiety into the DNA and/or the protein of interest and isolation of DNA/protein complex by antibody-mediated precipitation or by affinity-mediated technique. Examples of such affinity-based techniques include streptavidin/biotin, Glutathione-S-transferase/glutatathione matrix, maltose-binding protein/amylose matrix interactions.

According to a particular aspect of this embodiment, the method of identifying at least one DNA fragment to which a protein of interest bind comprises: (a) cross-linking DNA binding protein(s) in living cell(s) to genomic DNA of the living cell, thereby producing DNA binding protein cross-linked to genomic DNA; (b) generating DNA fragments of the genomic DNA cross-linked to DNA binding protein in (a), thereby producing a DNA/protein complex comprising DNA fragments to which the DNA binding protein is bound; (c) removing the DNA fragment to which the protein of interest is bound from the complex produced in (b); (d) isolating the DNA fragment(s) identified in (c) from the protein of interest; (e) inserting the isolated DNA fragment(s) into a vector; (f) isolating the 5' terminus and the 3' terminus of the nucleic acid fragment(s) inserted into the vector and linking the 5' terminus and 3' terminus to create the at least one ditag; (g) sequencing the ditag; and (h) mapping the ditag sequence(s) to the genome.

In the step (a) formaldehyde may be added to living cells; and in step (b) crude extracts of the fixed cells are prepared, and sonicated to shear the chromatin.

In particular, the protein of interest binds to the nucleic acid molecule fragment(s) at a consensus binding site, which may be determined or identified by the region of genomic DNA encompassed (or spanned) by the two signatures of the ditag.

Further, the present invention provides a vector comprising at least one ditag, wherein the ditag comprises two joined first and second sequence tags, and wherein the first tag includes a 5'-terminus sequence and a second tag comprises the 3'-terminus sequence of a nucleic acid molecule fragment, and wherein the nucleic acid molecule fragment is enriched for transcription factor binding sites (TFBSs). In particular, in the vector the ditag may be flanked at each side by a region (or motif) comprising at least: a first restriction site which is an asymmetric restriction site and/or at least a second restriction site, and these flanking regions (also called motifs) are incorporated into the vector backbone. The asymmetric restriction site may be a type II restriction site or a type III restriction site or a restriction site recognised by a homing endonuclease. In particular, the vector, before the introduction of the ditag, has the nucleotide sequence of SEQ ID NO:22 (see also FIG. 17).

BRIEF DESCRIPTION OF THE FIGURES

FIG. 10 shows the double strand nucleotide sequence of pGIS1. The region between the restriction sites Not I and Sal I is the stuffer fragment that is removed during cloning. It is highlighted in bold and italic type. The single strand nucleotide sequence is also reported as SEQ ID NO:18. The region representing the stuffer fragment is between nucleotide 15 to 704 (both nucleotides included).

FIG. 17 shows the sequence of pGIS3 (see also SEQ ID NO:22).

DETAILED DESCRIPTION OF THE INVENTION

Definitions

Figure 1:
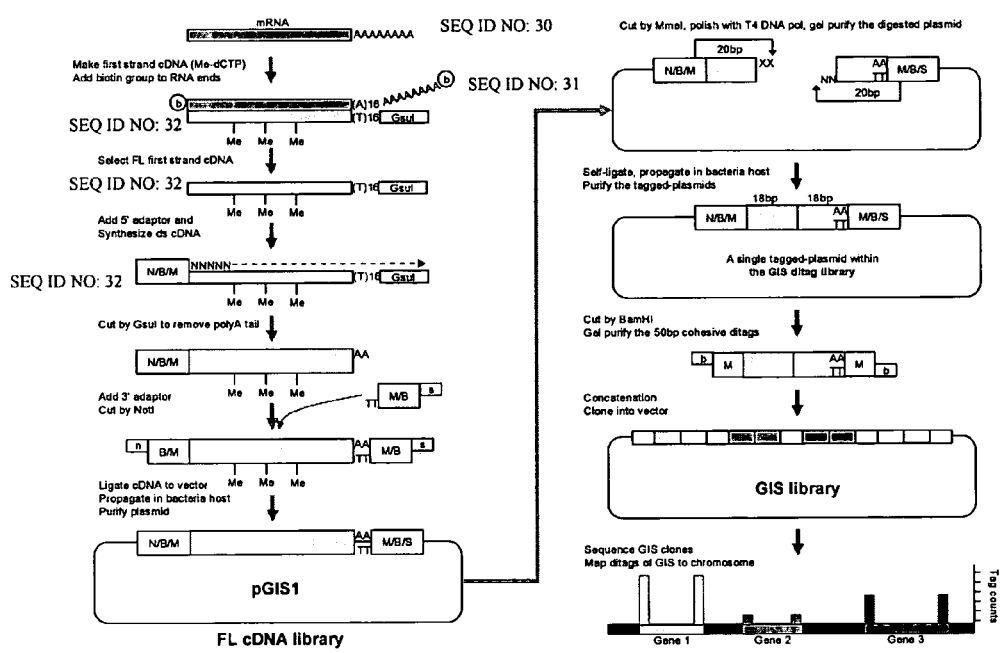
FIG. 1 shows the GIS analysis experimental workflow (bacterial transformation approach). In the figure, the letters N, B, M, and S either in capital or small letters denotes the recognition sites for the restriction enzymes Not I, Bam HI, Mme I and Sal I, respectively. The text "Me" represents methylation of the newly-synthesized first-strand cDNA. When applying this procedure to other DNA fragments, the construction of the full-length cDNA (flcDNA) library in pGIS1 is replaced by an alternative library, for example that in pGIS3 as shown in FIG. 13 for ChIP-GIS. Subsequent steps in the procedure would be identical.

A non-exhaustive list of definitions used in the present application is as follows:

Annotation: The description of the exact location, extent and function of sequence elements within a DNA or protein sequence.

Ditag: See GIS ditag

Enhancers: DNA regions which are usually rich in transcription factor binding sites and/or repeats. They enhance transcription of the responsive promoter irrespective of their orientation or position. Enhancers bind to the class of transcription factors called activators.

Full length cDNA: Full length cDNA contains an entire open reading frame (ORF), and reaches up to the transcriptional initiation point and contains the 5'-untranslated region (5'-UTR).

Genome: The total DNA of an organism which is present in nearly all cells. The human genome contains approximately 3 billion base pairs.

GIS ditag: A short (usually 34-38 bp) DNA fragment derived from covalent linkage of the 5' and 3' terminal tags or signatures (see Signature) of a contiguous DNA region (in this case, a ChIP-enriched fragment).

Locus Control Regions (LCRs): These act to open up a chromatin domain necessary for active transcription and sometimes act as enhancers of transcription themselves.

Matrix Attachment Regions (MARs): Also called Scaffold/Matrix Attachment Regions (S/MARs). Sequence regions that are responsible for the attachment of genomic DNA to the nuclear matrix or scaffold.

Promoters: DNA regions which are rich in transcription factor binding sites. A promoter is used to initiate and regulate transcription of a gene. Promoters are similar to enhancers, but also contain elements that allow specific initiation of transcription (promoters bind basal transcription factors). Most genes in higher eukaryotes are transcribed from polymerase II dependent promoters.

Signature: In the context of this report, a signature refers to either the 5'- or 3'-most terminal DNA sequence (usually 18-20 bp) derived from any contiguous DNA region.

Silencers: DNA regions that are rich in transcription factor binding sites. They suppress transcription of the responsive promoter. Silencers bind to the class of transcription factors called repressors.

Transcription Factor (TF): A protein that binds to specific non-coding regulatory regions in the genome, and regulates gene expression. TFs can be divided into three broad categories: basal transcription factors, which are members of the basal transcription complex, and are involved directly in the recruitment of RNA polymerase to the transcription initiation site; activators, which increase the rate of, or allow the formation of the basal transcription complex; and repressors, which decrease or prevent the formation of the basal transcription complex. See also Promoters, Enhancers, and Silencers.

Transcription factor binding site (TFBS): Short stretches (usually 10-20 bp) of DNA, sufficiently conserved to allow specific recognition by the corresponding transcription factor.

Transcriptome: The complete collection of RNAs that are transcribed from a genome. This includes all the mRNAs coding for the proteome as well as all RNAs not coding for proteins (e.g. ribosomal RNAs).

Introduction

The present invention provides a Gene Identification Signatures (GIS) and a GIS analysis method: useful, for example, for the rapid analysis of numerous transcripts in order to identify the overall pattern of transcript expression (transcriptome), for the selection and/or construction of cDNA and full-length cDNAs, tag sequencing, gene discovery, genome mapping and annotation. In general, the GIS and GIS analysis method according to the invention greatly facilitates the collection of gene information by experimental approach.

For the purpose of the present application, GIS means a ditag (also indicated as GIS ditag) or an oligonucleotide comprising at least one ditag, wherein the ditag comprises the 5' terminus (or end region) and the 3' terminus (or end region) of a nucleic acid molecule, which it is desired to reduce, "shrink" or represent.

The ditag is shorter than the original nucleic acid molecule from which it originates or which it represents. Preferably, the ditag must be much shorter than the original nucleic acid molecule. As consequence of the "shrinking", the ditag essentially comprises the 5' end region (also indicated as 5' tag) and 3' end region (also indicated as 3' tag) of the original nucleic acid molecule. Hence, the portion of the original nucleic acid molecule which is between or inside the 5' tag and 3' tag is not included in the ditag. The ditag according to the invention retains the most informative features of the original nucleic acid molecule, viz. the start and the end signatures of the nucleic acid. It is thereby also more specific and accurate than SAGE or MPSS methods in characterizing transcriptomes and defining gene structure by mapping the GIS tags to genome sequences.

Accordingly, the invention provides an isolated oligonucleotide comprising at least one ditag, wherein the ditag comprises two joined first and second sequence tags, wherein the first tag comprises the 5'-terminus sequence and the second tag comprises the 3'-terminus sequence of a nucleic acid molecule or fragment thereof.

Figure 2:
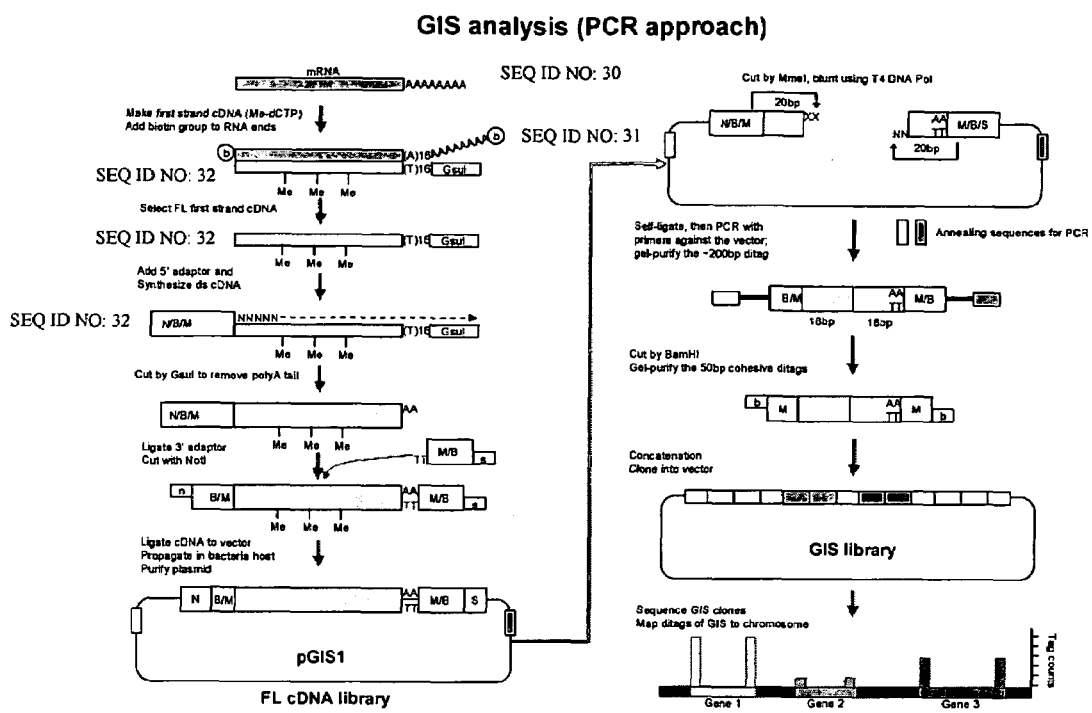
FIG. 2 shows the GIS analysis experimental workflow (PCR-based approach). In the figure, the letters N, B, M, S either in capital or small letters denotes the recognition sites for the restriction enzymes Not I, Bam HI, Mme I and Sal I, respectively. The text "Me" represents methylation of the newly-synthesized first-strand cDNA.

The oligonucleotide of the invention may further comprise two adapters flanking the ditag, wherein each adapter comprises at least one restriction site (see FIG. 1 and FIG. 2). In particular, each adapter comprises at least: a first restriction site which is an asymmetric restriction site and at least a second adjacent restriction site. Therefore, the number of restriction sites present in each adapter may be two or more. Examples of asymmetric restriction sites are homing endonuclease asymmetric recognition sites, and type II (or class III) recognition sites. A list of possible asymmetric restriction sites and corresponding restriction enzymes recognizing such asymmetric sites is reported below. Example of second and further restriction sites may be for example BamHI. This second restriction site is for the purpose of subsequent isolation of a pool of ditags that can then be ligated together to form concatemers.

The original nucleic acid molecule that one intends to reduce (to shrink) may be any natural, any modified or any synthetic nucleic acid molecule. It can also be of any size. The nucleic acid molecule can be a gene (the full-length of a gene) or a fragment thereof. The nucleic acid may be RNA, mRNA, genomic DNA, full-length cDNA, or cDNA or a fragment thereof.

The ditag can also be fully chemically synthesized by comprising the 5' end and 3' end of a nucleic acid molecule which the ditag intends to represent.

The molecule that one intends to reduce may also be a portion or fragment inside a nucleic acid molecule. Accordingly, it is possible to use restriction enzymes recognizing restrictions sites flanking the region which is intended to be reduced. The desired restriction sites may be placed into the appropriate position during the preparation of the nucleic acid molecule, for example a cDNA or full-length cDNA.

According to a particular aspect, the nucleic acid desired to be reduced is a full-length cDNA. Full-length cDNA can be prepared according to any method known in the art. See for example, the cap-trapper approach, for example Carninci et al., 1996, Genomics, Vol. 37, 327-336; U.S. Pat. No. 6,143,528; Edery et al., 1995, Mol. Cell. Biol., Vol. 15, No. 6, 3363-3371.

Those of skill in the art will know other capture systems, for example, those based on biotin/streptavidin, digoxigenin/anti-digoxigenin for isolation of the full-length cDNAs can be used.

The ditag can be prepared according to any technique known in the art. For example, the original nucleic acid molecule may be cut through any chemical reaction and the obtained 5' and 3' termini ligated to create the ditag.

The nucleic acid molecule which is intended to be reduced, which is preferably prepared comprising two adapters flanking the molecule, may be inserted into a vector. In a particular realisation, each adapter comprises at least one restriction site, preferably comprises at least a first restriction site comprising an asymmetric restriction site and a second restriction site. Accordingly, in the vector used, it is important that the backbone of the vector does not comprise the restriction site or sites present in the adapters.

Accordingly, a library of nucleic acid molecule (for example, a library of full-length cDNAs) is prepared.

Preferably, the nucleic acid molecule is spliced into a ditag or oligonucleotide comprising a ditag by using restriction enzymes which recognize restriction sites flanking the nucleic acid molecule to be reduced. Accordingly, the recognition sites are placed upstream of the 5' terminus and downstream of the 3' terminus of the nucleic acid molecule or fragment thereof desired to be reduced (preferably into the adapters). Accordingly, the oligonucleotide obtained by splicing comprises two adapters flanking the ditag. Each adapter comprising at least one restriction site. Preferably, comprising at least one first restriction site which is an asymmetric site (for example a type II restriction site, like MmeI, or type III restriction site, like EcoP15I) and at least a second restriction site (any known restriction site may be used, for example BamHI).

The 5' tag and 3' tag forming the ditag may have the same or different size. Preferably, they have the same number of nucleotides.

The ditag can be of any size, but needs to be meaningful and advantageous over the size of the parental sequence from which it is derived. The preferred size of a tag or ditag is determined by genome complexity. For a bacterial genome a tag from about 8 bp to about 16 bp may be sufficient whereas for a complex genome like the human genome, a 16-20 bp tag (or in other words a 32-40 bp ditag) may be considered. In general, the size of the ditag is from about 12-60 bp.

For the purpose of the present application, the terms 5'-terminus, 5'-end and 5'-tag are equivalent to each other and can be used interchangeably. In the same way, the terms 3'-terminus, 3'-end and 3'-tag are equivalent to each other and can be used interchangeably. In an original nucleic acid molecule or portion inside a nucleic acid molecule that one intends to reduce or represent, each of the 5'-end and 3'-end represents a region or portion most closer to the extremity and most far from the middle region of the molecule.

According to one aspect, the 5'-tag and 3'-tag comprised in the ditag are the regions of the molecule cleaved by a restriction enzyme most closer to the 5'-end and 3'-end, respectively, of the nucleic acid molecule or portion thereof which is intended to be reduced or represented. Accordingly, the size of the ditag can be determined by the restriction enzyme or enzymes used. The invention, therefore, relates to an oligonucleotide comprising at least one ditag, wherein the ditag is obtained by splicing the 5' terminus and the 3' terminus of the nucleic acid molecule in the presence of at least one restriction enzyme, which recognizes the restriction sizes flanking the nucleic acid molecule. Accordingly, the size of the sequence tags is determined by the restriction enzyme used.

When preparing the nucleic acid molecule, for example a full-length cDNA, desired restriction sites flanking the 5'-end and 3'-end of the region which is intended to be reduced or represented are inserted. An example of construction of a full-length cDNA by insertion of desired restriction sites flanking the 5'-end and 3-end is shown in FIG. 1 and FIG. 2. A full-length cDNA library is then prepared, following which a GIS ditag library is subsequently prepared.

As an example, a restriction enzyme recognizing an asymmetric restriction site can be used for the purpose of the preparation of the ditag according to the invention. In particular a type II enzyme, for example MmeI, or a type III enzyme, for example EcoP15I.

As an example, asymmetric sites can be introduced. Asymmetric site sequences useful for the purpose of the present invention are: i) two homing endonuclease asymmetric recognition site sequences or ii) restriction endonuclease asymmetric cleavage sites sequences recognizable by type II restriction enzymes. iii) restriction endonuclease asymmetric cleavage sites sequences recognizable by type III restriction enzymes Homing endonucleases are sold and described by New England Biolabs, Inc.; a description of the asymmetric site sequences is also available in the New England Biolabs Catalog. These homing endonuclease asymmetric recognition site sequences are from 18 to 39 bp. However, in the present invention the recognition site sequences are not limited to those sequences nor to these sizes. Preferably, the restriction homing endonucleases capable of cutting the asymmetric site sequences are selected from the group consisting of: I-CeuI, PI-SceI, PI-PspI and I-SceI. The list mentioned above however is not exhaustive. Other homing endonucleases known in the art and those which may be later discovered are included in the scope of the present invention.

Examples of type II restriction enzymes include:
AarI, AceIII, AloI, BaeI, Bbr7I, BbvI, BbvII, BccI, Bce83I, BceAI, BcefI, BcgI, BciVI, BfiI, BinI, BplI, BsaXI, BscAI, BseMII, BseRI, BsgI, BsmI, BsmAI, BsmFI, Bsp24I, BspCNI, BspMI, BsrI, BsrDI, BstF5I, BtgZI, BtsI, CjeI, CjePI, EciI, Eco31I, Eco57I, Eco57MI, Esp3I, FalI, FauI, FokI, GsuI, HaeIV, HgaI, Hin4I, HphI, HpyAV, Ksp632I, MboII, MlyI, MmeI, MnlI, PleI, PpiI, PsrI, RleAI, SapI, SfaNI, SspD5I, Sth132I, StsI, TaqII, TspDTI, TspGWI, TspRI and Tth111II (the list in the web site of Rebase Enzymes®: rebase.neb.com; see also Szybalski, W., 1985, Gene, 40:169). The list mentioned above however is not exhaustive. Other type II enzymes known in the art and those which may be later discovered are included in the scope of the present invention.

Examples of recognition sites and cleavage sites of several class II restriction enzymes are (into parenthesis are the recognition site and the cleavage site): BbvI (GCAGC 8/12), HgaI (GACGC 5/10), BsmFI (GGGAC 10/14) SfaNI (GCATC 5/9), and Bsp I (ACCTGC 4/8).

Examples of type III restriction enzymes are given below.

The ditag of the invention can conveniently be ligated or joined in order to form concatemers of ditag. Accordingly, the invention relates to an oligonucleotide comprising 1 to 1000 ditags, in particular 1 to 200, more in particular 8 to 20 ditags. When ditags are concatemerized, a higher yield of information is achieved because the oligonucleotide, vector or clone comprises more ditags. Hence, the concatenation of ditags allows an efficient analysis of the nucleic acid molecules, like full-length cDNAs, in a serial manner by sequencing multiple ditags within a single vector or clone.

The oligonucleotide, ditag or concatemers of ditags can be inserted into a vector either before or after concatemerization.

According to one aspect, the oligonucleotide comprising the ditag is amplified. For example, by using PCR or any other known amplification methods. Accordingly, suitable PCR primers corresponding to specific regions inside the vector are used. Such regions flank the oligonucleotide comprising the ditag and adapters. PCR can be performed directly on the ligation (self-circularization) reaction to obtain short (for example 200 bp) PCR products (see the PCR approach in FIG. 2). These PCR products that contain the required GIS ditags will then be cut with an enzyme recognizing the at least second restriction site (inside the adapters) to generate the required short cohesive ditags. As restriction enzyme recognizing the second or further restriction site, BamHI can for example be used, and cohesive ditags of 50 bp are generated. The advantage of this amplification step is that of generating GIS ditags circumventing the need to produce a GIS ditag library amplification, which can be avoided by not transforming the self-circularized tagged plasmids. The amplified oligonucleotide can then subsequently be excised from the vector (in this example, by digestion with BamHI) and concatenated in long stretches of DNA or RNA for subsequent cloning and sequencing analysis (see FIG. 1 and FIG. 2).

As a particular aspect, the invention discloses a cDNA library wherein the oligonucleotide comprises at least one ditag, and wherein the ditag comprises 34-38 nucleotides and is obtained by splicing nucleotides from the 5' terminus and nucleotides from the 3' terminus of a full-length cDNA or fragment thereof.

The ditag library according to the invention is representative of the library comprising the original nucleic acid molecules. For example, when the library comprising the nucleic acid molecules is a full-length cDNA library, the ditag library is representative of the full-length ditag library. Each ditag clone comprises sufficient information characterizing the specific full-length clone. More important, the ditag of the invention comprises the 5'-end and 3'-end of the original full-length cDNA. Hence, the ditag is representative of the structure of the full-length cDNA.

Accordingly, it is sufficient to sequence and analyze the ditag clones of the ditag library. In case a ditag of interest is found, the corresponding full-length cDNA can be selected and prepared from the full-length cDNA library, for example by PCR or directly from target RNA samples by RT-PCR.

The invention provides a method for the preparation of at least one oligonucleotide comprising at least one ditag comprising:
  producing at least one nucleic acid molecule;
  isolating the 5' terminus and the 3' terminus of the nucleic acid molecule or fragment thereof;
  linking the 5' terminus and 3' terminus to create the at least one ditag.

In particular, the invention provides a method for preparing at least one oligonucleotide comprising at least one ditag comprising:
  producing at least one nucleic acid molecule flanked by two adapters;
  isolating the 5' terminus and the 3' terminus of the nucleic acid molecule; and
  linking the 5' terminus and 3' terminus to create the at least one oligonucleotide comprising at least one ditag flanked by the two adapters.

The method further comprising including the oligonucleotide comprising the at least one ditag flanked by the adapters into a vector.

The nucleic acid molecule which is intended to shrink or represent may be RNA, mRNA, genomic DNA, full-length cDNA, or cDNA.

The nucleic acid molecule may be the full-length sequence of a gene or a fragment thereof.

The method of the invention may further comprise the step of determining the nucleotide sequence of the at least one ditag to detect gene expression.

The method may further comprise the steps of: determining the sequence of the at least one ditag; and comparing the ditag nucleotide sequence to a database comprising genomic sequences whereby matching 5' and 3' termini sequences are identified.

More in particular, the invention relates to a method comprising:
  producing at least one nucleic acid molecule, for example a full-length cDNA, flanked by two adapters, wherein each adapter comprises at least one restriction; tk
  splicing the 5' terminus and the 3' terminus of the nucleic acid molecule or fragment thereof to produce at least one ditag by adding at least one restriction enzyme recognizing the recognition sites.

Any recognition site known in the art may be used. Restriction enzyme recognizing at least one recognition site within the nucleic acid molecule and which can be used will be evident to those skilled in the art (see for example, Current Protocols in Molecular Biology, Vol. 2, 1995, Ed. Ausubel, et al., Greene Publish. Assoc. & Wiley Interscience, Unit 3.1.15; New England Biolabs Catalog, 1995).

For example, the two recognition sites may be asymmetric recognition sites:

The asymmetric recognition site are: i) homing endonuclease asymmetric recognition site sequences or ii) restriction endonuclease asymmetric cleavage sites sequences recognizable by type II or type III restriction enzymes.

The type II restriction enzyme is selected from the group consisting of AarI, AceIII, AloI, BaeI, Bbr7I, BbvI, BbvII, BccI, Bce83I, BceAI, BcefI, BcgI, BciVI, BfiI, BinI, BplI, BsaXI, BscAI, BseMII, BseRI, BsgI, BsmI, BsmAI, BsmFI, Bsp24I, BspCNI, BspMI, BsrI, BsrDI, BstF5I, BtgZI, BtsI, CjeI, CjePI, EciI, Eco31I, Eco57I, Eco57MI, Esp3I, FalI, FauI, FokI, GsuI, HaeIV, HgaI, Hin4I, HphI, HpyAV, Ksp632I, MboII, MlyI, MmeI, MnlI, PleI, PpiI, PsrI, RleAI, SapI, SfaNI, SspD5I, Sth132I, StsI, TaqII, TspDTI, TspGWI, TspRI and Tth111II (see the list in the web site of Rebase Enzymes®: rebase.neb.com; see also Szybalski, W., 1985, Gene, 40:169; and). The list mentioned above however is not exhaustive. Other type II enzymes known in the art and those which may be later discovered are included in the scope of the present invention.

The enzyme recognizing the homing endonuclease asymmetric restriction site is selected from the group consisting of: I-CeuI, PI-SceI, PI-PspI and I-SceI. The list mentioned above however is not exhaustive. Other homing endonucleases known in the art and those which may be later discovered are included in the scope of the present invention.

Examples of type III restriction enzymes are given below.

A particularly preferred tagging enzyme, according to the invention, is an enzyme which cleaves 20/18 nucleotides 3' of its recognition site forming 3' overhanging ends, such as MmeI.

Artificial restriction endonucleases can also be used. These endonucleases may be prepared by protein engineering. For example, the endonuclease FokI has been engineered by insertions so that it cleaves one nucleotide further away from its recognition site on both strands of the DNA substrates. See Li and Chandrasegaran, Proc. Nat. Acad. Sciences USA 90:2764-8, 1993. Such techniques can be applied to prepare restriction endonucleases with desirable recognition sequences and desirable distances from recognition site to cleavage site.

The method further comprises producing concatemers of ditag. The concatemers may be generally about 1 to 1000 ditags, in particular 1 to 200 ditags, more in particular 8 to 20 ditags. While these are preferred concatemers, it will be apparent that the number of ditags which can be concatenated depends on the length of the individual tags and can be readily determined by those of skilled in the art without undue experimentation. After formation of concatemers, multiple tags may be cloned into a vector for sequence analysis, or ditags or concatemers can be directly sequenced without cloning by methods known to those of skill in the art.

The ditags present in a particular clone can be sequenced by standard methods (see for example, Current Protocols in Molecular Biology, supra, Unit 7) either manually or using automated methods.

As described above, the method comprises introducing the oligonucleotide comprising the at least one ditag in a vector.

With the term vector or recombinant vector it is intended a plasmid, virus or other vehicle known in the art that has been manipulated by insertion or incorporation of the ditag genetic sequences. Such vectors contain a promoter sequence which facilitates the efficient transcription. The vector typically contains an origin of replication, a promoter, as well as specific genes which allow phenotypic selection of the transformed cells. Vectors suitable for use in the present invention include for example, pBlueScript (Stratagene, La Jolla, Calif.); pBC, pZErO-1 (Invitrogen, Carlsbad, Calif.) (see FIG. 8) and pGEM3z (Promega, Madison, Wis.) or modified vectors thereof as well as other similar vectors known to those of skill in the art. As a particular realisation, the pGEM3z vector has been modified, and will be referred to as pGIS1 (see also FIGS. 7 and 10). pGEM vectors have also been disclosed in U.S. Pat. No. 4,766,072, herein incorporated by reference.

For the production of the parental nucleic acid molecule, for example full-length libraries and the GIS ditag libraries, suitable vectors are used. Accordingly, suitable vectors, which are within the scope of the present invention, are those wherein the backbone of the vector does not comprise the same restriction site comprised in the adapters flanking the parental nucleic acid molecule or the ditag, after insertion of the parental nucleic acid molecule. Preferably, the invention provides a vector wherein the vector backbone (other than within the stuffer region that is removed during insertion of the parental nucleic acid molecule) does not comprise the asymmetric restriction site and the second or further restriction site which are comprised into the adapters. In particular, the vector does not comprise the at least asymmetric II restriction site (for example type II restriction site) and the at least second or further restriction site comprised in the adapters. More preferably, the vector backbone (other than within the stuffer region that is removed during insertion of the parental nucleic acid molecule) does not comprise MmeI and BamHI.

Figure 7:
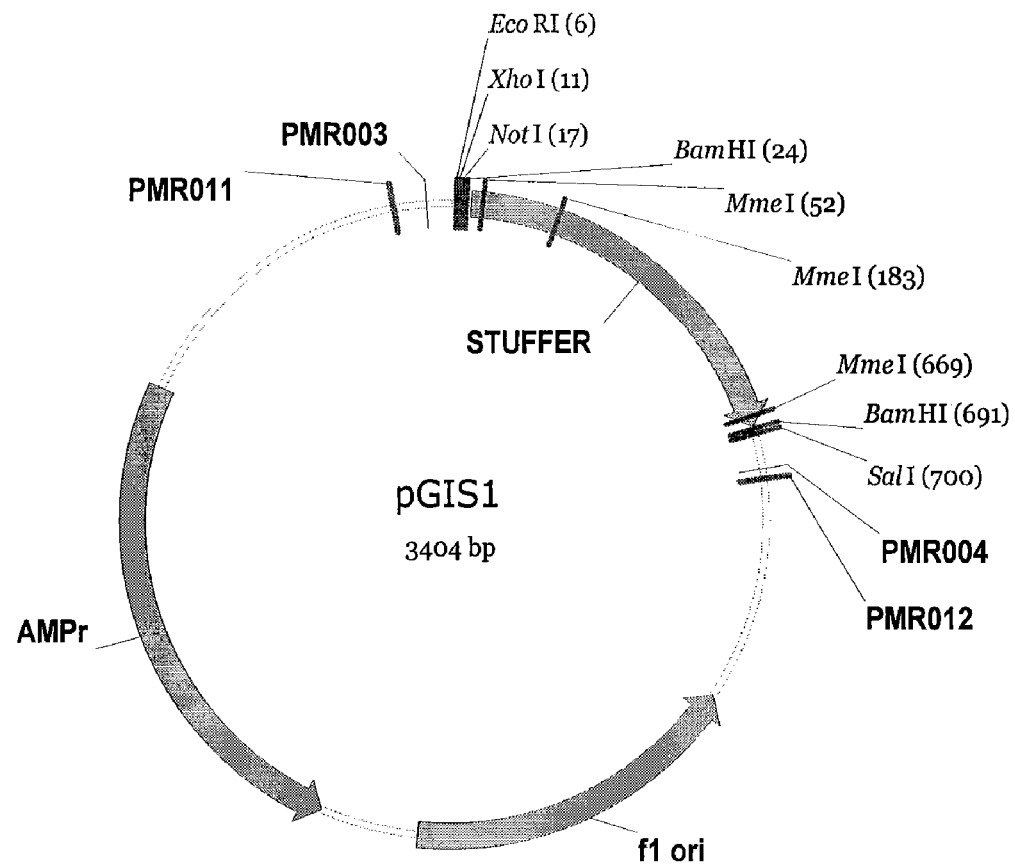
FIG. 7 shows the pGIS1 vector construct.

An example of such a vector not comprising MmeI in any region outside of the stuffer is the vector pGIS1 shown in FIG. 7 and FIG. 10. In pGIS1 the MmeI recognition sites were deleted by mutagenesis. The sequence is shown in FIG. 10 and in SEQ ID NO:18. In FIG. 10, the stuffer region between the sites NotI and SalI has been highlighted. The invention also related to the pGIS vector comprising the oligonucleotide according to any embodiment of the invention.

The oligonucleotide(s), ditag(s) or concatemer(s) of the invention may also be ligated into a vector for sequencing purposes.

Vectors in which the ditags are cloned can be transferred into a suitable host cell. Host cells are cells in which a vector can be propagated and its DNA expressed. The term also includes any progeny of the subject host cell. It is understood that all progeny may not be identical to the parental cell since there may be mutations that occur during replication. However, such progeny are included when the term host cell is used. Methods of stable transfer, meaning that the foreign DNA is continuously maintained in the host, are known in the art.

Transformation of a host cell with a vector containing ditag(s) may be carried out by conventional techniques as are well known to those skilled in the art. Where the host is prokaryotic, such as *E. coli*, competent cells which are capable of DNA uptake can be prepared from cells harvested after exponential growth phase and subsequently treated by the $CaCl_2$ method using procedures well known in the art. Alternatively, $MgCl_2$ or RbCl can be used. Transformation can also be performed by electroporation or other commonly used methods in the art.

An embodiment of this is shown in FIG. 1 and FIG. 2. According to this embodiment, the method of the invention comprises:

producing at least one nucleic acid molecule comprising a full-length cDNA molecule flanked by two adapters; each adapter comprising MmeI recognition sites and another recognition site, which may be BamHI, flanking the 5' terminus and 3' terminus of the full-length cDNA;

splicing the 5' terminus and the 3' terminus of the full-length cDNA to produce at least one ditag, comprising cleaving the full-length cDNA with MmeI which forms 3' overhanging tag ends, and ligating the two 5' and 3' termini tags to produce the ditag.

As shown in FIG. 1 and FIG. 2, the use of restriction enzymes may leave 5' and 3' double stranded end comprising a short overhanging end (also referred to as sticky end or cohesive end) consisting of few nucleotides. In particular, by using MmeI, the produced 5' and 3' ends consist each of a 20 bp double strand and two nucleotides as 3' overhanging ends. The two tags may be followed by blunt-ending and intramolecular self ligation to produce tagged plasmids that contain 18 bp signature sequence as 5' end and another 18 bp signature sequence as 3' end of the parental transcript. However, the number of nucleotides cut by MmeI is variable. Accordingly, the ditag obtained by using MmeI maybe of 34-38 bp.

The vector which has been used for the preparation of full-length cDNA library is pGIS1. As mentioned above, pGIS1 does not contain in its backbone MmeI restriction sites, other than within the stuffer region between Not I and Sal I, this stuffer region being subsequently removed during production of the libraries.

The oligonucleotide comprising the ditag flanked by the adapters is cut out form the GIS ditag library and linked to other oligonucleotides comprising ditag and adapters to form concatemers of ditags. The concatemers of ditag are then cloned into a vector for sequencing analysis.

Before cutting the oligonucleotide out from the GIS ditag library, it can be amplified directly from the ligation (self-circularization) reaction mix, for example by PCR using suitable primers. The recovered amplified oligonucleotide comprising ditag and adapters is then linked to other oligonucleotides comprising ditag and adapters to form concatemers of ditags. The concatemers of ditag are then cloned into a vector for sequencing analysis.

The method may further comprise the steps of:
determining the nucleotide sequence of the ditag;
detecting the gene expression;
and/or comparing the determined nucleotide sequence to a database comprising genomic sequences whereby matching 5' and 3' termini sequences are identified.

In particular, the at least one ditag comprises 36 nucleotides and the first and second sequence tags comprise each 18 nucleotides.

As mentioned above, the ditag according to the invention includes the "signature" (consisting of the 5' and 3' ends) of the nucleic acid molecule which is intended to be reduced or represented. Such ditags, preferably cDNA ditags, of a library may be concatenated and sequenced. The paired 5' and 3' signature sequences (tags) of a transcript in a ditag delineate the starting and ending points of transcripts. The ditag can be split up in the two tags during data analysis and mapped head-to-head in a specific region within a reasonable distance on a chromosome of an assembled genome sequence. The genomic DNA sequence in between these two tags is the full structural content of the prospective gene, including exons and introns.

Figure 3:
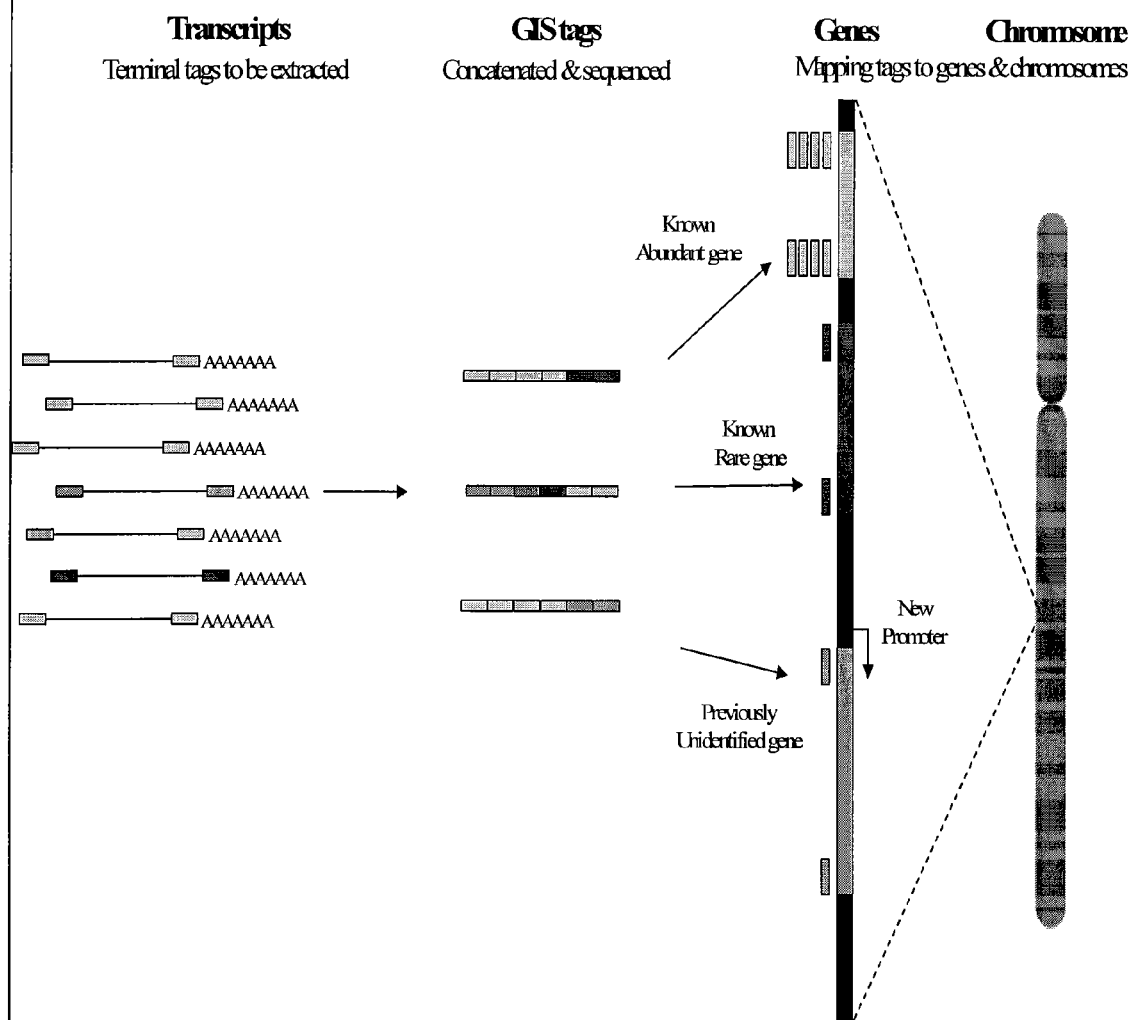
FIG. 3 shows the GIS application of mapping a transcriptome to a genome.

A general description of genome mapping using the ditag of the invention is shown in FIG. 3.

A modest sequencing run can generate sufficient data to characterize a transcriptome not only by determining the level of transcript abundance but also by defining the structure of transcripts using the revealed 5'and 3' regions. This results in about over 20-fold more efficient than EST sequencing.

Because the tags of the ditag can be matched to any genome, for example to human genomic sequences, PCR and RT-PCR primers can then be designed based on the matching genomic sequence.

Accordingly, a further aspect of the invention relates to a method for genome mapping, comprising:
preparing at least one oligonucleotide comprising at least one ditag, the ditag comprising two joined first and second sequence tags, wherein the first tag comprises the 5'-terminus sequence and the second tag comprises the 3'-terminus sequence of a nucleic acid molecule, the nucleic acid molecule corresponding to the full-length of a gene or fragment thereof;
mapping each of the two tags of the at least one ditag on the genome; and
defining the structural region of the corresponding gene on the genome map.

Further, it is also an aspect of the invention to provide a method of gene discovery comprising:
preparing at least one oligonucleotide comprising at least one ditag, the ditag comprising two joined first and second sequence tags, wherein the first tag comprises the 5'-terminus sequence and the second tag comprises the 3'-terminus sequence of a nucleic acid molecule, the nucleic acid molecule corresponding to the full-length of a gene or fragment thereof;
comparing the obtained at least one ditag with a genome map and/or a gene database;
detecting matching of the 5' and 3' termini tags on the genome map but detecting no match on one or more of the known gene database;

The method further comprises the step of recovering the full-length nucleic acid molecule corresponding to the newly discovered gene.

The invention also provides a method for recovering full-length cDNA comprising:
preparing, from a full-length cDNA library, at least one oligonucleotide comprising at least one ditag, the ditag comprising two joined first and second sequence tags, wherein the first tag comprises the 5'-terminus sequence and the second tag comprises the 3'-terminus sequence of a full-length cDNA;
sequencing the obtained oligonucleotide ditag;
determining the ditag of interest; and
recovering the full-length cDNA corresponding to the ditag of interest from the full-length cDNA library.

This method may be carried out according to any standard technology known in the art, for example, by PCR or screening using probes. The PCR primers and the probes sequences are prepared based on the information of the sequence of the ditag.

The invention also provides a method for quantifying the transcriptional activity of a gene comprising:
preparing, from a full-length cDNA library, at least one oligonucleotide comprising at least one ditag, the ditag comprising two joined first and second sequence tags, wherein the first tag comprises the 5'-terminus sequence and the second tag comprises the 3'-terminus sequence of a full-length cDNA;
sequencing the obtained oligonucleotide ditag;
determining the frequency of the sequenced ditag which corresponds to the transcriptional activity of the gene.

Method of Identification of Nucleic Acid Molecule Fragment(s) to which a Protein of Interest Binds For the performance of the method of this particular embodiment any description disclosed for the purpose of carrying out other embodiments of this invention may also be used and are herein incorporated by reference. In particular, technique(s), reagents, experimental conditions, restrictions sites, enzymes, vectors, primers, and the like. In particular, it will be evident to any skilled person how to adapt techniques and material disclosed for the other embodiments to the present embodiment of the invention.

The genome sequences of human, mouse and other mammals are now readily available in the public domain. In this postgenomic era, focus has shifted from raw DNA sequence collection to elucidating the functional content within the primary sequences. These functional entities would be the genes (either coding or non-coding) and the regions regulating the expression of these genes, including cis-acting elements such as promoters, enhancers, silencers, matrix attachment regions (MARs), and locus control regions (LCRs), and trans-acting proteins called transcription factors (TFs) that bind to promoter regions either singly or in a multifactorial complex. TFs can be divided into three categories: basal TFs, which are members of the basal transcription complex, which are involved directly in the recruitment of RNA polymerase to the start site; activators, which increase the rate of, or allow the formation of the basal transcription complex; and repressors, which decrease or prevent the formation of the basal transcription complex. Most eukaryotic promoters (that bind basal TFs) are of the Pol II category, and are usually located several hundred bp upstream of transcription initiation sites. However, parts of the 5' untranslated region (5' UTR) may also contain regulatory elements and may therefore also constitute part of the promoter.

Traditionally, the identification of TFBS (TFBS) was a slow and tedious process that involved the isolation and detailed characterization of the region of a gene upstream of a transcript's initiation site. Deletion and/or mutation analysis, DNase footprinting (DNase protection), electrophoretic mobility assays (EMSA) and reporter assays would be used to confirm the precise identity of this putative regulatory control region. A recent technique called chromatin immunoprecipitation (ChIP) greatly accelerates the identification of TFBS, and has the advantage that it identifies these sites in vivo. The bottleneck in ChIP analysis, however, is the downstream sequencing analysis required to identify the individual ChIP-enriched fragments.

Over time, the experimentally-confirmed consensus binding sequences of well-characterized TFs have been deposited into public databases such as TRANSFAC (Wingender, E., et al., Nucleic Acids Res, 1996. 24(1): p. 238-41). In silico approaches can thus also be used to scan regions of uncharacterized genomic DNA for the presence of putative TFBS, based on the consensus sequences. Another approach is based on the premise that orthologous genes should share the same regulatory regions and can therefore be identified by sequence alignments. Yet another approach involves studying the upstream regions of genes found to be coregulated in clustering analysis of cDNA microarray data; the assumption here is that coregulated genes share the same promoter(s) (and therefore are coregulated by the same set of TFs), which could theoretically be identified by aligning all the upstream DNA sequences together. However, given that even the same TF can bind different DNA sequences, this is not a trivial task. In silico approaches to predicting TFBS are reviewed in (Bulyk, M. L., Genome Biol, 2003. 5(1): p. 201).

GIS Analysis

A Gene Identification Signature (GIS) Analysis has been described in the first embodiment of the present application. This is a series of enzymatic steps (FIG. 1) that enables the isolation of the 5'- and 3'-most 20 bp of any full-length cDNA transcript, covalently links these terminal signatures into a ditag structure, and concatenates these ditags to enhance sequencing efficiency. By subsequently mapping the ditag sequences back onto assembled genome sequences, one can pinpoint the precise start and end of every transcription unit, thereby accurately annotating the locations of these TUs on the genome. Quantifying the expression level of transcripts is achieved by simply counting the numbers of their corresponding transcripts, in a manner similar to Serial Analysis of Gene Expression (SAGE) (Velculescu et al., Science, 1995. 270(5235): p. 484-7; Saha et al., Nat Biotechnol, 2002. 20(5): p. 508-12). Thus, GIS Analysis provides a way to rapidly and accurately characterize entire transcriptomes.

Importantly, the GIS Analysis procedure is also directly applicable for the characterization of any nucleic acid molecule in general, not just cDNA. The nucleic acid molecule may be RNA, mRNA, genomic DNA, cDNA, full-length cDNA. For the purpose of this embodiment, the GIS Analysis may be applied to the identification of regions of nucleic acid molecule fragment(s) to which a protein of interest binds. In particular, the present embodiment is addressed to a method of identifying at least a DNA fragment enriched with Transcriptional Factors Binding Site(s) (TFBSs).

In a particular scenario described herein, these fragments containing binding site(s) for the TF in question (or a multiprotein complex comprising one or more transcription factors and accessory proteins) were isolated using the standard ChIP technique or other suitable techniques. For instance, the formaldehyde cross-linking step could be replaced by one involving photoactivatable moieties incorporated in the DNA or the protein target of interest, and the retrieval of the DNA-bound protein complex by specific antibodies could be replaced with another affinity-based technique. Examples of such affinity-based techniques include streptavidin/biotin, Glutathione-S-transferase/glutatathione matrix, maltose-binding protein/amylose matrix interactions.

Chromatin Immunoprecipitation (ChIP)

ChIP is a powerful approach to enrich and thereby allow the identification of genomic regions associated with specific proteins such as histones and TFs (FIG. 2) (reviewed in (Taverner et al., Genome Biol, 2004. 5(3): p. 210). Briefly, the aim is to cross-link proteins with DNA at their sites of interaction. This is accomplished quickly and efficiently by adding formaldehyde directly to living cells in culture. Crude extracts of these fixed cells are then prepared, sonicated to shear chromatin to an average size of usually about 1 kb, then used in immunoprecipitation reactions with antibodies raised against the DNA-associated protein of interest (e.g. TFs or histones). DNA fragments enriched in each immunoprecipitation are then de-linked and purified to allow their identification by a variety of methods. The advantage of using ChIP is that this approach is able to "freeze" the in vivo gene regulatory network by rapid cross-linking of chromatin and other non-histone proteins, thereby in theory representing a "true" picture of the regulatory system at any point in time, free of potential artifacts imposed by heterologous expression, for instance. Recently, ChIP has been combined with whole-genome (Ren et al., Science, 2000. 290(5500): p. 2306-9; Iyer et al., Nature, 2001. 409(6819): p. 533-8; Lieb et al., Nat Genet, 2001. 28(4): p. 327-34), whole-chromosomal (Cawley et al., Nat Genet, 2001. 28(4): p. 327-34; Euskirchen et al., Mol Cell Biol, 2004. 24(9): p. 3804-14) and CpG island (Weinmann et al., Genes Dev, 2002. 16(2): p. 235-44) microarrays in a "ChIP-chip" or "ChIP-on-chip" approach (FIG. 3) that promises to enable the genome-level localization of TFBS (reviewed in Buck and Lieb, 2004). While the usefulness of this approach has been demonstrated for small genomes such as yeast (Ren et al., Science, 2000. 290(5500): p. 2306-9; Iyer et al., Nature, 2001. 409(6819): p. 533-8; Lieb et al., Nat Genet, 2001. 28(4): p. 327-34), the cost and complexity of producing whole-genome microarrays for more complex organisms still remains a limiting factor. CpG island microarrays contain human genomic fragments of high CpG content, and because CpG islands often correspond to promoter regions (Antequera and Bird, Proc Natl Acad Sci USA, 1993. 90(24): p. 11995-9), such microarrays represent a possible compromise. However, the location of putative TFBS still has to be indirectly inferred by examining genomic DNA upstream and downstream (usually 1-2 kb, as this is the approximate size of sonicated ChIP fragments) of the CpG-rich probe spotted on the array. It is worth noting that this locational ambiguity is a drawback shared with the ChIP-SAGE and ChIP-MPSS combined approaches mentioned below.

As an alternative, cloning and sequencing of the ChIP-enriched DNA fragments has previously been attempted but with limited success. The problem is that the targets of ChIP enrichment are obtained against a high background of the entire genome. Even a 100-fold enrichment of specific targets would still represent only a small fraction of clones in a ChIP library, making standard DNA sequencing a very costly solution. Therefore, sequencing ChIP clones under these circumstances is not a good approach for identifying the enriched targets. SAGE and Massively Parallel Signature Sequencing (MPSS) (Brenner et al., Nat Biotechnol, 2000. 18(6): p. 630-4) have also been suggested as useful quantitative tools for detecting ChIP enrichment, the underlying principle being that the tags generated from ChIP-enriched DNA fragments would be present in larger numbers compared to the nonspecific background. In theory, therefore, these tags could then be mapped to the genome sequence for identification of the general region of interest (i.e. assumed to be 1-2 kb, representing the sonicated fragments). Although the 20 bp SAGE and MPSS tags should be specific enough in most instances to define the specific genome location, one still has to examine all sequences approximately 1-2 kb upstream and downstream of the tag when mapping to the genome. This is the same problem faced by the CpG island microarray approach. Furthermore, complete coverage using these methods depends on the availability of prerequisite restriction enzyme recognition sites (mapping-enzyme sites); if a recognition site is absent from a certain genomic location, that particular tag will be missing from the corresponding ChIP fragment, and hence that location will be a "blind spot" within the genome.

ChIP-GIS

From the issues described above, it is clear that what is required to facilitate genome level transcriptional regulatory analysis is a method to accurately and rapidly pinpoint the sequences of TF binding regions, as an alternative to whole genome arrays. In this regard, the novel GIS analysis approach provided by the present invention, in particular in the form of ChIP-GIS, possesses several advantages: (i) the ditag sequences generated by GIS analysis provide higher specificity for mapping, because each GIS ditag (for example, 36 bp ditag(s)) would already be known to have been derived from a contiguous DNA segment encompassed by the 5' and 3' signatures. This information facilitates precise localization of the genomic region of interest, and obviates the need to repeatedly examine every sequence an arbitrary 1-2 kb upstream and downstream of a standard SAGE or MPSS tag; (ii) the GIS analysis method is independent of any requirement for the presence of mapping-enzyme sites; (iii) the concatenation of ditags prior to sequencing means that several ditags, for example an average of 15 ditags (corresponding to 15 separate DNA fragments), can be identified within 1 sequencing read (for example, a sequencing read of approximately 700 bp); (iv) the region that is common to (i.e. overlapped by) all mapped ditags in that cluster therefore defines the exact consensus in vivo binding site of the TF in question.

An example of the application of the ChIP-GIS approach is displayed in FIG. 13, and described in greater detail below.

Accordingly, the present invention provides a method of identifying at least a nucleic acid molecule fragment to which a protein of interest binds, comprising:

(i) preparing at least one nucleic acid molecule fragment to which a protein binds;
(ii) isolating the 5' terminus and the 3' terminus of the nucleic acid fragment(s) and linking the 5' terminus and 3' terminus to create the at least one ditag;
(iii) sequencing the ditag; and
(iv) mapping the ditag sequence(s) to the genome.

In particular, the method according to this embodiment may be a method for the identification and/or discovery of transcription factor binding site(s) (TFBSs).

The nucleic acid fragment to which a protein of interest binds may be any nucleic acid fragment comprising a region to which a protein of interest binds, for example, trans-acting protein(s) binding site. In particular, the nucleic acid molecule fragment of the invention is preferably a genomic DNA fragment enriched for transcription factor binding site(s) (TFBSs).

In this embodiment, before carrying out step (ii), the nucleic acid molecule fragment to which a protein binds is preferably inserted into a vector. The vector may be any vector suitable for the purposes of the present embodiment. In particular, the vector comprises two regions (or motifs) flanking the nucleic acid molecule fragment which is to be inserted into the vector. Each region (motif) comprises at least: a first restriction site which is an asymmetric restriction site and/or at least a second restriction site, and wherein the remainder of the backbone of the vector does not comprise the asymmetric restriction site and/or the second restriction site. The asymmetric recognition sites may be restriction endonuclease asymmetric cleavage site sequences recognizable by type II or type III restriction enzymes or homing endonucleases as described above with reference to other embodiments of the present invention. In particular, the type II restriction site is MmeI. According to a particular aspect, the vector of the invention is the vector pGIS3 (illustrated in FIG. 17). The sequence of pGIS3 is also disclosed as SEQ ID NO:22.

Examples of type II restriction enzymes as well as examples of homing endonucleases have been given above.

Examples of type III restriction site(s) and type III enzyme(s) have been described in; I Matsumura H, et al., SuperSAGE, Proc Natl Acad Sci USA. 2003 Dec. 23;100 (26):15718-23; Moencke-Buchner, E., et al., J. Biotechnol., 114: 99-106 (2004); Mucke, M., et al., J. Mol. Biol. 312: 687-698 (2001); Rao, D. N., et al., J. Mol. Biol. 209: 599-606 (1989); Hadi, S. M., et al., J. Mol. Biol. 134: 655-666 (1979).

Type III restriction enzymes can also by purchased from New England Biolabs (NEB).

List of known Type III enzymes can also be found in the REBASE site rebase.neb.com.

In particular, a preferable type III enzyme, for carrying out any embodiment of the present invention is the type III enzyme: EcoP15I. The recognition site(s) of EcoP15I is CAGCAG (25/27).

The ditags of the present embodiment may be prepared and may have the size as described above in other embodiments of the present invention. The ditags may be joined to form a concatemer of ditags. The concatemer may comprise 1-1000 ditags. The concatemer(s) may also be prepared as described above in other embodiments of the invention.

The ditag(s) and/or concatemer(s) may be amplified according to any suitable standard techniques, for example by polymerase chain reaction (PCR).

According to a particular aspect, in the method of this embodiment the nucleic acid molecule fragment of step (i) is isolated from a living cell by: (a) cross-linking DNA binding protein in the living cell to genomic DNA of the living cell, thereby producing DNA binding protein cross-linked to genomic DNA; (b) generating DNA fragments of the genomic DNA cross-linked to DNA binding protein in (a), thereby producing a DNA/protein complex comprising DNA fragments to which the DNA binding protein is bound; (c) removing the DNA fragment to which the protein of interest is bound from the complex produced in (b); and (d) isolating the DNA fragment identified in (c) from the protein of interest. The DNA/protein complex may be isolated by antibody-mediated immunoprecipitation.

In particular, the nucleic acid molecule fragment(s) may be isolated by chromatin immunoprecipitation. Alternatively, the nucleic acid molecule fragment(s) may be isolated by incorporating a photoactivable moiety into the DNA and/or the protein of interest and isolation of DNA/protein complex by antibody-mediated precipitation or by affinity-mediated techniques or methods. Examples of such affinity-based techniques include streptavidin/biotin, Glutathione-S-transferase/glutatathione matrix, maltose-binding protein/amylose matrix interactions.

According to a particular aspect of this embodiment, the method of identifying at least one DNA fragment to which a protein of interest bind comprises: (a) cross-linking DNA binding protein(s) in living cell(s) to genomic DNA of the living cell, thereby producing DNA binding protein cross-linked to genomic DNA; (b) generating DNA fragments of the genomic DNA cross-linked to DNA binding protein in (a), thereby producing a DNA/protein complex comprising DNA fragments to which the DNA binding protein is bound; (c) removing the DNA fragment to which the protein of interest is bound from the complex produced in (b); (d) isolating the DNA fragment(s) identified in (c) from the protein of interest; (e) inserting the isolated DNA fragment(s) into a vector; (f) isolating the 5' terminus and the 3' terminus of the nucleic acid fragment(s) inserted into the vector and linking the 5' terminus and 3' terminus to create the at least one ditag; (g) sequencing the ditag; and (h) mapping the ditag sequence(s) to the genome.

In the step (a) formaldehyde may be added to living cells; and in step (b) crude extracts of the fixed cells are prepared, and sonicated to shear the chromatin.

In particular, the protein of interest binds to the nucleic acid molecule fragment(s) at a consensus binding site which may be determined or identified by the region of genomic DNA encompassed (or spanned) by the two signatures of the ditag.

Further, the present invention provides a vector comprising at least one ditag, wherein the ditag comprises two joined first and second sequence tags, and wherein the first tag includes a 5'-terminus sequence and a second tag comprises the 3'-terminus sequence of a nucleic acid molecule fragment, and wherein the nucleic acid molecule fragment is enriched for transcription factor binding sites (TFBSs). In particular, in the vector the ditag may be flanked at each side by at least: a first restriction site which is an asymmetric restriction site and/or at least a second restriction site, and wherein the backbone of the vector does not comprise the asymmetric restriction site and/or the second restriction site. The asymmetric restriction site may be a type II restriction site or a restriction site recognised by a homing endonuclease. In particular, the vector has the nucleotide sequence of SEQ ID NO:22.

The p53 Model System p53 protein is a TF (known binding consensus=5'-PuPu-PuC(A/T)(T/A)GPyPyPy-3'; Pu=purine; Py=pyrimidine; SEQ ID NO:19) that activates many genes involved in cell cycle control, DNA repair and apoptosis. It is also the most common defect in many tumors (Hussain and Harris, 1998). In classical models, it is believed that p53 protein is found within cells in a latent state, i.e. in low amounts and bound non-specifically to DNA at low affinity; in this model, p53 is activated in response to various intracellular and extracellular signals. Activation involves an increase in overall p53 protein levels, as well as allosteric changes in the protein. Upon activation, p53 can induce a variety of cellular responses (Oren, M., Cell Death Differ, 2003. 10(4): p. 431-42). These models suggesting that stress-induced post-translational modifications (such as ubiquitination, phosphorylation or acetylation) alter the DNA binding affinity of p53, resulting in its selective recruitment to the promoters of the genes it regulates, were challenged by results from a ChIP study apparently showing that the state of "latency" did not exist, and may be an artifact of in vitro binding studies (Kaeser and Iggo, Proc Natl Acad Sci USA, 2002. 99(1): p. 95-100); the issue remains unresolved.

Recent genome-wide analyses of p53 binding have highlighted additional interesting results, including a ChIP-chromosome tiling study revealing that only a minority of TF (including p53) binding sites were located at canonical 5' termini of coding sequences, and more of the binding sites were located within or immediately 3' to known genes, suggesting either the presence of location-independent regulatory regions (such as enhancers or silencers), or promoters for noncoding transcripts (Cawley et al., Nat Genet, 2001. 28(4): p. 327-34).

It is obvious from the above that a genome-wide ChIP-based survey of p53 interactions is more informative and presents a more authentic overview of the p53 transcriptional regulatory network than examining individual p53 binding sites in vitro; in addition, because p53 has been well-characterized, an abundance of information already exists, making it easier to cross-reference results. For these reasons, we chose p53 as a model system to validate our ChIP-GIS approach.

Having now generally described the invention, the same will be more readily understood through reference to the following examples which are provided by way of illustration, and are not intended to be limiting of the present invention.

EXAMPLES

GIS oligonucleotides for cDNA synthesis, the structure of a generic 50 bp cohesive ditag, primers used for the construction of vector pGIS1, and ds-DNA adapter which are used in the examples are listed below.

GIS Analysis Oligos for cDNA Synthesis
  GsuI-oligo dT primer:

(SEQ ID NO:1)
5'-GAGCTCCTT<u>CTGGAG</u>TTTTTTTTTTTTTTTVN-3'

NotI/BamHI/MmeI(N)6 primer linker (top):

(SEQ ID NO:2)
5'-AATTC<u>GCGGCCGC</u>TTGGA<u>TCCGAC</u>NNNNNN

NotI/BamHI/MmeI(N) primer linker (bottom):

(SEQ ID NO:3)
5'-p-GTCGGATCCAAGCGGCCGCG-3'

NotI/BamHI/MmeI(N)5 primer linker (top):

(SEQ ID NO:4)
5'-AATTC<u>GCGGCCGC</u>TTGGA<u>TCCGAC</u>GNNNNN

MmeI/BamHI/SalI adapter (top):

(SEQ ID NO:5)
5'-TCGACCCAGGA<u>TCCAA</u>CTT-3'

MmeI/BamHI/SalI adapter (bottom):

(SEQ ID NO:6)
5'-p-GTTGGATCCTGGG-3'

(SEQ ID NO:7)
PMR003: 5'-GTAAAACGACGGCCAGt-3'

(SEQ ID NO:8)
PMR004: 5'-GGAAACAGCTATGACCATG-3'

-continued

```
                                            (SEQ ID NO:9)
    PMR006:  5-TAATACGACTCACTATAGGG-3'

(SEQ ID NO:10)
    PMR011:  5'-GATGTGCTGCAAGGCGATTAAG-3'

(SEQ ID NO:11)
    PMR012:  5-AGCGGATAACAATTTCACACAGG-3'.
```

Structure of a Generic 50 bp Cohesive Ditag

```
                                                  (SEQ ID NO:12)
5-GATCCGACXXXXXXXXXXXXXXXXXXXXNNNNNNNNNNNNNNNNNNAAGTTG (SEQ ID NO:13)
GCTGXXXXXXXXXXXXXXXXXXXXNNNNNNNNNNNNNNNNNNTTCAACCTA
G-5'
```

Wherein X and N may be any of A, C, G or T.

Primers used for the construction of vector pGIS1

Mme_mut1:
```
                                           (SEQ ID NO:14)
5'-p-CGCTCTCCTGTACCGACCCTGCCGCTTAC-3'
```

Mme_mut2:
```
                                           (SEQ ID NO:15)
5'-p-AACTATCGTCTTGAGACCAACCCGGTAAG-3'
``` ds-DNA adapter
```
                                           (SEQ ID NO:16)
5'-AATTCTCGAGCGGCCGCGATATCG-3'

(SEQ ID NO:17)
3'-GAGCTCGCCGGCGCTATAGCTTAA-p-5'
``` pGIS1 Sequence

The sequence of pGIS1 (SEQ ID NO:18) is shown in FIG. 10.

The known binding consensus of protein p53 is 5'-(A/G)(A/G)(A/G)C(A/T)(T/A)G(C/T)(C/T)(C/T)-3' (SEQ ID NO: 19), wherein A/G indicates a purine (a purine may be indicated as "Pu" or "r"), C/T indicates a pyrimidine (a pyrimidine may be indicated as "Py" or "y"), A/T or T/A may be also indicated as "w".

```
                                            SEQ ID NO:20
          5'-GAACATGTCCCAACATGTTG-3':.

SEQ ID NO:21
          5'-AGACAAGCCCGGGCAAGGCC-3':.
```

The sequence of pGIS3 (SEQ ID NO:22) (without ditag) is shown in FIG. 17.

Figure 14:
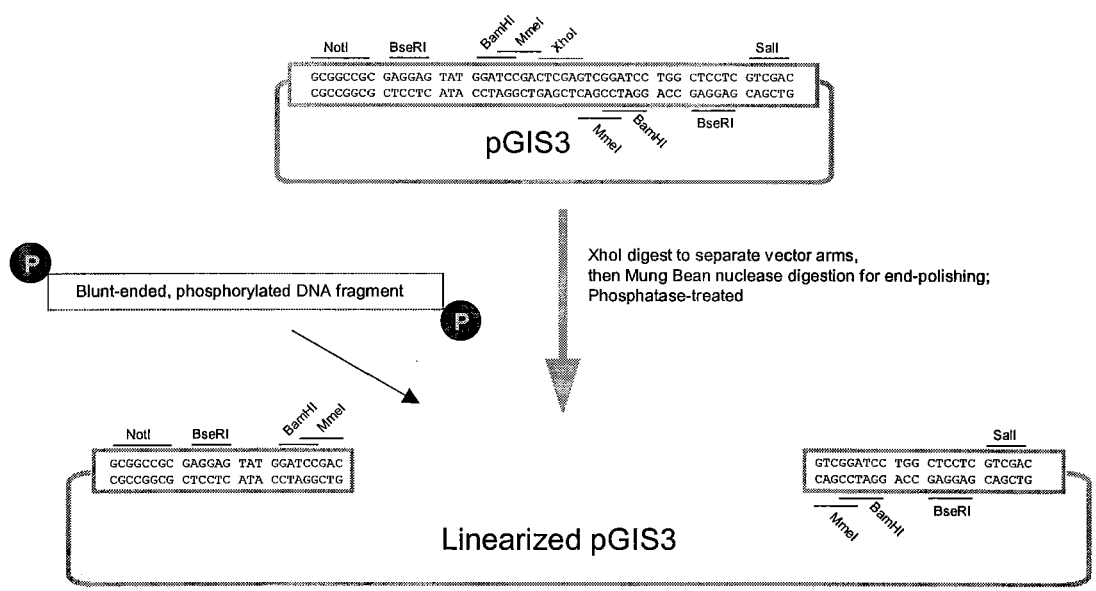
FIG. 14 shows the cloning vector pGIS3 used for the ChIP-GIS Analysis method. Any blunt-ended, phosphorylated DNA fragment (including ChIP-enriched DNA) can be inserted into prepared pGIS3. pGIS3 is prepared by first opening it up with XhoI, then removing the overhangs using Mung Bean nuclease. Finally, it is treated with alkaline phosphatase to reduce self-ligation. 5' to 3' sequences of the three regions illustrated in FIG. 14 are reported in SEQ ID NOS: 23-25.

5'-gcggccgcga ggagtatgga tccgactcga gtcggatcct ggctcctcgt cgac-3' (SEQ ID NO: 23) is the upper strand of the DNA fragment illustrated in FIG. 14 which is part of the pGIS3 vector (lower strand: SEQ ID NO: 33).

5'- gcggccgcga ggagtatgga tccgac-3' (SEQ ID NO: 24) is the upper strand of a DNA fragment, which is a portion of the pGIS3 vector obtained after the addition of XhoI to obtain separate vector arms (FIG. 14) (lower strand: SEQ ID NO: 34).

5'-gtcggatcct ggctcctcgt cgac-3' (SEQ ID NO: 25) is the upper strand of a DNA fragment, which is a portion of the pGIS3 vector obtained after the addition of XhoI to obtain separate vector arms (FIG. 14) lower strand: SEQ ID NO: 35).

Example 1

The Method

The experimental procedure of GIS ditag analysis has been carried out according to the following modules of cDNA library construction and analysis:
(1) The full-length cDNA library which introduces the MmeI sites flanking both ends of each cDNA insert;
(2) The GIS ditag library in which each clone contains a 5' 18 bp signature and a 3' 18 bp signature of a transcriptional unit;
(3) The GIS library for clones of concatenated GIS ditags;
(4) GIS sequencing analysis.

1. GIS Full-length cDNA Library with Addition of MmeI Sites for each cDNA Inserts The outline of procedure of this section was as follows: starting from high quality mRNA, the first cDNA was synthesized with a GsuI-oligo dT primer (SEQ ID NO:1).

The first strand cDNA/RNA hybrids was subjected to a full-length enrichment procedure by the biotinylation-based cap-trapper approach. Any cap-trapper approach known in the art can be used, for example Caminci et al., 1996, Genomics, Vol. 37, 327-336; U.S. Pat. No. 6,143,528; Edery et al., 1995, Mol. Cell. Biol., Vol. 15, No. 6, 3363-3371).

The enriched full-length first strand cDNA was the template for second cDNA synthesis primed with adapter-primer (NotI/BamHI/MmeI-(N)5 and -(N)6, (SEQ ID NOS: 2-4) that contain a MmeI, a BamHI, and a NotI site.

After the double strand cDNA was made, the cDNA poly-A/T tail was cleaved off by GsuI restriction enzyme. GsuI is another Type-II endonuclease that cleaves DNA 16 bp from its recognition site. At the GsuI cleavage end, an adapter containing a MmeI, a BamHI site, and a SalI cohesive end was ligated to the cDNA (SEQ ID NOS: 5-7).

Following a NotI digestion, the full-length cDNA was inserted into the vector pGIS1, between the NotI and SalI sites in the polylinker. The vector pGIS1 (see FIGS. 7 and 10) is modified from pGEM3z (Promega).

mRNA Preparation

The total mRNA has been prepared from mouse embryonic stem cell line E14 using Trizol reagent (Invitrogen). However, any standard method (as those described in Sambrook J. and Russell D. W., 2001, Molecular Cloning, Cold Spring Harbor Laboratory Press) may also be used.

mRNA (polyA RNA) was purified by oligo dT magnetic beads according to standard techniques (for example, Sambrook and Russell, 2001, as above). Alternatively, purification may be carried out by affinity column according to standard techniques (for example, Sambrook and Russell, 2001, as above).

First Strand cDNA Synthesis and Full-length Selection

In this step, the first cDNA is synthesized with a GsuI-oligo dT primer. Then, the first strand cDNA/RNA hybrids are subjected to a full-length enrichment procedure by the biotinylation-based cap-trapper approach.

GsuI-oligo dT primer:

```
                                            (SEQ ID NO:1)
5'-GAGCTCCTTCTGGAGTTTTTTTTTTTTTTTTVN-3'
```

The following were mixed:
GsuI-oligo dT primer (7 µg/µl) 2 µl
PolyA RNA (20 µg) 18 µl The obtained solution was heated to 65° C. for 10 min and 37° C. for 1 min.

Then, spin tube in microfuge and the following substances were added:

| | |
|---|---|
| 2× GC-I buffer (Takara) | 75 µl |
| RNase inhibitor Promega) | 1 µl |
| 10 mM dNTP (with methyl-dCTP) | 4 µl |
| Saturated trehalose | 10 µl |
| 4.9M sorbitol | 26 µl |
| Superscript II reverse transcriptase (Invitrogen) | 15 µl |

The obtained solution was incubated at 37° C. for 10 min, 42° C. for 30 min 50° C. for 20 min and 55° C. for 20 min. 2 µl of proteinase K (20 mg/ml) were added. The obtained solution was Incubated at 45° C. for 15 min followed by phenol/chloroform extraction and isopropanol precipitation (according to standard technique, eg. Sambrook and Russel, 2001, as above).

The RNA/cDNA heteroduplex was re-suspended into 44.5 µl of ddH$_2$O. 3 µl of 1.1 M NaOAc pH 4.5 and 2.5 µL of 100 mM NaIO$_4$ were added to oxidize the diol structures of the mRNA. 50 µl of the reaction solution were incubated on ice in the dark for 45 min followed by adding 0.5 µl of 10% SDS, 11 µl of 5 M NaCl and 61 µL of isopropanol to precipitate the RNA/DNA. The precipitated RNA/DNA was resuspended in 50 µl of ddH$_2$O. 5 µL 1M NaOAc (pH6.1), 5 µL 10% (w/v) SDS and 150 µL 10 mM long-arm biotin hydrazide were added to biotinylate the RNA. The reaction was incubated at room temperature in dark overnight. The biotinylated RNA/DNA was precipitated by adding 5 µL 5M NaCl, 75 µL 1M RNase-free NaOAc (pH6.1), and 750 µL 100% EtOH or 200 µL of 100% Isopropanol. Incubate at −80° C. for 30 min by spin 14 krpm at 4° C. for 30 min.

The pellet was washed with 70% (v/v) EtOH/30%, DEPC-treated ddH$_2$O (DEPC is diethylpyrocarbonate, which is an RNase inhibitor), and 14 krpm spin was carried out at 4° C. for 10 min. The extra liquid was carefully removed. Then, the pellet was air-dried, and resuspended in 400 µL DEPC-ddH$_2$O. Then 50 µL 10×RNaseI buffer and 25 units RNaseI/µg of starting mRNA were added. The obtained solution was incubated at 37° C. for 30 min. 10 µL of 10 mg/mL Yeast tRNA (Ambion) and 150 µL of 5M NaCl were added to stop the reaction.

While biotinylating the RNA-DNA heteroduplex, the Streptavidin Dynabeads were prepared as follows: 400 µL of M-280 Streptavidin beads (Dynal) were pipetted into an RNase-free Eppendorf tube, the beads placed on a magnet, left staying for at least 30 min, and then the supernatant was removed. The beads were re-suspended in 400 µL 1× binding buffer (2M NaCl, 50 mM EDTA, pH 8.0). The tube was placed on a magnet, waited at least 30 min, and then the supernatant was removed. The 1× binding buffer wash was repeated for 2 more times. The beads were re-suspended in 400 µL 1× binding buffer with 100 µg of Yeast tRNA, and then incubated at 4° C. for 30 min with occasional mixing. The tube was placed on a magnet stand, waited at least 30 seconds, and the supernatant was removed. The beads were washed with 1×binding buffer for 3 times. The beads and RNA/DNA heteroduplex were mixed (the total volume now was 660 µL, and the binding condition was at 1 M NaCl). The mixture was rotated at room temperature for 30 min.

The tube was placed on a magnet stand, waited at least 30 seconds, and the supernatant removed (the supernatant was saved as "unbound").

The beads were washed two times with 400 µL of 1×binding buffer. Washed with 400 µL of 0.4% (w/v) SDS plus 50 µg/mL Yeast tRNA. Washed with 400 µL of 1× wash buffer (10 mM Tris-HCl pH7.5, 0.2 mM EDTA, 10 mM NaCl & 20% (v/v) glycerol, 40 µg/mL Yeast tRNA). And washed w/400 µL of 50 µg/mL Yeast tRNA. For all washes the tube was placed on a magnet stand, waited for at least 30 seconds, and the supernatant was removed.

The first strand cDNA was released by alkali hydrolysis of RNA. The following was added: 50 µL 50 mM NaOH and 5 mM EDTA (pH8.0). The tube was rotated at 65° C. for 10 min. The tube was placed on a magnet stand, and the supernatant transferred to another tube containing 50 µL 1M Tris-Cl (pH7.5).

The lysis procedure was repeated for 2 more times. The final volume of supernatant was 300 µL (containing the first strand cDNA).

The cDNA was extracted by phenol/chloroform extraction and precipitate by 1 mL ethanol with glycogen. The cDNA was re-suspended in 5 L LoTE (0.1X) LoTE is low salt Tris-EDTA buffer (3 mM Tris-HCl pH 7.5 and 0.2 mM EDTA pH7.5)).

1-3 Second Strand cDNA Synthesis

The following reagents were added to the each corresponding tube on ice.

| | |
|---|---|
| cDNA in LoTE | 5 µL |
| Linker (N5) | 1.6 µg |
| Linker (N6) | 0.4 µg |
| Soln II (Takara ligation kit) | 10 µL |
| Soln I (Takara ligation kit) | 20 µL |

Linker (N6) is:
NotI/BamHI/MmeI(N)6 primer linker (top):

(SEQ ID NO:2)
5'-AATTCGCGGCCGCTTGGATCCGACNNNNNN

NotI/BamHI/MmeI(N) primer linker (bottom):

(SEQ ID NO:3)
5'-p-GTCGGATCCAAGCGGCCGCG-3'

Linker (N5) is:
NotI/BamHI/MmeI(N)5 primer linker (top):

(SEQ ID NO:4)
5'-AATTCGCGGCCGCTTGGATCCGACGNNNNN

NotI/BamHI/MmeI(N) primer linker (bottom): is the sequence (SEQ ID NO:3) indicated above.

The cDNA and linker mixture was incubated at 16° C. overnight. And the following were added:

| | |
|---|---|
| ddH$_2$0 | 20 µL |
| 10× ExTaq buffer (Takara) | 8 µL |
| 2.5 mM dNTP | 8 µL |
| ExTaq polymerase (Takara) | 4 mL |

The mixture was preheated in a thermo-cycler 65° C., 5 min→68° C., 30 min→72° C., 10 min., followed by phenol/chloroform extraction and ethanol ppt with glycogen, and re-suspended in 85 μl ddH$_2$O.

1-4. Removal of PolyA Tail by GsuI Digestion

The following reagents were added to the tube.

| | |
|---|---|
| cDNA | 85 μL |
| GsuI (Fermentas) | 5 μL |
| 10× bufferB (Fermentas) | 10 μL |

The mixture was incubated at 30° C. for 2 hours, followed by phenol/chloroform and ethanol precipitation. The pellet was re-suspended in 10 ul ddH2O, and the following 3' adaptor ligation reaction was carried out.

1-5. Addition of 3' Adaptor with MmeI and BamHI and SalI Sites

The following components were added to the tube containing 10 μl of sample. The 10 μl of sample was the double-stranded full-length cDNA which has had the poly(A) tail removed by GsuI digestion.

| | |
|---|---|
| 5× ligation buffer | 10 μL |
| GsuI SalI adapter (0.4 μg/μL) | 25 μL |
| (The GsuI SalI adapter is MmeI/BamHI/SalI adapter) | |
| T4 DNA ligase (5 units/ul) (Invitrogen) | 5 μL |

MmeI/BamHI/SalI adapter (top):

(SEQ ID NO:5)
5'-TCGACCCAGGA*TCCAA*CTT-3'

MmeI/BamHI/SalI adapter (bottom):

(SEQ ID NO:6)
5'-p-GTTGGATCCTGGG-3'

The reaction was incubated at 16° C. overnight, followed by phenol/chloroform extraction and ethanol precipitation, and the pellet re-suspended in 41 μl dH$_2$O.

1-6. NotI Digestion and cDNA Size Fractionation

The following were added on ice and in order:

| | |
|---|---|
| NEB Buffer 3 | 5 μL |
| NotI (10 units/μl) (NEB) | 4 μL |

The obtained solution was incubated at 37° C. for 1-2 hours.

cDNA Size Fractionation Columns were prepared (the Invitrogen instructions were followed: uncap the column (bottom first) and allow it to drain completely; wash 5 times with 800 μL T$_{10}$E$_{0.1}$N$_{25}$ Buffer, allowing the column to drain completely each time). The DNA sample was loaded onto the column. The flow-through was collected in an Eppendorf tube (fraction 1). 100 μL of T$_{10}$E$_{0.1}$N$_{25}$ Buffer were added. The flow-through was collected in an Eppendorf tube (fraction 2). Another 100 μL of T$_{10}$E$_{0.1}$N$_{25}$ Buffer was added. The flow-through collected, one drop per pre-numbered Eppendorf tube (beginning with fraction 3, each drop was about 30-40 μL).

Whenever the column runs dry, another 100 μL of T$_{10}$E$_{0.1}$N$_{25}$ Buffer may be added.

Up to drop 20 should be collected (according to the Invitrogen protocol). 3 μL of each fraction were run on agarose gel to visualize the cDNA size in each fraction. Pool fractions were showing cDNA ≧1.0 kbp (usually up to 2-3 kbp). Pooled samples were kept neat (using a cuvette soaked at least 30' in slightly acidified 100% EtOH, rinsed 5 times with ddH$_2$O, and saving sample. This is what has to be ligated).

If only one fraction is to be used, precipitate it and use the half to all of it, depending on what the gel looks like.

At this point the cDNA fragments have the NotI cohesive end at 5' side and SalI cohesive end at 3' side, and are ready to be cloned in vector.

1-7. Ligation of cDNA with Linearized Plasmid pGIS1.

Figure 9:
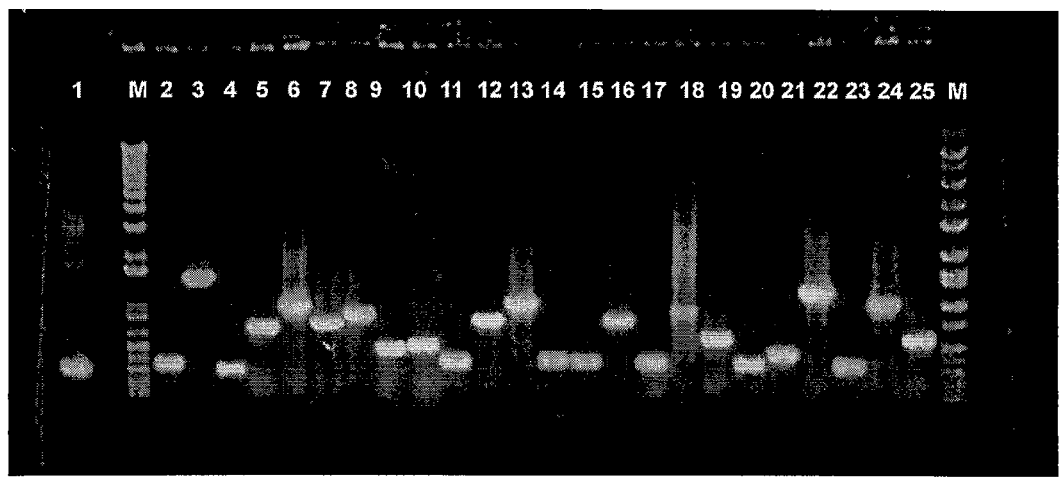
FIG. 9 shows a typical example of the QC (quality check) performed on multiple clones from the GIS library using PCR. Lane 1: pZErO-1 vector as negative control. M: 1 kb+DNA ladder. Lanes 2-25: randomly-picked clones.
Figure 11:
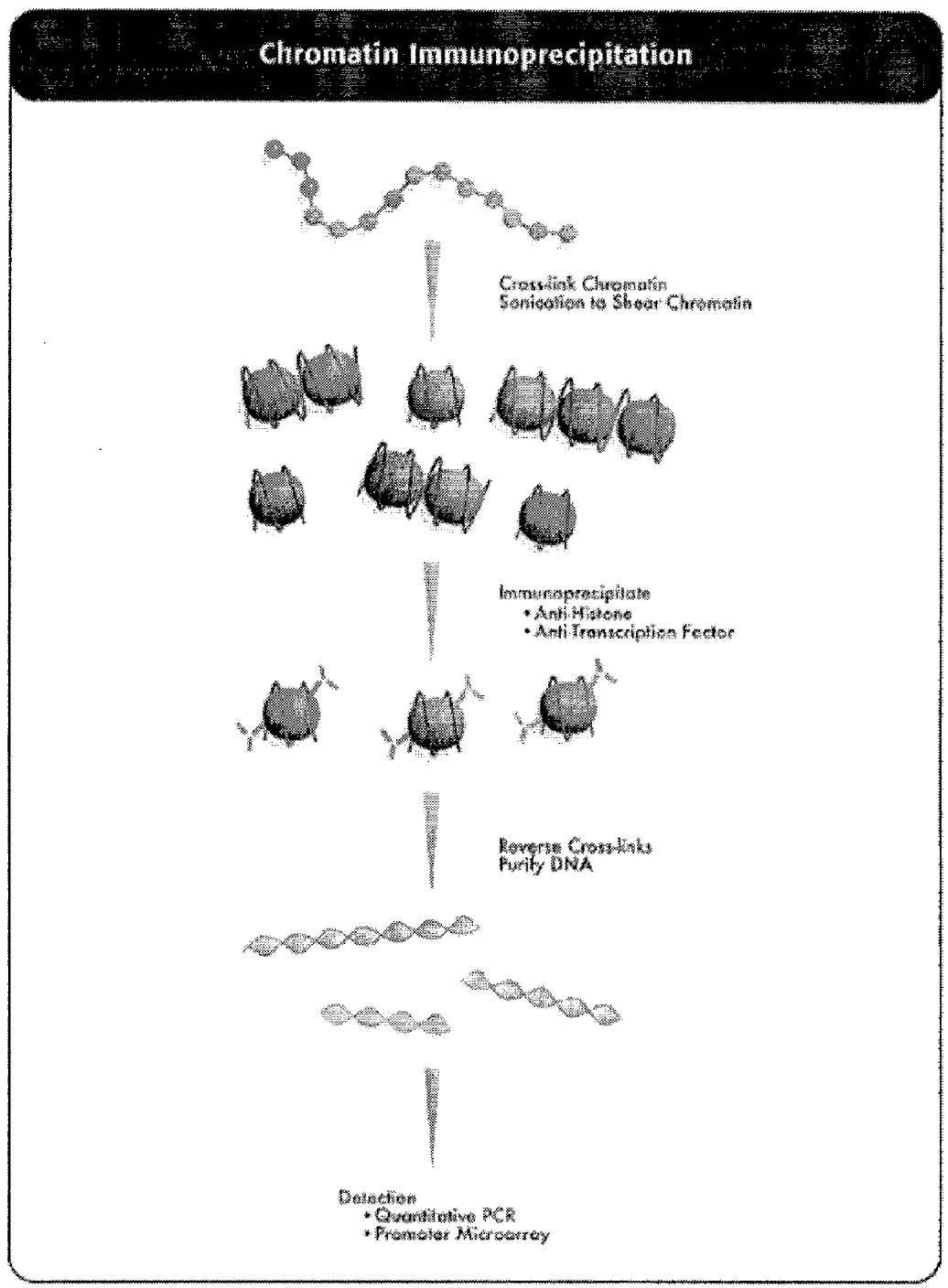
FIG. 11 shows the schematic representation of the chromatin immunoprecipitation (ChIP) technique. First, the proteins are cross-linked to DNA with formaldehyde, and then the chromatin is sheared to a manageable size by sonication. Specific proteins are immunoprecipitated with antibodies, also bringing down the DNA to which the protein is cross-linked. The cross-links are reversed, the DNA purified, and the sample is analyzed for the enrichment of specific DNA sequences. The detection step can be performed by cloning and sequencing, by quantitative real-time PCR, and by the usage of genome microarrays (ChIP-chip, see FIG. 12). It is proposed to use an enhanced cloning and mapping procedure called GIS for this purpose instead of the abovementioned detection steps (Figure and legend adapted from Upstate Biotechnology Inc.).
Figure 12:
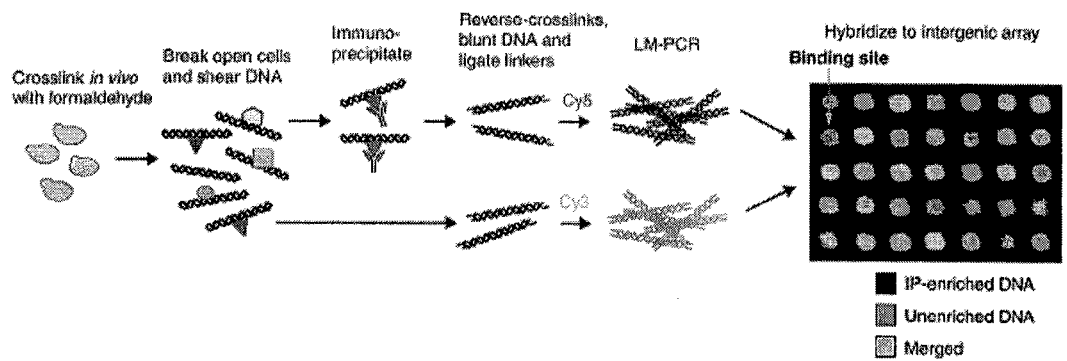
FIG. 12 shows the ChIP-chip or "ChIP-on-chip" procedure. ChIP-enriched DNA is labeled with Cy5, while unenriched or baseline DNA from the same sample is labeled with Cy3. Competitive hybridization to an array comprising genomic regions would highlight the presence of fragments that are present in differentially greater or smaller quantities.

1-7-1 The cloning vector pGIS1 was prepared by NotI and SalI digestion. The vector sequence of pGIS1 is shown in FIGS. 7 and 9.

pGIS1 Cloning Vector Construction (I) Site-specific Mutagenesis of pGEM3z to Create MmeI-minus Vector The vector pGIS-1 was derived from pGEM3z (Promega). pGEM3z originally contained two MmeI recognition sites that were knocked-out by site-directed mutagenesis. The QuikChange Multi kit (Stratagene) was used, together with mutagenic primers:

Mme_mut 1:
(SEQ ID NO:14)
5'-p-CGCTCTCCTGTACCGACCCTGCCGCTTAC-3'

Mme_mut2:
(SEQ ID NO:15)
5'-p-AACTATCgTCTTgAgACCAACCCggTAAg-3'

(II) Modification of Polylinker Region

The polylinker region was modified by simple insertion of a ds-DNA adapter at the existing EcoRI site. Additional recognition sites thus introduced are: XhoI, NotI and EcoRV (EcoRV is deleted upon insertion of the stuffer fragment (see below)).

ds-DNA adapter:

(SEQ ID NO:16)
5'-AATTCTCGAGCGGCCGCGATATCG-3'

(SEQ ID NO:17)
3'-GAGCTCGCCGGCGCTATAGCTTAA-p-5'

(III) Stuffer fragment insertion

An approximately 690 bp fragment was inserted between the NotI and SalI sites of the modified vector (see vector sequence in FIG. 10). This facilitated the production of NotI/SalI double-digested vector, as the stuffer can be clearly visualized and excised during gel-purification.

The linearized plasmid was gel purified.

1-7-2 The cDNA was ligated to the pGIS1 vector overnight and the constructs were transferred into electrocompetent *E. coli* TOP10 cells by electroporation according to standard techniques (see Sambrook and Russel, 2001, as above).

1-8. Library QC (QC=Quality Check)

A dilution series of 1-100 μL of transformants was plated out onto LB agar plates with antibiotic selection. The colonies were incubated overnight and counted to determine the library titer.

Between 24 to 96 colonies (arbitrary numbers) were picked and the inserts size determined by direct colony PCR and agarose gel electrophoresis (according to standard techniques, eg. Sambrook and Russel, 2001, see above). The percentage of cDNA insert and the average insert size were estimated.

At this stage, the GIS full-length cDNA library may be stored as ligation reactions or as transformants in *E. coli* cells, according to standard methodology (Sambrook and Russel, 2001, see above).

Example 2

2. GIS Ditag Library

The cDNA clones made from steps 1-1 to 1-8 contained a MmeI site (TCCGAC) at the 5 side and another MmeI site (TCCAAC) in reverse orientation at the 3 end. Note that these two MmeI recognition sites are two isoforms that can be recognized by MmeI (TCCRAC 20/18, where R=(A/G)). The sequence difference here will be useful later for directional indication. MmeI restriction enzyme will cleave these clones 20 bp into the cDNA fragments from their 5 and 3 ends. Consequently, despite the variable sizes of the digested cDNA, the vector plus the 20 bp cDNA signature tags on each end of all clones will be of a constant size that can be easily recognized upon agarose gel electrophoresis, and can be easily purified from the unwanted cDNA fragments.

The gel-purified vector plus tags can then be self-ligated to give a agged plasmid containing the 5 and 3 GIS signature tags.

2-1. Plasmid Preparation

The GIS full-length cDNA library was amplified once by plating an appropriate number of clones on large (22×22 cm) agar plates (Genetix). The number of colonies required was determined by the estimated transcriptome size. After an overnight 37 C incubation, the resultant bacterial colonies were harvested and pelleted by centrifugation at 3000 g for 30 min. Plasmid DNA preparation was performed using the Qiagen HiSpeed Plasmid Maxi kit. The quality of the DNA obtained was examined by agarose gel electrophoresis and restriction digestion. Approximately 300,000 colonies can be processed to yield at least 1 mg of plasmid DNA.

2-2. MmeI Digestion

Approximately 10 µg of plasmid DNA was digested using MmeI as per manufacturer's conditions (NEB), ensuring that the number of units of enzyme used was always less than 4-fold excess to prevent methylation-induced inhibition. Digestion proceeded at 37° C. for 2-6 hrs.

Figure 4:
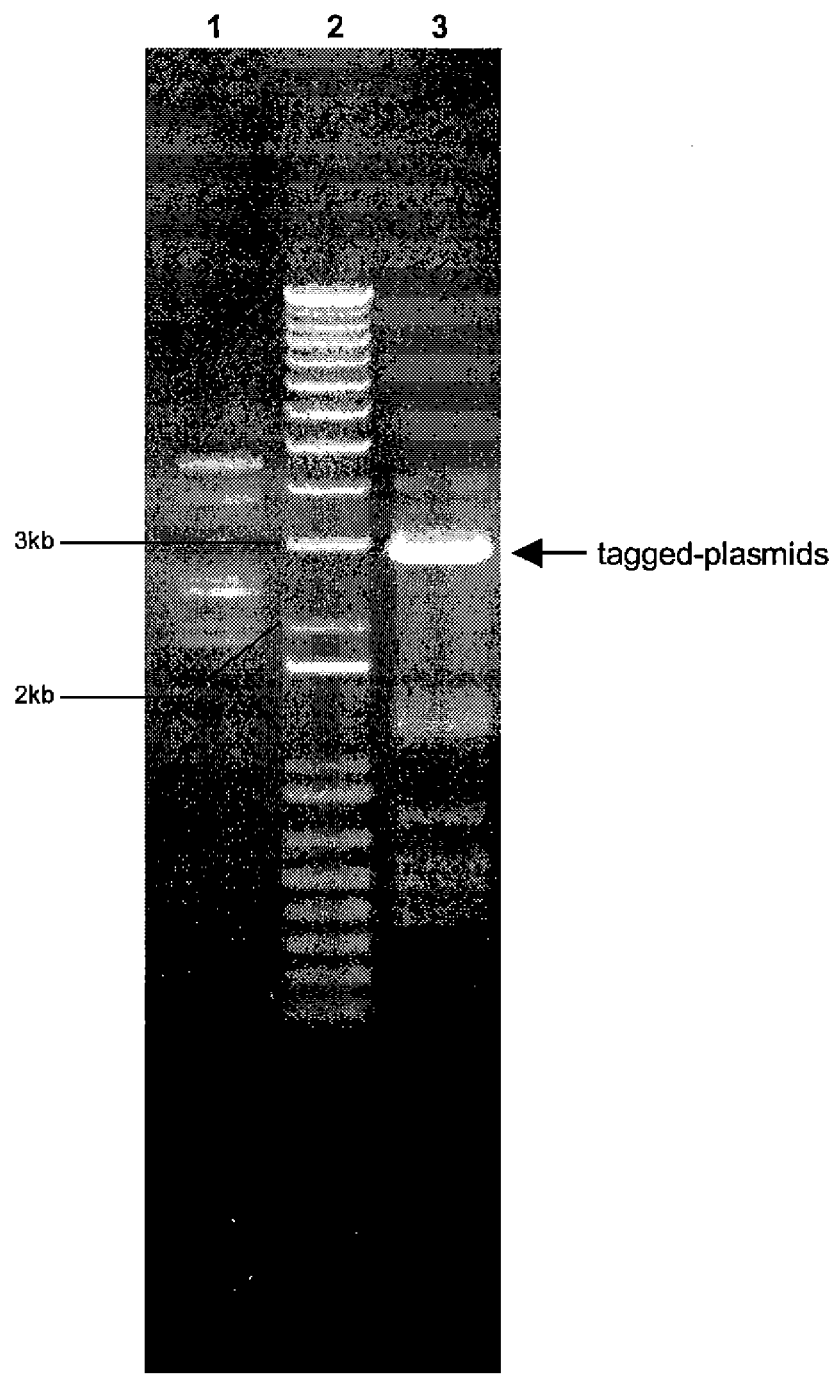
FIG. 4 is an electrophoresis gel showing MmeI digestion of a mix of original full-length cDNA clones. Lane 1: original supercoiled plasmid preparation. Lane 2: 1 kb DNA ladder. Lane 3: MmeI digestion products. The arrowhead shows the position of all the linearized tagged-plasmids.

An aliquot of the digestion reaction was examined on an agarose gel: a strong band of approximately 2800 bp in size corresponding to the linearized vector containing the GIS signature tags were easily observed, together with a number of fragments derived from the excision of cDNA from the original plasmids (see FIG. 4).

2-3. Linear Vector-GIS Ditag Purification

The digestion reaction was electrophoresed on 0.7% agarose, and the 2800 bp vector-GIS tag band was excised and purified using the Qiagen agarose gel extraction kit.

2-4. Vector-GIS Ditag Self Ligation to Create Agged-plasmids

MmeI digestion resulted in a 2 bp overhang on both the 5 and 3 signature tags. These were removed (polished off) using T4 DNA polymerase (Promega), leaving behind 18 bp tags:

| | |
|---|---|
| (0.5-2.0 ug) DNA | 50 µL |
| 10× Y+/TANGO buffer (Fermentas) | 6.0 µL |
| 0.1M DTT | 0.3 µL |
| T4 DNA polymerase | 5 units/µg |
| 10 mM dNTP | 0.6 mL |
| ddH$_2$O | to 60.0 µL |

Incubated at 37° C., for 5 min, then inactivate at 75° C. for 10 min

The purified, blunted DNA was then ethanol precipitated and resuspended at a concentration of approximately 20 ng/µl. Self-ligation (intramolecular recircularization) was carried out as follows:

| | |
|---|---|
| Approx. 350 ng DNA | 15.0 µL |
| Ligation Solution I (Takara Ligation Kit 2) | 15.0 µL |

Incubated at 16° C., 2 hours to overnight 2-5. Creation of Di-signature Tags (Ditags)

The goal of this step was to obtain the GIS di-signature tags in a form quantitatively representative of the original cDNA library from which the tagged-plasmids were derived.

Structure of a Generic 50 bp Cohesive Ditag

```
                                                   (SEQ ID NO:12)
5'-GATCCGACXXXXXXXXXXXXXXXXXXNNNNNNNNNNNNNNNNNNAAG
TTG (SEQ ID NO:13)
5'-GCTGXXXXXXXXXXXXXXXXXXXXNNNNNNNNNNNNNNNNNNNTTCAACC
TAG-5'
```

Wherein X and N may be any of A, C, G or T.

We used two approaches to this:
(i) Bacterial transformation, tagged-plasmid purification and restriction digest to release 50 bp cohesive ditags;
(ii) Direct PCR on the ligation reaction followed by restriction digest of the PCR products to release 50 bp cohesive ditags.

2-5-1 Transformation and Propagation; Preparation of Tagged-plasmids (See FIG. 1)

1 µl of the ligation reaction (Section 2-4) were transformed per 50 µl of electrocompetent TOP10 cells (Invitrogen) by electroporation. Recovered in 1 ml SOC media at 37° C. for 1 hour, then plated out several dilutions on LB agar+ampicillin for QC and titering.

QC (Quality Check): plasmid DNA was prepared from several colonies and tested by digestion with BamHI: tagged-plasmids release a 50 bp cohesive ditag.

This process was then scaled-up by plating the remaining culture on large agar plates, and performing maxipreps using Qiagen HiSpeed Plasmid Maxi kit.

As an example, approximately 5,000 colonies was processed to yield at least 40 ug of tagged-plasmid DNA.

Figure 5:
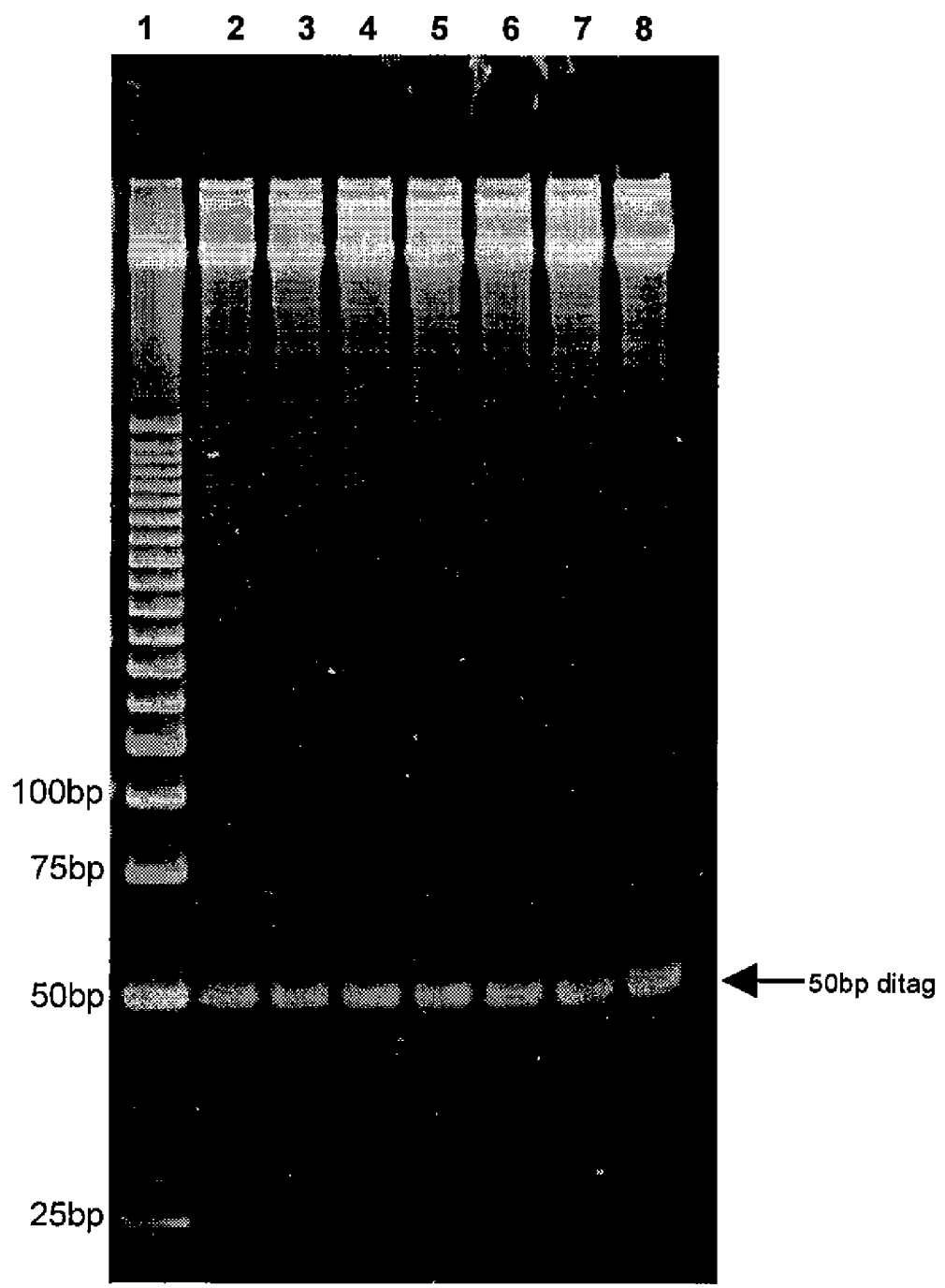
FIG. 5 is an electrophoresis gel related to the preparation of GIS ditags. The plasmid DNA of GIS ditag library is digested with BamHI. The 50 bp ditag fragments are separated and purified from the vector using a 10% polyacrylamide gel. Lane 1: DNA size markers. Lane 2-8: formation of 50 bp GIS ditags.

This plasmid DNA was then BamHI-digested to generate 50 bp cohesive ditags (see FIG. 5 as example result).

2-5-2 PCR-based Retrieval of Cohesive Ditags (See FIG. 2)

PCR was performed on the ligation reaction using primers PMR003 and PMR004 that bind to vector sequences flanking the ditags.

PMR003: 5'-gtaaaacgacggccagt-3' (SEQ ID NO:7)

PMR004: 5'-ggaaacagctatgaccatg-3' (SEQ ID NO:8)

The amount of starting material was determined empirically by doing a series of dilutions and choosing the conditions that result in a clean, specific PCR product of approximately 200 bp

| (e.g. 1:200) diluted ligation reaction | 5.0 µL |
|---|---|
| 10× HiFi buffer | 2.0 µL |
| 10 mM dNTP | 0.4 µL |
| PMR003 (100 ng/µL) | 1.0 µL |
| PMR004 (100 ng/µL) | 1.0 µL |
| Eppendorf TripleMaster polymerase | 0.2 µL |
| dH2O | 10.4 µL |

(the HiFi buffer was the reaction buffer provided with the Eppendorf

TripleMaster enzyme)

Thermo-cycling conditions:
  Step 1: 95° C.×2 min
  Step 2: 95° C.×30 sec
  Step 3: 55° C.×1 min
  Step 4: 72° C.×30 sec
  Go to step 2, repeat steps (2-4) 24×
  Step 5: 72° C.×4 min
  16° C. forever The PCR products were analyzed on a 1.5% agarose gel.

Figure 6:
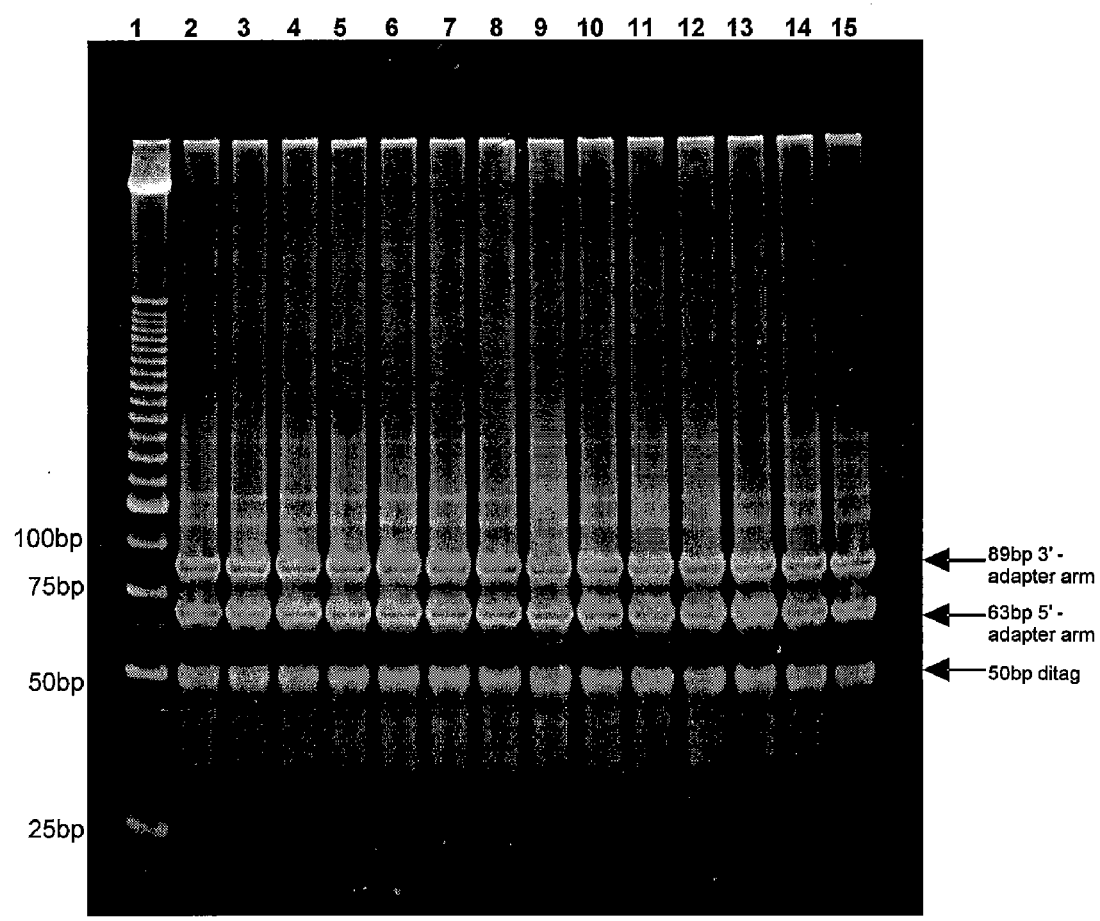
FIG. 6 is an electrophoresis gel related to the preparation of GIS ditags by PCR. The ditag-containing PCR fragments generated from the GIS full-length cDNA library are digested by BamHI. The 50 bp ditag fragments are separated and purified from adaptor arms in 10% polyacrylamide gel. Lane 1: DNA size markers. Lane 2-15: large scale preparation of 50 bp GIS ditags.

For negative controls, the PCR reaction was performed using (i) no template, and (ii) no ligase. To obtain sufficient 200 bp PCR product for subsequent 50 bp cohesive ditag production, the reaction was scaled-up: do 96 PCR reactions using a 96-well PCR plate; this generates approx. 50 ug of 200 bp ditag. The individual PCR reactions are then combined and ethanol precipitated before Bam HI digest to generate 50 bp cohesive ditags (see FIG. 6 as an example result).

3. GIS Library 3-1. Tagged-plasmid Preparation

This applies only to the bacterial transformation-based approach (see Section 2-5-1).

3-2. BamHI Digestion and Purification of GIS Tags 3-2-1 BamHI Digestion of Tagged-plasmids (Section 2-5-1) Released 50 bp Cohesive Ditags:

| DNA (tagged-plasmids) | 40 µg |
|---|---|
| 10× unique BamHI buffer (NEB) | 100 µL |
| 100× BSA | 10 µL |
| BamHI (20 U/µL, NEB) | 10 µL |
| dH2O | to 1 mL |

The choice of value of 40 µg of DNA (tagged-plasmids) was arbitrary.

Aliquots were divided into 10×100 ul for more efficient digestion, and incubated at 37° C., for 4 hours.

After digest, they were inactivated at 65° C., for 15 minutes, then phenol-chloroform extraction and ethanol precipitation were performed. Then, the pellet comprising 50 bp cohesive ditags and the rest of the cleavage products after the BamHI digest was resuspended in LoTE buffer for gel-purification.

3-2-2 BamHI Digestion of or 200 bp Ditags Retrieved by PCR (Section 2-5-2) Released 50 bp Cohesive Ditags:

| DNA (PCR products) | 40 µg |
|---|---|
| 10× unique BamHI buffer (NEB) | 100 mL |
| 100× BSA | 10 µL |
| BamHI (20 U/µL, NEB) | 10 µL |
| dH2O | to 1 mL |

The choice of value of 40 µg of DNA (tagged-plasmids) was arbitrary.

Aliquots were divided into 10×100 ul for more efficient digestion, incubated at 37° C., for 4 hours.

After digest, they were inactivated at 65 C, for 15 min, then phenol-chloroform extraction and ethanol precipitation were performed. Then, the pellet comprising 50 bp cohesive ditags and the rest of the cleavage products after the BamHI digest was resuspended in LoTE buffer for gel-purification.

3-3 Gel-purification of 50 bp Cohesive Ditags

The BamHI-digested DNA according to both section 3-2-1 or 3-2-2 was separated on a large (Hoefer Ruby 600, 15×15 cm, 1.5 mm thick) 10% polyacrylamide gel. Electrophoresis proceeded at 200V for approx. 2 hrs until the Bromophenol Blue (standard tracking dye) band almost reached the bottom of the gel. The gel was stained in SYBR Green I (Molecular Probes, Inc.) for 30 min before visualisation and excision of the 50 bp cohesive ditags.

At this stage it is convenient not to load more than 5 µg per lane, or fluorescence quenching occurs.

The 50 bp cohesive ditags were excised and collected into 0.6 ml microfuge tubes (2 gel pieces per tube) which have been pierced at the bottom with a 21 G needle. This pierced tube was placed inside a 1.7 ml microfuge tube, and centrifuged at 12 Kg, 4° C. for 2-5 minutes. The gel pieces were thus shredded and collected in the 1.7 ml tube.

150 µl of LoTE:NH4OAc (125:25) were added to each tube and left overnight at 4° C. to elute. The next day, the eluate was collected with the aid of microspin filter units (SpinX, Costar), and ethanol precipitation performed to retrieve the purified 50 bp ditags, which were resuspended in LoTE. Starting from 70 µg 200 bp ditag, we expected to retrieve several hundred ng of 50 bp ditag.

3-4. Ditag Concatenation and Gel-purification

Some optimization (ligation time, amount of starting material) may be necessary to ensure that the concatenation of the 50 bp ditags results in a smear of products ranging from approx. 300 bp to >1000 bp. The conditions below are suggested as a starting point:

| 50 bp cohesive ditags | 150-500 ng |
|---|---|
| 5× buffer (with PEG; BRL) | 2.0 µL |
| T4 DNA ligase (5 U/µL) | 1.0 µL |
| dH2O | to 10 µL |

Incubated at 16° C. for 1 hour

Loading buffer was added and the entire sample heated at 65° C. for 15 minutes. The sample loaded in a single well of an 8% polyacrylamide minigel and run at 200V for about 1 hour, or until Bromophenol Blue was about 2 cm from bottom.

The smear of ligation products can be excised as 2 or more fractions, eg. 200-500 bp; 500-1000 bp; >1000 bp.

Elution of DNA from the gel pieces was performed as detailed in Section 3-3. The eluate was extracted with phenol-chloroform then ethanol precipitated. Resuspend the DNA pellet in 6 ul LoTE.

3-5. Cloning of Concatemers

Figure 8:
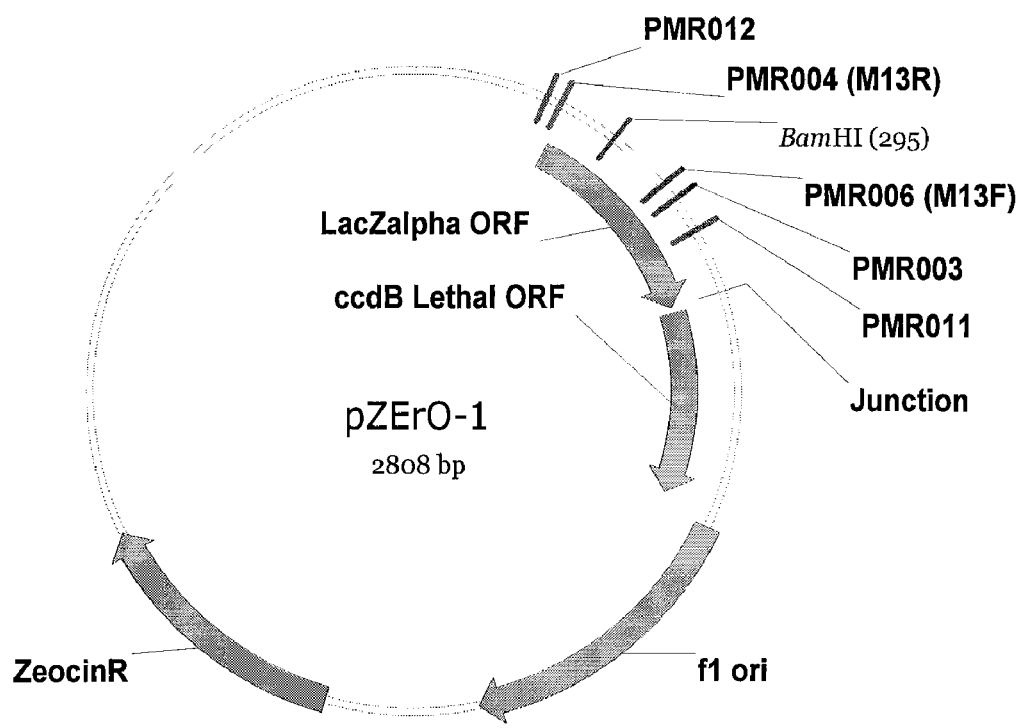
FIG. 8 shows the commercial pZErO-1 vector construct (Invitrogen) The positions of the various sequencing/PCR primer binding sites (PMR003, PMR004, PMR011 and PMR012) are shown.

The cloning vector was prepared by digesting 2 ug of pZErO-1 plasmid DNA (Invitrogen) (FIG. 8) (FIG. 8 shows the sequencing/PCR primer binding sites) with 10 units of BamHI for 3 hours at 37° C. The digested DNA was phenol-chloroform extracted and ethanol precipitated, then resuspended in LoTE at a concentration of 33 ng/µl. The ligation reaction was performed as follows:

| | |
|---|---|
| Concatemer DNA | 6.0 µL |
| BamHI/pZErO-1 | 1.0 µL |
| 5× ligase buffer | 2.0 µL |
| T4 DNA ligase (5 U/µL) | 1.0 µL |

Incubated at 16° C. overnight.

The vector self-ligation was also performed in parallel as a control.

The ligation products were purified before electroporation. The phenol-chloroform extraction was followed by ethanol precipitation; the pellet was washed 3 times with 75% ethanol before re-suspending in 12 µl TE (0.1X). 1 µl of this DNA was used to transform 50 µl of electro-competent TOP10 bacterial cells. After recovery (see also Section 2-5-1), 50 µl were plated on a small agar plate (containing Low Salt LB agar (Lennox L) plus Zeocin (50 µg/ml) and IPTG (50 µg/ml) and incubated overnight at 37 C. As a background control, bacteria were plated out that have been similarly transformed with the vector self-ligation reaction above. (IPTG is optional when using TOP10 cells but may reduce background).

3-6. GIS Library QC (Quality Check)

The following day, 10-30 colonies were picked to check for insert size by PCR. For each reaction, a single colony was picked into a PCR tube containing:

| | |
|---|---|
| 10× HiFi buffer | 2.0 µL |
| 10 mM dNTP | 0.4 µL |
| PMR003 (100 ng/ul) | 1.0 µL |
| PMR004 (100 ng/ul) | 1.0 µL |
| Eppendorf TripleMaster polymerase | 0.2 µL |
| dH2O | 11.4 µL |

Thermo-cycling Conditions:

| | |
|---|---|
| Step 1: | 95° C. × 2 min |
| Step 2: | 95° C. × 30 sec |
| Step 3: | 55° C. × 1 min |
| Step 4: | 72° C. × 3 min |
| Go to step 2, repeat steps (2-4) 24× | |
| Step 5: | 72° C. × 4 min |
| 16° C. forever | |

The PCR products were visualized on 1% agarose gel. A typical result is shown in FIG. 9.

The primer pair PMR003/PMR004 (SEQ ID NO:7/SEQ ID NO:8) gives a band of approx. 220 bp in the absence of any cloned insert. If the quality of the library thus produced appears good, the remaining transformation mixture can be plated out (Section 3-5) on large agar plates in preparation for DNA sequencing analysis.

The primer pair PMR003/PMR004 is also convenient for checking the quality of the library, but for the actual preparation of PCR templates for sequencing, primer pair PMR012/PMR003 (SEQ ID NO:11/SEQ ID NO:7) were preferred (see Section 4-2).

```
                                              (SEQ ID NO:11)
PMR012:  5'-AGCGGATAACAATTTCACACAGG-3'.
```

4. Sequencing Analysis of GIS Tags 4-1. Library Plating and Colony Picking

The transformed TOP10 (Invitrogen) bacteria cells were plated out on 22×22 cm agar plates with colony density less than 3,000 per plate. Individual colonies were picked and cultured in 384-well plates with LB plus Zeocin (see above in section 3.5) at 37° C. overnight. Multiple copies of 384-well plates are replicated and stored in −80° C.

4-2. Template Preparation

Bacterial cultures in 384-well plates were inoculated in pre-mixed PCR cocktails. PCR was performed using primer pair PMR012/PMR003.

This primer pair gives a band of 245 bp in the absence of any concatemer insert. Nonetheless, this set of primers is preferred as it allows the use of sequencing primers PMR004 (M13 reverse; 68 bp from BamHI site) and PMR006 (SEQ ID NO:9) (M13 forward; 87 bp from BamHI site).

```
                                              (SEQ ID NO:9)
PMR006:  5'-TAATACGACTCACTATAGGG-3'
```

4-3. Sequencing

PCR templates were sequenced using the sequencing primers PMR004 and PMR006 to sequence in both directions.

Example 3

Experimental Summary

Our experimental strategy (FIG. 13) was to directly clone p53 ChIP-enriched DNA into a plasmid vector for GIS analysis. This preserves the information content of the experiment in an infinitely renewable format. GIS ditag sequences representing the ChIP DNA fragments can then be mapped to the genome to define the genome regions corresponding to the original ChIP-enriched material. Relative tag counts will allow the distinguishing regions of interest from the (inevitable) nonspecific background.

For this study, we used the colorectal cancer cell line HCT116 (ATCC CCL-247), which contains wildtype p53. The cells were treated with genotoxic 5-Fluorouracil (5-FU) to activate p53 and induce target gene expression. At different time points before and after 5-FU treatment, the cells were treated with 1% formaldehyde for 10 min at room temperature. Formaldehyde was inactivated by addition of 125 mM glycine. After lysis and sonication, chromatin extracts containing DNA fragments of an average size of 500 bp were immunoprecipitated using Protein A-Sepharose and anti-p53 DO1 monoclonal antibody. Immunoprecipitated material was eluted from the Sepharose beads, then cross-linking was reversed by heating. Purification of the final ChIP-enriched DNA was achieved by phenol-chloroform extraction and ethanol precipitation.

Figure 13:
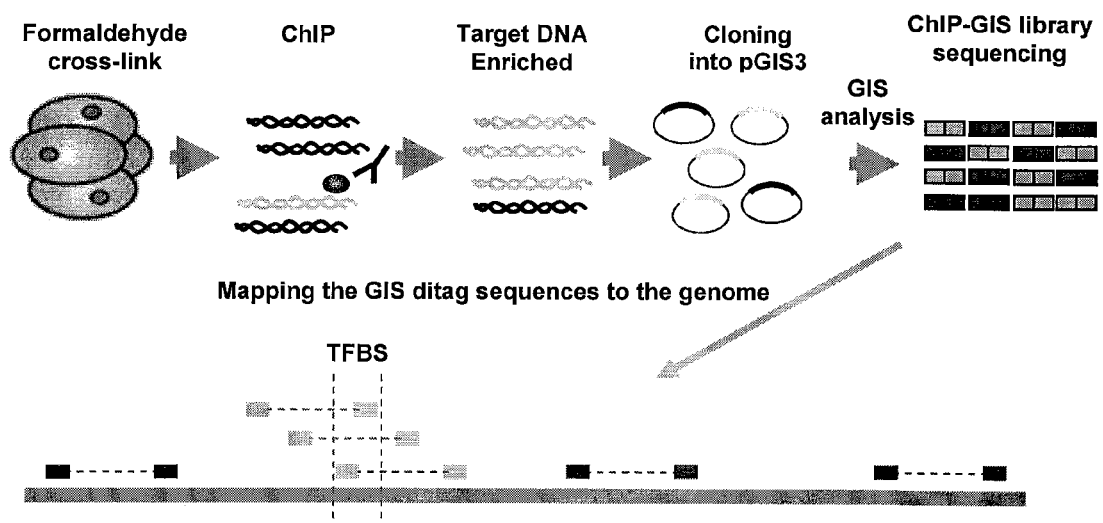
FIG. 13 shows the combined Chromatin Immunoprecipitation-Gene Identification Signature (ChIP-GIS) Analysis procedure. TFBS, transcription factor binding site.

To avoid amplification-induced bias, the ChIP-enriched DNA was directly cloned into pGIS3 (FIG. 14, FIG. 17 and SEQ ID NO:22), and transformed into bacteria to give the ChIP-GIS library (FIG. 13). Plasmid DNA prepared from the ChIP-GIS library was digested with MmeI to excise all of the inserted ChIP DNA except for the original 5'- and 3'-most 20 bp. After end-polishing and plasmid recircularization, the recircularized plasmids (each now containing one GIS ditag of 36 bp) were transformed into bacteria to give the GIS single-ditag library. Plasmid DNA was extracted from the GIS single-ditag library and digested with BamHI to liberate all the ditags, which were gel-purified, blunted with Mung Bean nuclease, then concatenated overnight using T4 DNA ligase. The following day, the concatenated GIS ditags were separated by gel electrophoresis, and various size fractions were excised and cloned into pZErO-1, thereby forming the GIS ditag library, from which plasmid was extracted and sent for sequencing analysis. Following standard Sanger dideoxy sequencing of clones from the GIS ditag library, ditag information was extracted from the raw sequences, and mapped onto the human genome assembly (UCSC hg17 build, May 2004) for visualization using a custom-designed genome browser called "T2G browser."

Detailed Experimental Methods

The colorectal cancer cell line HCT116 (ATCC CCL-247) and its derived isogeneic p53 (−/−) cell line were a gift from Dr Bert Vogelstein, Johns Hopkins University, Baltimore, Md. Cells were cultured in Dulbecco's modified Eagle's medium containing 10% fetal calf serum. All culture reagents and media were from Invitrogen. 5-Fluorouracil (5-FU) was purchased from Sigma. The cells were treated with 0.1M 5-FU to activate p53 and induce target gene expression.

Chromatin Immunoprecipitation

At different time points before and after 5-FU treatment, the cells were mixed with 1% formaldehyde for 10 minutes at room temperature. Formaldehyde was then inactivated by addition of 125 mM glycine and further incubation for 5 minutes. Cells were collected and washed with ice-cold PBS three times, cell lysis buffer (10 mM Tris-Cl pH 7.5, 10 mM NaCl, 0.5% NP-40, 1 mM PMSF) three times, and resuspended in SDS lysis buffer (10 mM Tris-HCl pH 7.5, 150 mM NaCl, 1% SDS, 1 mM EDTA). The cells were disrupted by sonication on ice. The chromatin solution was clarified by centrifugation at 15,000 g at 4° C. for 10 minutes. The average DNA fragment size was 500 bp. The chromatin solution was diluted with IP dilution buffer (20 mM Tris-Cl pH 8, 1 mM EDTA, 1% Triton X-100, and 150 mM NaCl, protease inhibitors) and pre-cleared with protein A-Sepharose beads for 15 minutes. The pre-cleared diluted chromatin sample was incubated with 10 μl of anti-p53 DO1 mAb (Santa Cruz Biotechnology) for 3 hr followed by the addition of protein A-Sepharose beads for an additional 3 hours. The beads were washed once with the IP dilution buffer, twice with 20 mM Tris-Cl pH 8, 2 mM EDTA, 1% Triton X-100, 150 mM NaCl, 1 mM PMSF, once with 20 mM Tris-Cl pH 8, 2 mM EDTA, 1% Triton X-100, 0.1% SDS, 500 mM NaCl, 1 mM PMSF, and once with 10 mM Tris-Cl pH 8, 1 mM EDTA, 0.25 M LiCl, 1% NP-40, 1% deoxycholate. The immunoprecipitated material was eluted from the beads by heating for 15 minutes at 65° C. in 25 mM Tris-Cl (pH 7.5), 10 mM EDTA, 0.5% SDS. To reverse the crosslinks, samples were incubated with 1.5 μg/ml Pronase at 42° C. for 2 hr followed by 65° C. for 5 hours. The samples were then extracted with phenol-chloroform-isoamyl alcohol, followed by chloroform, then ethanol precipitated in the presence of glycogen, and resuspended in TE buffer (10 mM (pH 7.5) Tris-Cl and 1 mM EDTA). The p53 binding site enrichment level was determined by quantitative real-time PCR as described below.

Quantitative PCR Verification of GIS Analysis Identified p53 Binding Sites

For all ChIP experiments, quantitative PCR analyses were performed in real time using the ABI PRISM 7900 Sequence Detection System. Reactions were carried out in 10 μl using SYBR green PCR master mix according to the manufacturer's protocol. Cycling was for 10 min at 95° C., followed by 40 cycles of 95° C., 30 s, 60° C., 45 s, 72° C., 45 s. The fold-enrichment value for each transcription factor bound to a particular region of DNA was estimated as V+/V−. V+ was calculated by subtracting the cycle threshold (Ct; defined as the cycle at which the fluorescence signal is statistically significant over background) average of input DNA from the Ct average for the immunoprecipitated DNA; this net Ct value was then used as an exponent for the base n (n being the mean primer slope). The same procedure was repeated to obtain the negative control region value (V−).

GIS Analysis of ChIP-enriched DNA/

Description of the pGIS3 Plasmid

The ChIP-enriched DNA was directly cloned into pGIS3 (FIG. 14 and FIG. 17), and transformed into bacteria to give the ChIP-GIS library (FIG. 13). pGIS3 is a plasmid vector derived from pGIS1 described earlier, which was in turn derived from commercially available pGEM3z (Promega), which has had its 2 original MmeI recognition sites eliminated by site-directed mutagenesis using the Quick-Change Multi kit (Stratagene). This was necessary to facilitate the subsequent enzymatic excision of unwanted regions of the inserted DNA by the same Type II restriction enzyme. Further recombinant DNA manipulations were performed to introduce the insert sequence (FIG. 17 and SEQ ID NO:22) comprising in series the restriction sites NotI, BseRI, BamHI, MmeRI, XhoI in the sense orientation, followed by MmeRI, BamHI, BseRI and SalI in the antisense orientation. Prior to use, pGIS3 was linearized using XhoI, then treated with Mung Bean nuclease at the concentration of 5 U/μg DNA for 10 minutes at 37° C., thereby removing all single-stranded overhangs to leave a blunt-ended cloning site directly flanked by 2 MmeI recognition sequences (FIG. 14). Instead of XhoI, any other suitable restriction endonuclease recognition site can be substituted (as long as it is absent from the remainder of the vector backbone), the sole purpose of this being to open up the vector at that point, thereby allowing the insertion of the fragment of interest between the 2 Type II restriction enzyme recognition sites. Similarly, instead of MmeI, any other suitable enzyme that cuts at a distance from its recognition sequence can be substituted. After dephosphorylation with shrimp alkaline phosphatase to prevent vector self-ligation, the plasmid was purified by phenol-chloroform extraction and resuspended in TE buffer at a concentration of 40 ng/μl, ready for use. Between 100 to 200 ng of ChIP-enriched DNA was first end-polished and phosphorylated using a mixture of T4 DNA polymerase and T4 polynucleotide kinase present in the End-It repair kit (Epicentre). After phenol-chloroform extraction, the entire amount of DNA was ligated to 40 ng of prepared pGIS3, and incubated overnight at 16° C. The following day, the ligation mixture was phenol-chloroform extracted, resuspended in 10 μl TE, and 1 μl was used to transform 25 μl of electrocompetent TOP10 E. coli bacteria (Invitrogen).

Approximately 5-10 μg of plasmid DNA prepared from the ChIP-GIS library was digested using MmeI as per the manufacturer's conditions (NEB), ensuring that the number of units of enzyme used was always less than 4-fold excess, to prevent methylation-induced inhibition. The MmeI digestion was performed at 37° C. overnight, to excise all of the inserted ChIP DNA except for the original 5'- and 3'-most 20 bp.

The entire digestion reaction was electrophoresed on 0.7% agarose, and the 2800 bp vector-GIS single ditag bands were excised and purified from the agarose gel using the Qiagen gel extraction kit. MmeI digestion results in a 2-base 3'-overhang on both the 5' and 3' signature tags. These were removed by end-polishing using T4 DNA polymerase at a concentration of 5 U/µg DNA, leaving behind 18 bp blunt-ended tags. Intramolecular ligation was performed to recircularize the purified DNA, which was then transformed into bacteria to give the GIS single-ditag library.

At least 100 g of plasmid DNA extracted from the GIS single-ditag library was digested with BamHI to release all the ditags, which were gel-purified using a 4-20% TBE PAGE minigel followed by electroelution in Midi ElutaTubes (Fermentas). The GIS ditags were blunted with Mung Bean nuclease as described above, then concatenated overnight using T4 DNA ligase.

As an alternative, the BseRI sites within pGIS3 were designed to allow the release of GIS ditags using BseRI; in this case, there is no need to perform Mung Bean nuclease blunting. Instead, following gel extraction, the BseRI-derived ditags can be concatenated directly.

The following day, the concatenated GIS ditags were separated by gel electrophoresis using 4-20% TBE-PAGE, and various size fractions (typically 0.4-1 kb; 1-2 kb; and >2 kb) were excised, electroeluted, and cloned into pZErO-1, thereby forming the GIS ditag library. If BseRI-derived ditags had been used, the concatenated DNA must be end-polished using T4 DNA polymerase before gel electrophoresis.

Individual clones from the GIS ditag library were picked for plasmid extraction, and the plasmid DNA sequenced using standard universal M13 forward primer. Following Sanger dideoxy sequencing of clones from the GIS ditag library, ditag information was extracted from the raw sequences, and mapped onto the human genome (UCSC hg17).

Data Analysis

Ditag Extraction

GIS ditags were extracted from the raw sequences obtained from each clone of the GIS ditag library. Traces were base-called with Phred/Phrap using a minimal quality score of 20, and the flanking pZErO-1 vector sequences were trimmed from the sequence reads. The extraction parameters included the 5' vector/insert sequence junction; the internal spacer sequence between ditags; the 3' vector/insert junction; minimal ditag length, 34 bp; maximal ditag length, 40 bp.

Ditag-to-genome Mapping Analysis

Compressed Suffix Array (CSA) is a compressed and advanced index data structure that allows efficient pattern searching (Grossi and Vitter, in *Thirty-second annual ACM symposium on Theory of computing*. 2000. Portland, Oreg.). Unlike BLAT (Kent W. J., Genome Res, 2002.12(4): p. 656-64) and BLAST (Altschul et al., J Mol Biol, 1990. 215(3): p. 403-10), the pattern searching time using CSA depends solely on the query pattern length and is independent of the genome size. CSA is thus theoretically much faster than BLAT or BLAST, especially for short sequences. Preliminary data showed that a CSA-derived alignment algorithm was superior to BLAST in terms of speed while maintaining the same accuracy and completeness of mapping, hence we used this CSA-derived algorithm to map the ditags onto the UCSC human genome database build hg17 in this study.

A minimum 17 bp contiguous match for the 5' tag and a minimum 16 bp for the 3' tag within each GIS ditag when mapping to the genome was mandated. This was empirically determined to give the highest mapping efficiency. Finally, each 5' signature was matched with its cognate 3' signature against existing genome sequence data, the criteria being that both the 5' and 3' signatures must be present on the same chromosome, be on the same strand, and within 4000 bp of genomic distance (to provide some flexibility in mapping, despite the average ChIP fragment size being 0.5 kb). Ditags that failed to meet these criteria were considered "unmappable", and archived separately for additional analysis. Because the blunt-ended cloning used in this procedure does not give any indication of orientation, ditags that were mapped to the same locus but were in sense vs antisense orientations were merged before display.

Ditag Annotation and Display

Once the ditag-to-genome coordinates are defined, we can display each ditag on a browser called "T2G" that is publicly accessible at t2g.bii.a-star. This was designed based on the UCSC genome browser at genome.ucsc.

Results

Using the ditag extraction and mapping parameters defined above in "Detailed Experimental Methods", a total of 228, 845 ChIP-enriched ditags were obtained, of which 84% were found to match various locations in the human genome. The 16% unmapped ditags failed the mapping criteria, either due to mismatches caused by polymorphisms or sequencing error, or other undefined experimental artifacts. Approximately 73% of the 228,845 ditags (169,091 ditags) could be mapped to single, distinct loci in the genome. Subsequent analyses were focused on this group of single-locus matches. Data consolidation (by merging ditags in the same loci but in opposite orientations together) resulted in a final set of 65,714 "merged" single-locus, orientation-independent ditags that were displayed using the T2G genome browser.

Figure 15:
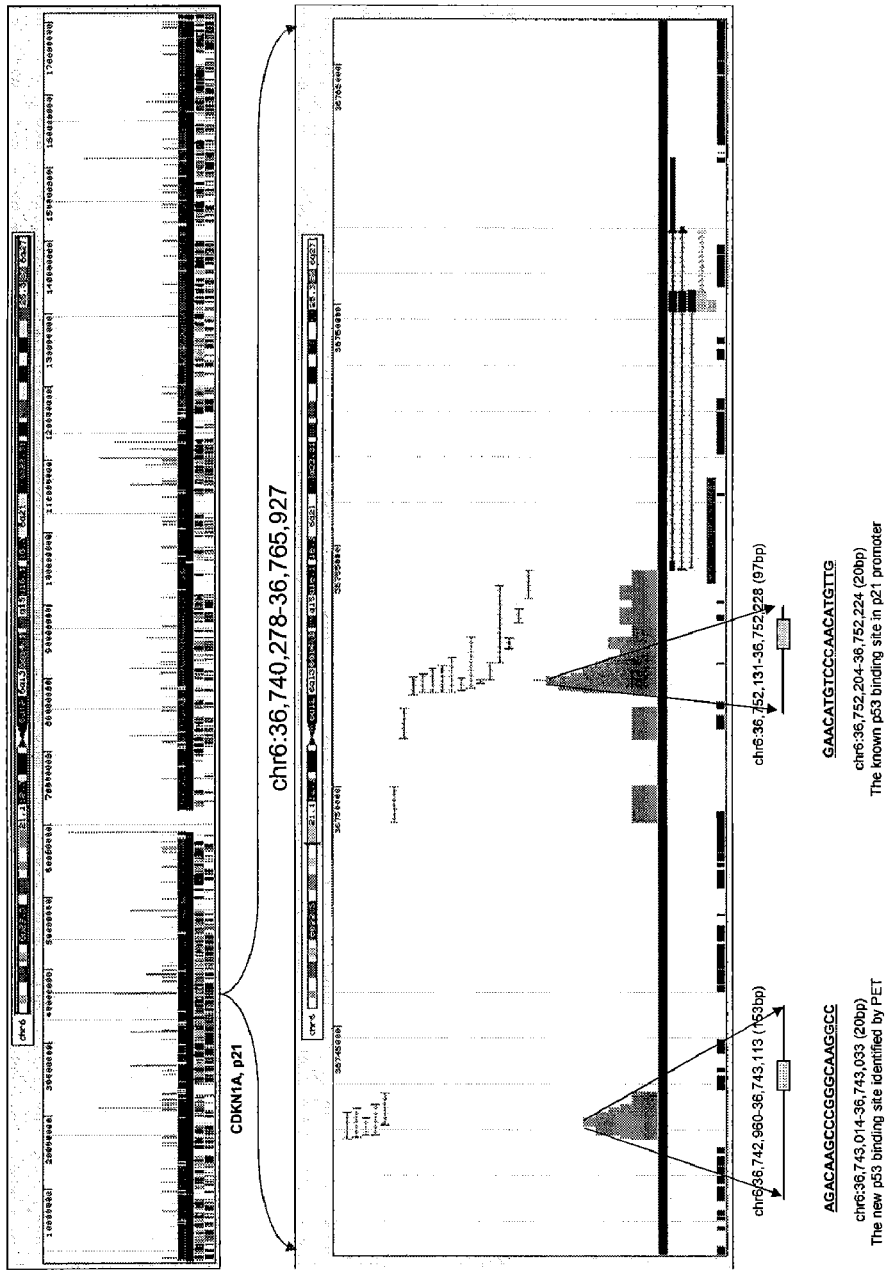
FIG. 15 shows the identification of a known and a novel putative TFBS in the vicinity of p21/Cip1/Waf1. The upper part of the diagram provides an overview of the known genes (darker shaded bars) and CpG islands (lighter shaded bars) along chromosome 6. The peaks represent TFBS density, which is a measure of the frequency of occurrence of a particular region as defined by GIS ditags. The lower part of the figure zooms in on a region of chromosome 6 from 36,740,278-36,765,927 and displays 2 separate clusters of high TFBS density. The zone of highest density within the first cluster, located on Chr6: 36,742,960-36,743,113 (153 bp) is represented by 5 unique ditags, and contains a known p53-responsive promoter site. The second region has the highest density from Chr 6: 36,752,131-36,752,228 (97 bp), and is within a known promoter for the p53-responsive gene p21/Cip1/Waf1.

Preliminary analyses revealed that the expected background of non-specific DNA fragments was very low, and that there were many distinct, highly-represented clusters located throughout the genome. These clusters representing p53 binding regions were studied in detail. Of particular interest were the sequences within each cluster that were contained within multiple overlapping ditags (and therefore would have the highest TFBS density), as these would be the sequences to which p53 would bind most strongly. This was confirmed by the identification of clusters within the promoters of known p53-responsive genes such as p21/Cip1/Waf1 (22) (see FIG. 15), and furthermore by the identification of p53 consensus binding motifs within the promoter region (SEQ ID NO: 20: GAACATGTCCCAACATGTTG, in a 97 bp region from Chr 6: 36, 752, 131-36, 752, 228).

Additionally, novel clusters were also discovered that on closer examination were found to indeed contain p53 consensus binding motifs (FIG. 15) such as the sequence SEQ ID NO:21: AGACAAGCCCGGGCAAGGCC, within Chr6: 36,742,960-36,743,113 (153 bp). Such clusters therefore provide preliminary evidence for the presence of hitherto-unidentified p53-responsive elements.

Figure 16:
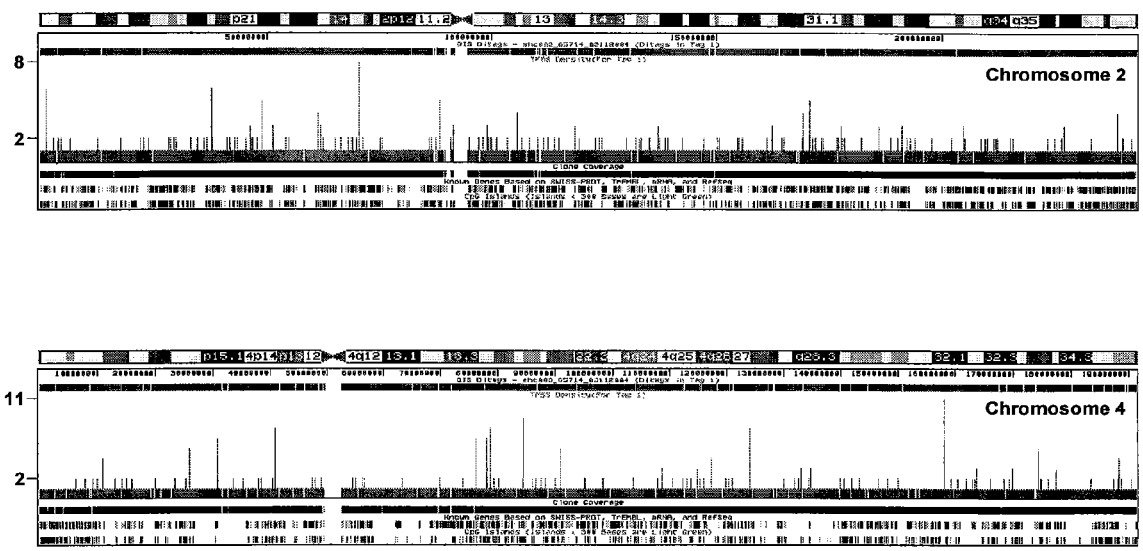
FIG. 16 shows that ChIP-GIS enables the genome-wide survey of all putative p53 binding sites. Here, known genes and CpG islands along chromosomes 2 and 4 are displayed together with regions of GIS ditag-defined TFBS density (shown by the peaks). Regions of high TFBS density therefore represent putative p53 binding sites. The numbers on the vertical axes are a measure of TFBS density, and represent the number of unique ditags within a particular region.

The ChIP-GIS procedure was able to provide a genome-wide survey of all putative p53-binding sites, and coupled with T2G genome browser, allowed the direct visualization of all these binding sites in the context of known genes and CpG islands, as shown for chromosomes 2 and 4 (FIG. 16).

In-depth analysis of data obtained from a genome-wide survey such as this current one may be expected to reveal a wealth of interesting information. In particular, we are seeking evidence for the possibility of non-canonical p53 binding motifs, for indications of the presence of p53-responsive non-coding transcripts that might regulate the expression of sense transcripts to which they overlap, and for evidence of p53 involvement in known promoters.

Applications

The GIS analysis method according to any embodiment of the invention is a complete gene discovery platform. It combines full-length cDNA library construction, cDNA tag sequencing, genome mapping and annotation into one operation from the same starting materials. For example, to study the genes expressed in human stem cells, we start with the stem cell mRNA, construct a stem cell GIS full-length cDNA library, and then the GIS library. We will only need to sequence 50,000 clones of the GIS library to reveal over a million transcripts. Such deep sampling will allow us to capture nearly all unique transcripts expressed in the human stem cell transcriptome. Each of the GIS ditags can be specifically mapped to the genome and therefore define the structural regions of the corresponding genes on the chromosomes. Most of the GIS ditags map to known genes on chromosomes and the counts of the GIS ditags provide the measurement of expression activity. Some of the GIS ditags may map to desert ("no gene") regions of the genome, which may suggest the identification of new genes that are expressed in the stem cell transcriptome. In such a way the genome annotation for genes is further refined by this whole transcriptome-to-whole genome approach. Based on the GIS ditag sequences, these putative new genes can be readily cloned from the original GIS full-length cDNA library.

We can apply this GIS gene discovery system not only to human stem cells, but also to all other biological systems, such as development of cells, tissues and organs of human and model organisms.

REFERENCES

Adams, M., et al., 1991, *Science*, 252, 1651-1656.

Altschul, S. F., et al., *Basic local alignment search tool*. J Mol Biol, 1990. 215(3): p. 403-10.

Antequera, F. and A. Bird, *Number of CpG islands and genes in human and mouse*. Proc Natl Acad Sci USA, 1993. 90(24): p. 11995-9.

Brenner, S., et al., *Gene expression analysis by massively parallel signature sequencing (MPSS) on microbead arrays*. Nat Biotechnol, 2000. 18(6): p. 630-4.

Buck, M. J. and J. D. Lieb, *ChIP-chip: considerations for the design, analysis, and application of genome-wide chromatin immunoprecipitation experiments*. Genomics, 2004. 83(3): p. 349-60.

Bulyk, M. L., *Computational prediction of transcription-factor binding site locations*. Genome Biol, 2003. 5(1): p. 201.

Carninci et al., 1996, Genomics, Vol. 37, 327-336; U.S. Pat. No. 6,143,528.

Cawley, S., et al., *Unbiased mapping of transcription factor binding sites along human chromosomes 21 and 22 points to widespread regulation of noncoding RNAs*. Cell, 2004. 116(4): p. 499-509.

Current Protocols in Molecular Biology, Vol. 2, 1995, Ed. Ausubel, et al., Greene Publish. Assoc. & Wiley Interscience, Unit 3.1.15; New England Biolabs Catalog, 1995

Edery et al., 1995, Mol. Cell. Biol., Vol. 15, No. 6, 3363-3371 el-Deiry, W. S., et al., *WAF1, a potential mediator of p53 tumor suppression*. Cell, 1993. 75(4): p. 817-25.

Euskirchen, G., et al., *CREB binds to multiple loci on human chromosome 22*. Mol Cell Biol, 2004. 24(9): p. 3804-14.

Grossi, R. and J. S. Vitter. *Compressed suffix arrays and suffix trees with applications to text indexing and string matching (extended abstract)*. in *Thirty-second annual ACM symposium on Theory of computing*. 2000. Portland, Oreg.

Hadi, S. M., et al., J. Mol. Biol. 134: 655-666 (1979).

Hussain, S. P. and C. C. Harris, *Molecular epidemiology of human cancer: contribution of mutation spectra studies of tumor suppressor genes*. Cancer Res, 1998. 58(18): p. 4023-37.

Iyer, V. R., et al., *Genomic binding sites of the yeast cell-cycle transcription factors SBF and MBF*. Nature, 2001. 409(6819): p. 533-8.

Jongeneel C. V., et al., 2003, Proc Natl Acad Sci USA. 100, 4702-4705.

Kaeser, M. D. and R. D. Iggo, *Chromatin immunoprecipitation analysis fails to support the latency model for regulation of p53 DNA binding activity in vivo*. Proc Natl Acad Sci USA, 2002. 99(1): p. 95-100.

Kent, W. J., *BLAT—the BLAST-like alignment tool*. Genome Res, 2002. 12(4): p. 656-64.

Kim, E. and W. Deppert, *The complex interactions of p53 with target DNA: we learn as we go*. Biochem Cell Biol, 2003. 81(3): p. 141-50.

Li and Chandrasegaran, Proc. Nat. Acad. Sciences USA 90:2764-8, 1993.

Lieb, J. D., et al., *Promoter-specific binding of Rap1 revealed by genome-wide maps of protein-DNA association*. Nat Genet, 2001. 28(4): p. 327-34.

Mao C., et al., 2000, *Proc Natl Acad Sci USA*, 97, 1665-1670.

Matsumura H, et al., Gene expression analysis of plant host-pathogen interactions by SuperSAGE, Proc Natl Acad Sci USA. 2003 Dec. 23;100(26):15718-23.

Moencke-Buchner, E., et al., J. Biotechnol. 114: 99-106 (2004).

Mucke, M., et al., J. Mol. Biol. 312: 687-698 (2001).

Oren, M., *Decision making by p53: life, death and cancer*. Cell Death Differ, 2003. 10(4): p. 431-42.

Ren, B., et al., *Genome-wide location and function of DNA binding proteins*. Science, 2000. 290(5500): p. 2306-9.

Rao, D. N., et al., J. Mol. Biol. 209: 599-606 (1989).

Saha, S., et al., *Using the transcriptome to annotate the genome*. Nat Biotechnol, 2002. 20(5): p. 508-12.

Sambrook J. and Russell D. W., 2001, Molecular Cloning, Cold Spring Harbor Laboratory Press.

Strausberg, R. L., et al., 1999, *Science*, 286: 455-457.

Szybalski, W., 1985, Gene, 40:169.

Taverner, N. V., J. C. Smith, and F. C. Wardle, *Identifying transcriptional targets*. Genome Biol, 2004. 5(3): p. 210.

Velculescu, V. E., et al., *Serial analysis of gene expression*. Science, 1995. 270(5235): p. 484-7.

Weinmann, A. S., et al., *Isolating human transcription factor targets by coupling chromatin immunoprecipitation and CpG island microarray analysis*. Genes Dev, 2002. 16(2): p. 235-44.

Wingender, E., et al., *TRANSFAC: a database on transcription factors and their DNA binding sites*. Nucleic Acids Res, 1996. 24(1): p. 238-41.

What is claimed is:

1. A vector having the nucleotide sequence of SEQ ID NO:22.

\* \* \* \* \*

SEQUENCE LISTING

<160> NUMBER OF SEQ ID NOS: 35

<210> SEQ ID NO 1
<211> LENGTH: 33
<212> TYPE: DNA
<213> ORGANISM: Artificial
<220> FEATURE:
<223> OTHER INFORMATION: oligonucleotide primer with homology to bacterial cloning vector
<220> FEATURE:
<221> NAME/KEY: misc_feature
<222> LOCATION: (1)..(33)
<223> OTHER INFORMATION: n is a,c,g, or t
<220> FEATURE:
<221> NAME/KEY: misc_feature
<222> LOCATION: (1)..(33)
<223> OTHER INFORMATION: v is a,c,g

<400> SEQUENCE: 1
gagctccttc tggagttttt tttttttttt tvn                          33

<210> SEQ ID NO 2
<211> LENGTH: 30
<212> TYPE: DNA
<213> ORGANISM: Artificial
<220> FEATURE:
<223> OTHER INFORMATION: oligonucleotide primer with homology to bacterial cloning vector
<220> FEATURE:
<221> NAME/KEY: misc_feature
<222> LOCATION: (1)..(30)
<223> OTHER INFORMATION: n is a,t,c or g

<400> SEQUENCE: 2
aattcgcggc cgcttggatc cgacnnnnnn                              30

<210> SEQ ID NO 3
<211> LENGTH: 20
<212> TYPE: DNA
<213> ORGANISM: Artificial
<220> FEATURE:
<223> OTHER INFORMATION: oligonucleotide primer with homology to bacterial cloning vector

<400> SEQUENCE: 3
gtcggatcca agcggccgcg                                         20

<210> SEQ ID NO 4
<211> LENGTH: 30
<212> TYPE: DNA
<213> ORGANISM: Artificial
<220> FEATURE:
<223> OTHER INFORMATION: oligonucleotide primer with homology to bacterial cloning vector
<220> FEATURE:
<221> NAME/KEY: misc_feature
<222> LOCATION: (1)..(30)
<223> OTHER INFORMATION: n is a,t,c or g

<400> SEQUENCE: 4
aattcgcggc cgcttggatc cgacgnnnnn                              30

<210> SEQ ID NO 5
<211> LENGTH: 19
<212> TYPE: DNA
<213> ORGANISM: Artificial
<220> FEATURE:
<223> OTHER INFORMATION: oligonucleotide primer with homology to bacterial cloning vector

<400> SEQUENCE: 5
tcgacccagg atccaactt                    19

<210> SEQ ID NO 6
<211> LENGTH: 13
<212> TYPE: DNA
<213> ORGANISM: Artificial
<220> FEATURE:
<223> OTHER INFORMATION: oligonucleotide primer with homology to
      bacterial cloning vector
<220> FEATURE:
<221> NAME/KEY: misc_feature
<222> LOCATION: (1)..(1)
<223> OTHER INFORMATION: phosphorylation

<400> SEQUENCE: 6
gttggatcct ggg                          13

<210> SEQ ID NO 7
<211> LENGTH: 17
<212> TYPE: DNA
<213> ORGANISM: Artificial
<220> FEATURE:
<223> OTHER INFORMATION: oligonucleotide primer with homology to
      bacterial cloning vector

<400> SEQUENCE: 7
gtaaaacgac ggccagt                      17

<210> SEQ ID NO 8
<211> LENGTH: 19
<212> TYPE: DNA
<213> ORGANISM: Artificial
<220> FEATURE:
<223> OTHER INFORMATION: oligonucleotide primer with homology to
      bacterial cloning vector

<400> SEQUENCE: 8
ggaaacagct atgaccatg                    19

<210> SEQ ID NO 9
<211> LENGTH: 20
<212> TYPE: DNA
<213> ORGANISM: Artificial
<220> FEATURE:
<223> OTHER INFORMATION: primer with homology to bacterial cloning
      vector

<400> SEQUENCE: 9
taatacgact cactataggg                   20

<210> SEQ ID NO 10
<211> LENGTH: 22
<212> TYPE: DNA
<213> ORGANISM: Artificial
<220> FEATURE:
<223> OTHER INFORMATION: primer with homology to bacterial cloning
      vector

<400> SEQUENCE: 10
gatgtgctgc aaggcgatta ag                22

<210> SEQ ID NO 11
<211> LENGTH: 23
<212> TYPE: DNA

```
<213> ORGANISM: Artificial
<220> FEATURE:
<223> OTHER INFORMATION: primer with homology to bacterial cloning
      vector

<400> SEQUENCE: 11
agcggataac aatttcacac agg                                           23

<210> SEQ ID NO 12
<211> LENGTH: 48
<212> TYPE: DNA
<213> ORGANISM: Artificial
<220> FEATURE:
<223> OTHER INFORMATION: Oligonucleotide with homolgy to a bacteria
      cloning vector
<220> FEATURE:
<221> NAME/KEY: misc_feature
<222> LOCATION: (1)..(48)
<223> OTHER INFORMATION: n is a,t,c or g

<400> SEQUENCE: 12
gatccgacnn nnnnnnnnnn nnnnnnnnnn nnnnnnnnnn nnaagttg                48

<210> SEQ ID NO 13
<211> LENGTH: 48
<212> TYPE: DNA
<213> ORGANISM: Artificial
<220> FEATURE:
<223> OTHER INFORMATION: Oligonucleotide with homolgy to a bacteria
      cloning vector
<220> FEATURE:
<221> NAME/KEY: misc_feature
<222> LOCATION: (1)..(48)
<223> OTHER INFORMATION: n is a,t,c or g

<400> SEQUENCE: 13
gatccaactt nnnnnnnnnn nnnnnnnnnn nnnnnnnnnn nnnngtcg                48

<210> SEQ ID NO 14
<211> LENGTH: 29
<212> TYPE: DNA
<213> ORGANISM: Artificial
<220> FEATURE:
<223> OTHER INFORMATION: Oligonucleotide primer with homolgy to a
      bacteria cloning vector

<400> SEQUENCE: 14
cgctctcctg taccgaccct gccgcttac                                     29

<210> SEQ ID NO 15
<211> LENGTH: 29
<212> TYPE: DNA
<213> ORGANISM: Artificial
<220> FEATURE:
<223> OTHER INFORMATION: Oligonucleotide primer with homolgy to a
      bacteria cloning vector

<400> SEQUENCE: 15
aactatcgtc ttgagaccaa cccggtaag                                     29

<210> SEQ ID NO 16
<211> LENGTH: 24
<212> TYPE: DNA
<213> ORGANISM: ARtificial
<220> FEATURE:
<223> OTHER INFORMATION: Oligonucleotide adapter with homolgy to a
      bacteria cloning vector

<400> SEQUENCE: 16
```

```
aattctcgag cggccgcgat atcg                                              24

<210> SEQ ID NO 17
<211> LENGTH: 24
<212> TYPE: DNA
<213> ORGANISM: Artificial
<220> FEATURE:
<223> OTHER INFORMATION: Oligonucleotide adapter with homolgy to a
      bacteria cloning vector

<400> SEQUENCE: 17
aattcgatat cgcggccgct cgag                                              24

<210> SEQ ID NO 18
<211> LENGTH: 3404
<212> TYPE: DNA
<213> ORGANISM: Artificial
<220> FEATURE:
<223> OTHER INFORMATION: bacterial cloning vector

<400> SEQUENCE: 18
gggcgaattc tcgagcggcc gcggatccga cgagagcgcc tgcgtacggc tcgccgcggt        60
ggctggcgct acttcggagg agcccgacgc ggcgcggtcg ttttatacat tcccgcgcg       120 gaggcaacgg aagggcgggg cgcctcgtga ttaggccgcg gaggtcacag gctctgttgt       180
catgaaggtg aaaattaaat gttggaatgg tgtggccact tggctctggg tagccaatga       240
tgagaactgc ggcatctgca ggatggcgtt taatggctgc tgtccagact gtaaggtgcc       300
tggtgatgac tgccccctcg tgtggggaca gtgctcccac tgcttccaca tgcactgcat       360
cctcaagtgg ctgaatgcgc agcaggtgca gcagcactgc cccatgtgtc gccaggagtg       420
gaagttcaaa gagtgaagcc cgtgccgtgc cacttccctc tcctgtgctg tgccaggctc       480
agccccttcc ctccctcccc tccccacat acagcacccc aagtccccctc cacacagcac       540 agtggtgccc agagatctcg gtctgtgccg gggacaagga tgctttctgt ttggctggga       600
caaggttgaa aggagctttg ctgactgttt tgttttccca tcacattgac actttattca       660
ataagtaaaa ctcattacag ttccaagtcg gatcctgggt cgacctgcag gcatgcaagc       720
ttgagtattc tatagtgtca cctaaatagc ttggcgtaat catggtcata gctgtttcct       780
gtgtgaaatt gttatccgct cacaattcca cacaacatac gagccggaag cataaagtgt       840
aaagcctggg gtgcctaatg agtgagctaa ctcacattaa ttgcgttgcg ctcactgccc       900
gctttccagt cgggaaacct gtcgtgccag ctgcattaat gaatcggcca acgcgcgggg       960
agaggcggtt tgcgtattgg gcgctctccc gcttcctcgc tcactgactc gctgcgctcg      1020
gtcgttcggc tgcggcgagc ggtatcagct cactcaaagg cggtaatacg gttatccaca      1080
gaatcagggg ataacgcagg aaagaacatg tgagcaaaag gccagcaaaa ggccaggaac      1140
cgtaaaaagg ccgcgttgct ggcgtttttc cataggctcc gcccccctga cgagcatcac      1200
aaaaatcgac gctcaagtca gaggtggcga aacccgacag gactataaag ataccaggcg      1260
tttccccctg gaagctccct cgtgcgctct cctgttccga ccctgccgct taccggatac      1320
ctgtccgcct ttctcccttc gggaagcgtg gcgctttctc atagctcacg ctgtaggtat      1380
ctcagttcgg tgtaggtcgt tcgctccaag ctgggctgtg tgcacgaacc cccgttcag       1440 cccgaccgct gcgccttatc cggtaactat cgtcttgaga ccaacccggt aagacacgac      1500
ttatcgccac tggcagcagc cactggtaac aggattagca gagcgaggta tgtaggcggt      1560
gctacagagt tcttgaagtg gtggcctaac tacggctaca ctagaaggac agtatttggt      1620
```

```
atctgcgctc tgctgaagcc agttaccttc ggaaaaagag ttggtagctc ttgatccggc    1680
aaacaaacca ccgctggtag cggtggtttt tttgtttgca agcagcagat tacgcgcaga    1740
aaaaaaggat ctcaagaaga tcctttgatc ttttctacgg ggtctgacgc tcagtggaac    1800
gaaaactcac gttaagggat tttggtcatg agattatcaa aaaggatctt cacctagatc    1860
cttttaaatt aaaaatgaag ttttaaatca atctaaagta tatatgagta aacttggtct    1920
gacagttacc aatgcttaat cagtgaggca cctatctcag cgatctgtct atttcgttca    1980
tccatagttg cctgactccc cgtcgtgtag ataactacga tacgggaggg cttaccatct    2040
ggccccagtg ctgcaatgat accgcgacac ccacgctcac cggctccaga tttatcagca    2100
ataaaccagc cagccggaag ggccgagcgc agaagtggtc ctgcaacttt atccgcctcc    2160
atccagtcta ttaattgttg ccgggaagct agagtaagta gttcgccagt taatagtttg    2220
cgcaacgttg ttggcattgc tacaggcatc gtggtgtcac gctcgtcgtt tggtatggct    2280
tcattcagct ccggttccca acgatcaagg cgagttacat gatccccat gttgtgcaaa    2340 aaagcggtta gctccttcgg tcctccgatc gttgtcagaa gtaagttggc cgcagtgtta    2400
tcactcatgg ttatggcagc actgcataat tctcttactg tcatgccatc cgtaagatgc    2460
ttttctgtga ctggtgagta ctcaaccaag tcattctgag aatagtgtat gcggcgaccg    2520
agttgctctt gcccggcgtc aatacgggat aataccgcgc cacatagcag aactttaaaa    2580
gtgctcatca ttggaaaacg ttcttcgggg cgaaaactct caaggatctt accgctgttg    2640
agatccagtt cgatgtaacc cactcgtgca cccaactgat cttcagcatc ttttactttc    2700
accagcgttt ctgggtgagc aaaaacagga aggcaaaatg ccgcaaaaaa gggaataagg    2760
gcgacacgga aatgttgaat actcatactc ttcctttttc aatattattg aagcatttat    2820
cagggttatt gtctcatgag cggatacata tttgaatgta tttagaaaaa taaacaaata    2880
ggggttccgc gcacatttcc ccgaaaagtg ccacctgacg tctaagaaac cattattatc    2940
atgacattaa cctataaaaa taggcgtatc acgaggccct ttcgtctcgc gcgtttcggt    3000
gatgacggtg aaaacctctg acacatgcag ctcccggaga cggtcacagc ttgtctgtaa    3060
gcggatgccg ggagcagaca gcccgtcag ggcgcgtcag cgggtgttgg cgggtgtcgg    3120
ggctggctta actatgcggc atcagagcag attgtactga gagtgcacca tatgcggtgt    3180
gaaataccgc acagatgcgt aaggagaaaa taccgcatca ggcgccattc gccattcagg    3240
ctgcgcaact gttgggaagg gcgacacgtg cgggcctctt cgctattacg ccagctggcg    3300 aaaggggat gtgctgcaag gcgattaagt tgggtaacgc cagggttttc ccagtcacga    3360
cgttgtaaaa cgacggccag tgaattgtaa tacgactcac tata                    3404
```

<210> SEQ ID NO 19
<211> LENGTH: 10
<212> TYPE: DNA
<213> ORGANISM: Artificial
<220> FEATURE:
<223> OTHER INFORMATION: mammalian p53 consensus sequence
<220> FEATURE:
<221> NAME/KEY: misc_feature
<223> OTHER INFORMATION: r is a purine (A or G)
<220> FEATURE:
<221> NAME/KEY: misc_feature
<223> OTHER INFORMATION: w is A or T
<220> FEATURE:
<221> NAME/KEY: misc_feature
<223> OTHER INFORMATION: y is a pyrimidine (C or T)

<400> SEQUENCE: 19 rrrcwwgyyy 10

<210> SEQ ID NO 20
<211> LENGTH: 20
<212> TYPE: DNA
<213> ORGANISM: Artificial
<220> FEATURE:
<223> OTHER INFORMATION: mammalian p53 consensus sequence

<400> SEQUENCE: 20
gaacatgtcc caacatgttg 20

<210> SEQ ID NO 21
<211> LENGTH: 20
<212> TYPE: DNA
<213> ORGANISM: Artificial
<220> FEATURE:
<223> OTHER INFORMATION: mammalian p53 consensus sequence

<400> SEQUENCE: 21
agacaagccc gggcaaggcc 20

<210> SEQ ID NO 22
<211> LENGTH: 2770
<212> TYPE: DNA
<213> ORGANISM: Artificial
<220> FEATURE:
<223> OTHER INFORMATION: Bacterial Cloning Vector

<400> SEQUENCE: 22
gggcgaattc gatatcgcgg ccgcgaggag tatggatccg actcgagtcg gatcctggct 60
cctcgtcgac ctgcaggcat gcaagcttga gtattctata gtgtcaccta aatagcttgg 120
cgtaatcatg gtcatagctg tttcctgtgt gaaattgtta tccgctcaca attccacaca 180
acatacgagc cggaagcata aagtgtaaag cctggggtgc ctaatgagtg agctaactca 240
cattaattgc gttgcgctca ctgcccgctt tccagtcggg aaacctgtcg tgccagctgc 300
attaatgaat cggccaacgc gcggggacag gcggtttgcg tattgggcgc tcttccgctt 360
cctcgctcac tgactcgctg cgctcggtcg ttcggctgcg gcgagcggta tcagctcact 420
caaaggcggt aatacggtta tccacagaat caggggataa cgcaggaaag aacatgtgag 480
caaaaggcca gcaaaaggcc aggaaccgta aaaaggccgc gttgctggcg ttttttcgata 540
ggctccgccc cctgacgag catcacaaaa atcgacgctc aagtcagagg tggcgaaacc 600
cgacaggact ataaagatac caggcgtttc ccctggaag ctccctcgtg cgctctcctg 660
taccgaccct gccgcttacc ggatacctgt ccgcctttct cccttcggga agcgtggcgc 720
tttctcatag ctcacgctgt aggtaactca gttcggtgta ggtcgttcgc tccaagctgg 780
gctgtgtgca cgaaccccc gttcagcccg accgctgcgc cttatccggt aactatcgtc 840
ttgagaccaa cccggtaaga cacgacttat cgccactggc agcagccact ggtaacagga 900
ttagcagagc gaggtatgta ggcggtgcta cagagttctt gaagtggtgg cctaactacg 960
gctacactag aaggacagta tttggtatct gcgctctgct gaagccagtt accttcggaa 1020
aaagagttgg tagctcttga tccggcaaac aaaccaccgc tggtagcggt ggtttttttg 1080
tttgcaagca gcagattacg cgcagaaaaa aaggatctca agaagatcct ttgatctttt 1140
ctacggggtc tgacgctcag tggaacgaaa actcacgtta agggattttg gtcatgagat 1200
tatcaaaaag gatcttcacc tagatccttt taaattaaaa atgaagtttt aaatcaatct 1260

```
aaagtatata tgagtaaact tggtctgaca gttaccaatg cttaatcagt gaggcaccta    1320
tctcagcgat ctgtctattt cgttcatcca tagttgcctg actccccgtc gtgtagataa    1380
ctacgatacg ggagggctta ccatctggcc ccagtgctgc aatgataccg cgagacccac    1440
gctcaccggc tccagattta tcagcaataa accagccagc cggaagggcc gagcgcagaa    1500
gtggtcctgc aactttatcc gcctccatcc agtctattaa ttgttgccgg gaagctagag    1560
taagtagttc gccagttaat agtttgcgca acgttgttgg cattgctaca ggcatcgtgg    1620
tgtcacgctc gtcgtttggt atggcttcat tcagctccgg ttcccaacga tcaaggcgag    1680
ttacatgatc ccccatgttg tgcaaaaaag cggttagctc cttcggtcct ccgatcgttg    1740
tcagaagtaa gttggccgca gtgttatcac tcatggttat ggcagcactg cataattctc    1800
ttactgtcat gccatccgta agatgctttt ctgtgactgg tgagtactca accaagtcat    1860
tctgagaata gtgtatgcgg cgaccgagtt gctcttgccc ggcgtcaata cgggataata    1920
ccgcgccaca tagcagaact ttaaaagtgc tcatcattgg aaaacgttct cggggcgaa    1980 aactctcaag gatcttaccg ctgttgagat ccagttcgat gtaacccact cgtgcaccca    2040
actgatcttc agcatctttt actttcacca gcgtttctgg gtgagcaaaa acaggaaggc    2100
aaaatgccgc aaaaaaggga ataagggcga cacggaaatg ttgaatactc atactcttcc    2160
tttttcaata ttattgaagc atttatcagg gttattgtct catgagcgga tacatatttg    2220
aatgtattta gaaaaataaa caaatagggg ttccgcgcac atttccccga aaagtgccac    2280
ctgacgtcta agaaaccatt attatcatga cattaaccta taaaaatagg cgtatcacga    2340
ggccctttcg tctcgcgcgt ttcggtgatg acggtgaaaa cctctgacac atgcagctcc    2400
cggagacggt cacagcttgt ctgtaaccgg atgccgggag cagacaagcc cgtcagggcg    2460
cgtcagcggg tgttggcggg tgtcggggct ggcttaacta tgcggcatca gagcagattg    2520
tactgagagt gcaccatatg cggtgtgaaa taccgcacag atgcgtaagg agaaaatacc    2580
gcatcaggcg ccattcgcca ttcaggctgc gcaactgttg ggaagggcga tcggtgcggg    2640
cctcttcgct attacgccag ctggcgaaag ggggatgtgc tgcaaggcga ttaagttggg    2700
taacgccagg gttttcccag tcacgacgtt gtaaaacgac ggccagtgaa ttgtaatacg    2760
actcactata                                                          2770
```

<210> SEQ ID NO 23
<211> LENGTH: 54
<212> TYPE: DNA
<213> ORGANISM: Artificial
<220> FEATURE:
<223> OTHER INFORMATION: oligonucleotide with homology to bacterial
      cloning vector

<400> SEQUENCE: 23

```
gcggccgcga ggagtatgga tccgactcga gtcggatcct ggctcctcgt cgac          54
```

<210> SEQ ID NO 24
<211> LENGTH: 26
<212> TYPE: DNA
<213> ORGANISM: Artificial
<220> FEATURE:
<223> OTHER INFORMATION: oligonucleotide with homology to bacterial
      cloning vector

<400> SEQUENCE: 24

```
gcggccgcga ggagtatgga tccgac                                         26
```

```
<210> SEQ ID NO 25
<211> LENGTH: 24
<212> TYPE: DNA
<213> ORGANISM: Artificial
<220> FEATURE:
<223> OTHER INFORMATION: oligonucleotide with homology to bacterial
      cloning vector

<400> SEQUENCE: 25
gtcggatcct ggctcctcgt cgac                                              24

<210> SEQ ID NO 26
<211> LENGTH: 10
<212> TYPE: DNA
<213> ORGANISM: mammalian
<220> FEATURE:
<221> NAME/KEY: polyA_site
<222> LOCATION: (1)..(10)

<400> SEQUENCE: 26
aaaaaaaaaa                                                              10

<210> SEQ ID NO 27
<211> LENGTH: 54
<212> TYPE: DNA
<213> ORGANISM: Artificial
<220> FEATURE:
<223> OTHER INFORMATION: Oligonucleotide with homology to bacterial
      cloning vector

<400> SEQUENCE: 27
gcgcggcgct cctcataacct aggctgagct cagcctagga ccgaggagca gctg            54

<210> SEQ ID NO 28
<211> LENGTH: 26
<212> TYPE: DNA
<213> ORGANISM: Artificial
<220> FEATURE:
<223> OTHER INFORMATION: oligonucleotide with homology to bacterial
      cloning vector

<400> SEQUENCE: 28
cgccggcgct cctcataacct aggctg                                           26

<210> SEQ ID NO 29
<211> LENGTH: 24
<212> TYPE: DNA
<213> ORGANISM: Artificial
<220> FEATURE:
<223> OTHER INFORMATION: oligonucleotide with homology to bacterial
      cloning vector

<400> SEQUENCE: 29
cagcctagga ccgaggagca gctg                                              24

<210> SEQ ID NO 30
<211> LENGTH: 10
<212> TYPE: DNA
<213> ORGANISM: mammalian

<400> SEQUENCE: 30
aaaaaaaaaa                                                              10

<210> SEQ ID NO 31
<211> LENGTH: 24
<212> TYPE: DNA
<213> ORGANISM: Mammalian
```

```
<400> SEQUENCE: 31
aaaaaaaaaa aaaaaaaaaa aaaa                                      24

<210> SEQ ID NO 32
<211> LENGTH: 16
<212> TYPE: DNA
<213> ORGANISM: Artificial
<220> FEATURE:
<223> OTHER INFORMATION: Bacterial coding vector

<400> SEQUENCE: 32
tttttttttt tttttt                                               16

<210> SEQ ID NO 33
<211> LENGTH: 54
<212> TYPE: DNA
<213> ORGANISM: Artificial
<220> FEATURE:
<223> OTHER INFORMATION: oligonucleotide with homology to bacterial
      cloning vector

<400> SEQUENCE: 33
gtcgacgagg agccaggatc cgactcgagt cggatccata ctcctcgcgg ccgc     54

<210> SEQ ID NO 34
<211> LENGTH: 26
<212> TYPE: DNA
<213> ORGANISM: Artificial
<220> FEATURE:
<223> OTHER INFORMATION: oligonucleotide with homology to bacterial
      cloning vector

<400> SEQUENCE: 34
gtcggatcca tactcctcgc ggccgc                                    26

<210> SEQ ID NO 35
<211> LENGTH: 24
<212> TYPE: DNA
<213> ORGANISM: Artificial
<220> FEATURE:
<223> OTHER INFORMATION: oligonucleotide with homology to bacterial
      cloning vector

<400> SEQUENCE: 35
gtcgacgagg agccaggatc cgac                                      24
```